(12) United States Patent
Kouyama

(10) Patent No.: US 8,344,180 B2
(45) Date of Patent: Jan. 1, 2013

(54) HYDRAZINE AMIDE DERIVATIVE

(75) Inventor: Naoki Kouyama, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 749 days.

(21) Appl. No.: 12/310,566

(22) PCT Filed: Aug. 28, 2007

(86) PCT No.: PCT/JP2007/066604
§ 371 (c)(1),
(2), (4) Date: Feb. 27, 2009

(87) PCT Pub. No.: WO2008/026563
PCT Pub. Date: Mar. 6, 2008

(65) Prior Publication Data
US 2010/0004295 A1    Jan. 7, 2010

(30) Foreign Application Priority Data
Aug. 30, 2006 (JP) ................. 2006-233006

(51) Int. Cl.
C07C 303/00 (2006.01)
C07C 241/00 (2006.01)
C07C 215/00 (2006.01)
C07C 211/00 (2006.01)

(52) U.S. Cl. ........... 564/81; 564/310; 564/443; 564/462

(58) Field of Classification Search .................. None
See application file for complete search history.

(56) References Cited

U.S. PATENT DOCUMENTS

| | | | |
|---|---|---|---|
| 5,232,898 A | 8/1993 | Suchy et al. | |
| 6,172,108 B1 | 1/2001 | Vega et al. | |
| 6,271,247 B1 | 8/2001 | Monge Vega et al. | |
| 6,699,891 B1 * | 3/2004 | Kawanishi et al. | 514/352 |
| 7,265,130 B2 * | 9/2007 | Kawanishi et al. | 514/307 |
| 2004/0044052 A1 | 3/2004 | Thomas et al. | |
| 2005/0020645 A1 | 1/2005 | Ohta et al. | |

FOREIGN PATENT DOCUMENTS

| | | |
|---|---|---|
| EP | 1 249 233 | 10/2002 |
| EP | 1 270 557 | 1/2003 |
| EP | 1 405 852 | 4/2004 |
| EP | 1 415 992 | 5/2004 |
| EP | 1 577 301 | 9/2005 |
| EP | 1 760 073 | 3/2007 |
| EP | 1 988 077 | 11/2008 |
| EP | 2 014 285 | 1/2009 |
| EP | 2 017 261 | 1/2009 |
| JP | 2003-183286 | 7/2003 |
| WO | 96/16542 | 6/1996 |
| WO | 02/057220 | 7/2002 |
| WO | 02/68388 | 9/2002 |
| WO | 03/000657 | 1/2003 |
| WO | 2008/026564 | 3/2008 |

OTHER PUBLICATIONS

Morissette, S., et al. "High-throughput crystallization: polymorphs, salts, co-crystals and solvates of pharmaceutical solids," Adv. Drug Delivery Reviews, (2004) 56: 275-300.*
Braga, D., et al. "Making crystals from crystals: a green route to crystal engineering and polymorphism," (2005) 3635-45.*
International Search Report issued Sep. 14, 2007 in the International (PCT) Application of which the present application is the U.S. National Stage.
L. Grundemar et al., "Neuropeptide Y effector systems: perspectives for drug development", TIPS, vol. 15, pp. 153-159, May 1994.
C. Betancur et al., "Nonpeptide antagonists of neuropeptide receptors: tools for research and therapy", TIPS, vol. 18, pp. 372-386, Oct. 1997.
A. A. Balasubramaniam et al., "Neuropeptide Y Family of Hormones: Receptor Subtypes and Antagonists", Peptides, vol. 18, No. 3, pp. 445-457, 1997.

(Continued)

*Primary Examiner* — Porfirio Nazario Gonzalez
*Assistant Examiner* — James Meadows
(74) *Attorney, Agent, or Firm* — Wenderoth, Lind & Ponack, L.L.P.

(57) ABSTRACT

Disclosed are compound having NPY Y5 receptor antagonistic activity of formula (I):

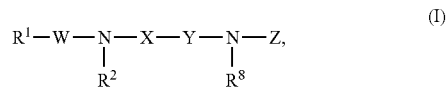

or a pharmaceutically acceptable salt thereof, wherein $R^1$ is optionally substituted lower alkyl, $R^2$ and $R^8$ are each independently hydrogen or lower alkyl, X is optionally substituted cycloalkylene, or $-NR^2-X-$ may be a group of the formula:

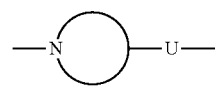

wherein a group of the formula:

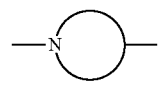

is piperidinediyl, piperazinediyl, pyridindiyl, pyrazinediyl, pyrrolidinediyl or pyrrolediyl, U is a bond, lower alkylene or lower alkenylene, Y is $-OCONR^7-$, $-CONR^7-$ or $-CSNR^7-$, $R^7$ is hydrogen or lower alkyl, Z is optionally substituted carbocyclyl, or optionally substituted heterocyclyl, W is $-S(=O)n-$, n is 2, provided that Z is not carbocyclyl substituted with non-halogeno lower alkoxy, and provided that 5-Methyl-4,5,6,7-tetrahydro-thiazolo[5,4-c]pyridine-2-carboxylic acid [2-[(5-chloro-1H-indole-2-carbonyl)-amino]-5 -(N',N'-dimethyl-hydrazinocarbonyl)-cyclohexyl]-amide and 5-Methyl-4,5,6,7-tetrahydro-thiazolo[5,4-c]pyridine-2-carboxylic acid [2-[(5-chloro-4-fluoro-1H-indole-2-carbonyl)-amino]-5-(N',N'-dimethyl-hydrazinocarbonyl) -cyclohexyl]-amide are excluded.

7 Claims, No Drawings

OTHER PUBLICATIONS

Y. Takebe et al., "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, pp. 466-472, Jan. 1988.

A. Inui et al., "Evidence for Further Heterogeneity of the Receptors for Neuropeptide-Y and Peptide-YY in Tumor Cell Lines Derived from Neural Crest", Endocrinology, vol. 131, No. 5, pp. 2090-2096, 1992.

L. Juanenea et al., "Synthesis and evaluation of new hydrazide derivatives as neuropeptide Y $Y_5$ receptor antagonists for the treatment of obesity", Bioorganic & Medicinal Chemistry, vol. 12, , pp. 4717-4723, 2004.

J. M. Henlin et al., "Parallel synthesis and pharmacological screening of nonpeptide ligands of the neuropeptide Y receptor subtype $Y_5$", Journal of Peptide Research, vol. 57, No. 5, pp. 419-427, 2001.

J. Duhault et al., "Food Intake Regulation in Rodents: $Y_5$ or $Y_1$ NPY receptors or both?", Canadian Journal of Physiology and Pharmacology, vol. 78, No. 2, pp. 173-185, 2000.

Supplementary Partial European Search Report dated Aug. 5, 2010 in Application No. EP 07 79 3048.

J. Branquet et al., "Synthese et activite physiologique de derives d'α-amino-acids, α-disubstitues (1, 2, 3)", Bulletin De La Societe Chimique De France, vol. 10, pp. 2942-2954, 1965.

* cited by examiner

HYDRAZINE AMIDE DERIVATIVE

This application is a U.S. national stage of International Application No. PCT/JP2007/066604 filed August 28, 2007.

FIELD OF THE INVENTION

This invention relates to a novel compound having an NPY Y5 receptor antagonistic activity. The compound is useful as a pharmaceutical composition, especially as an anti-obesity drug.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulatory action on food intake, an anti-seizure activity, a learning-enhancing action, an anti-anxiety activity, an anti-stress activity, etc. in the central nervous system, and it may be pivotally involved in central nervous system diseases such as depression, Alzheimer's disease, Parkinson's disease. NPY is thought to be involved in cardiovascular diseases, since it induces a contraction of smooth muscles such as blood vessels or cardiac muscles in peripheral tissues. Furthermore, NPY is also known to be involved in metabolic diseases such as obesity, diabetes, hormone abnormalities (Non-patent Document 1). Therefore, an NPY receptor antagonist is expected as medicine for preventing or treating the above mentioned various diseases associated with the NPY receptor.

Six subtypes of NPY receptors have now been identified: Y1, Y2, Y3, Y4, Y5, and Y6 (Non-patent Document 2). It has been suggested that the Y5 receptor is at least involved in the feeding behavior and its antagonist is expected as an anti-obesity drug (Non-patent Document 3).

Hydrazine amide derivatives having structures similar to those of compounds of the present invention and exhibiting an NPY Y5 receptor antagonistic activity are disclosed in Patent Document 1 and Non-patent Document 4.

Patent Document 1 discloses hydrazine amide derivatives having phenyl group substituted with electron-donating group, which correspond to the present compounds having carbocyclyl substituted with alkoxy at Z, but does not disclose hydrazine amide derivatives having phenyl group substituted with electron-withdrawing group described in the present invention.

Patent Document 2 and Non-patent Document 4 disclose compounds, wherein $R^1$ is optionally substituted aryl and X is —$CH_2$-cyclohexylene in the present invention, but do not disclose hydrazine amide derivatives having cyclohexyl described in the present invention.

Patent Documents 3 to 9 disclose compounds having hydrazine amide group, which are useful as an antithrombotic agent. Any one of the compounds, however, is cyclohexane derivative having amino group substituted with heteroaryl carbonyl, and antiobesity effect is not mentioned.

[Non-patent Document 1] Trends in Pharmacological Sciences 1994; 15: 153
[Non-patent Document 2] Trends in Pharmacological Sciences 1997; 18: 372
[Non-patent Document 3] Peptides 1997; 18: 445
[Non-patent Document 4] Bioorganic & Medicinal Chemistry 2004; 12: 4717-4723

[Patent Document 1] WO01037826
[Patent Document 2] JP3445204
[Patent Document 3] US2005020645
[Patent Document 4] WO2004058715
[Patent Document 5] JP2003183286
[Patent Document 6] WO2003016302
[Patent Document 7] WO2003000680
[Patent Document 8] WO2003000657
[Patent Document 9] WO2001074774

DISCLOSURE OF INVENTION

Problems to be Solved by the Invention

The present invention provides novel compounds having a strong NPY Y5 receptor antagonistic activity.

Means for Solving the Problem

The present invention includes:

(1) A compound of the formula (I):

[Formula 1]

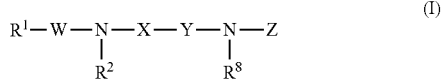

(I)

a pharmaceutically acceptable salt or solvate thereof,
wherein
$R^1$ is optionally substituted lower alkyl, optionally substituted cycloalkyl, optionally substituted amino, optionally substituted aryl, optionally substituted heterocyclyl or optionally substituted heteroaryl,
$R^2$ and $R^8$ are each independently hydrogen or lower alkyl,
X is optionally substituted lower alkylene,
optionally substituted lower alkenylene,
optionally substituted —CO-lower alkylene,
optionally substituted —CO-lower alkenylene or a group of the formula:

[Formula 2]

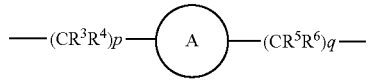

wherein
$R^3$, $R^4$, $R^5$ and $R^6$ are each independently hydrogen or lower alkyl, a group of the formula:

[Formula 3]

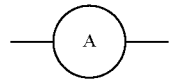

is optionally substituted cycloalkylene, optionally substituted cycloalkenylene, optionally substituted bicycloalkylene or optionally substituted heterocycle-diyl, p and q are each independently 0 or 1, —NR²—X— may be a group of the formula:

[Formula 4]

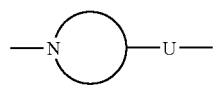

wherein a group of the formula:

[Formula 5]

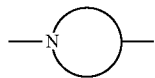

is piperidinediyl, piperazinediyl, pyridindiyl, pyrazinediyl, pyrrolidinediyl or pyrrolediyl,
U is a bond, lower alkylene or lower alkenylene,
Y is —OCONR⁷—, —CONR⁷— or —CSNR⁷—,
R⁷ is hydrogen or lower alkyl,
Z is optionally substituted carbocyclyl, optionally substituted heterocyclyl, optionally substituted lower alkyl, optionally substituted lower alkenyl, optionally substituted lower alkynyl, or Z and R⁸ taken together with the adjacent nitrogen atom to which they are attached may form optionally substituted ring,
W is —S(=O)n-, —C(=O) or optionally substituted alkylene,
n is 1 or 2,
provided that Z is not carbocyclyl substituted with alkoxy,
provided that when R¹ is optionally substituted aryl or optionally substituted heteroaryl, p is 0, and
provided that 5-Methyl-4,5,6,7-tetrahydro-thiazolo[5,4-c]pyridine-2-carboxylic acid [2-[(5-chloro-1H-indole-2-carbonyl)-amino]-5-(N',N'-ethyl-hydrazinocarbonyl)-cyclohexyl]-amide and 5-Methyl-4,5,6,7-tetrahydro-thiazolo[5,4-c]pyridine-2-carboxylic acid [2-[(5-chloro-4-fluoro-1H-indole-2-carbonyl)-amino]-5-(N',N'-dimethyl-hydrazinocarbonyl)-cyclohexyl]-amide are excluded.

(2) The compound, pharmaceutically acceptable salt or solvate thereof of the above (1), wherein X is a group of the formula:

[Formula 6]

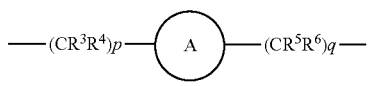

wherein
p and q are each independently 0,
a group of the formula:

[Formula 7]

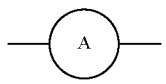

is optionally substituted cycloalkylene.
(3) The compound, pharmaceutically acceptable salt or solvate thereof of the above (1) or (2), wherein W is —S(=O)n- and n is 2.

(4) The compound, pharmaceutically acceptable salt or solvate thereof of any one of the above (1) to (3), wherein R¹ is optionally substituted lower alkyl.
(5) The compound, pharmaceutically acceptable salt or solvate thereof of any one of the above (1) to (4), wherein R² and R⁸ are each independently hydrogen.
(6) The compound, pharmaceutically acceptable salt or solvate thereof of any one of the above (1) to (5), wherein Y is —CONR⁷— and R⁷ has the same meaning as defined in the above (1).
(7) The compound, pharmaceutically acceptable salt or solvate thereof of the above (6), wherein R⁷ is hydrogen.
(8) The compound, pharmaceutically acceptable salt or solvate thereof of any one of the above (1) to (7), wherein Z is optionally substituted carbocyclyl or optionally substituted heterocyclyl.
(9) The compound, pharmaceutically acceptable salt or solvate thereof of the above (8), wherein Z is meta-substituted phenyl, para-substituted phenyl, meta- and para-disubstituted phenyl or meta-disubstituted phenyl.
(10) The compound, pharmaceutically acceptable salt or solvate thereof of the above (8) or (9), wherein Z is a group of the formula:

[Formula 8]

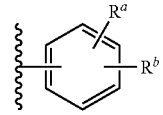

wherein
Ra is hydrogen or electron-withdrawing group,
Rb is electron-withdrawing group.
(11) The compound, pharmaceutically acceptable salt or solvate thereof of the above (10), wherein
Ra is hydrogen, halogen, halogeno lower alkyl, halogeno lower alkoxy, nitro or phenyl,
Rb is halogen, halogeno lower alkyl, halogeno lower alkoxy, nitro or phenyl.
(12) The compound, pharmaceutically acceptable salt or solvate thereof of the above (8), wherein Z is optionally substituted naphthyl.
(13) The compound, pharmaceutically acceptable salt or solvate thereof of the above (8), wherein Z is optionally substituted pyridyl.
(14) A pharmaceutical composition comprising the compound, pharmaceutically acceptable salt or solvate thereof of any one of the above (1) to (13).
(15) The pharmaceutical composition according to the above (14), which has an NPY Y5 receptor antagonistic activity.
(16) The pharmaceutical composition comprising the compound, pharmaceutically acceptable salt or solvate thereof of any one of the above (1) to (13), which is used as an anorectic agent or an anti-obesity agent.
(17) A method for preventing or treating disorders associated with NPY Y5, comprising administrating the compound, pharmaceutically acceptable salt or solvate thereof of any one of the above (1) to (13).
(18) A use of the compound, pharmaceutically acceptable salt or solvate thereof of any one of the above (1) to (13) for the manufacture of a therapeutic agent for disorders associated with NPY Y5.

Effect of the Invention

A compound of the present invention exhibits an NPY Y5 receptor antagonistic activity and is very useful as a medicine especially for preventing and/or treating disorders associated with NPY Y5, e.g. feeding disorder, obesity, hyperorexia, sexual disorder, impaired fertility, depression, epileptic seizure, hypertension, cerebral hemorrhage, congestive heart failure, sleep disorders, etc. and disorders for which obesity is a risk factor, e.g. diabetes, hypertension, hyperlipidemia, arteriosclerosis, acute coronary syndrome, etc.

BEST MODE FOR CARRYING OUT THE INVENTION

Terms used in the present description are explained below. Each term has the same meaning alone or together with other terms in this description.

"Halogen" includes fluorine, chlorine, bromine and iodine. Especially preferred is fluorine, chlorine or bromine.

"Lower alkyl" includes C1 to C10 straight or branched alkyl. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

"Lower alkyl" of $R^1$ is preferably C2 to C10, more preferably C2 to C6 and most preferably ethyl, isopropyl or t-butyl.

"Lower alkyl" in other cases is preferably C1 to C6 and more preferably C1 to C4.

"Halogeno lower alkyl" includes lower alkyl substituted with one or more halogen atoms. The lower alkyl part and the halogen part are the same as the above.

Examples of substituents for "optionally substituted lower alkyl" and "optionally substituted lower alkoxy" include one or more groups selected from Substituent Group α (alpha) defined below. The lower alkyl or the lower alkoxy is optionally substituted with any of these substituent(s) at any position(s).

Substituent Group α (alpha) is a group of halogen, optionally protected hydroxy, mercapto, lower alkoxy, lower alkyl, lower alkenyl, lower alkynyl, amino, lower alkylamino, lower alkoxycarbonylamino, lower alkylthio, acyl, carboxy, lower alkoxycarbonyl, carbamoyl, cyano, cycloalkyl, phenyl, phenoxyl, lower alkylphenyl, lower alkoxyphenyl, halogenophenyl, naphthyl and heterocyclyl.

The lower alkyl part of "lower alkoxy", "lower alkoxycarbonyl", "lower alkoxycarbonyl lower alkyl", "lower alkylphenyl", lower alkoxyphenyl", "lower alkylcarbamoyl", "lower alkylthiocarbamoyl", "lower alkylamino", "halogeno lower alkyl", "halogeno lower alkoxy", "hydroxy lower alkyl", "phenyl lower alkoxy", "lower alkylthio", "phenyl lower alkylthio", "lower alkoxycarbonylamino", "lower alkoxycarbonyl lower alkenyl", "lower alkylsulfinyl", "lower alkylsulfonyl", "aryl lower alkoxycarbonyl", "lower alkyl benzoyl" and "lower alkoxy benzoyl" is the same as the above "lower alkyl".

The lower alkyl part and the halogen part of "halogeno lower alkoxy" are the same as the above.

"Cycloalkyl" includes C3 to C8 and preferably C3 to C6 cyclic alkyl. Examples are cyclopropyl, cyclobutyl, cyclopentyl, cyclohexyl, cycloheptyl, cyclooctyl and the like.

Examples of substituents for "optionally substituted cycloalkyl" include one or more groups selected from Substituent Group β (beta) defined below. The cycloalkyl is optionally substituted with these substituent(s) at any position(s).

Substituent Group β (beta) is a group of (1) halogen; (2) oxo; (3) cyano; (4) nitro; (5) imino optionally substituted with lower alkyl or hydroxy; (6) the following groups (i) to (xxi): (i) hydroxy, (ii) lower alkyl, (iii) lower alkenyl, (iv) lower alkoxy, (v) carboxy, (vi) lower alkoxycarbonyl, (vii) acyl, (viii) acyloxy, (ix) imino, (x) mercapto, (xi) lower alkylthio, (xii) carbamoyl, (xiii) lower alkylcarbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl or (xxi) cycloalkylsulfamoyl, which is optionally substituted with one or more groups selected from Substituent Group a (alpha); (7) the following groups (i) to (v): (i) cycloalkyl, (ii) cycloalkenyl, (iii) cycloalkyloxy, (iv) amino or (v) alkylene dioxy, which is optionally substituted with (a) substituent(s) selected from Substituent Group α (alpha), lower alkyl, lower alkoxy-lower alkyl, optionally protected hydroxyl-lower alkyl, halogeno-lower alkyl, lower alkylsulfonyl and/or arylsulfonyl; and (8) the following groups (i) to (xii): (i) phenyl, (ii) naphthyl, (iii) phenoxy, (iv) phenyl-lower-alkoxy, (v) phenylthio, (vi) phenyl-lower-alkylthio, (vii) phenylazo, (viii) heterocyclyl, (ix) heterocyclyloxy, (x) heterocyclylthio, (xi) heterocyclylcarbonyl and (xii) heterocyclylsulfonyl, which is optionally substituted with (a) substituent(s) selected from Substituent Group α (alpha), lower alkyl, halogeno-lower alkyl and/or oxo.

"Bicycloalkyl" includes a group which is derived by excluding one hydrogen atom from a C5 to C8 aliphatic cycle which consists of two rings that share two or more atoms. Examples are bicyclo[2.1.0]pentyl, bicyclo[2.2.1]heptyl, bicyclo[2.2.2]octyl and bicyclo[3.2.1]octyl.

"Lower alkenyl" includes C2 to C10, preferably C2 to C8 and more preferably C3 to C6 straight or branched alkenyl having at least one double bond at any positions. Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl.

"Lower alkynyl" includes C2 to C10, preferably C2 to C8 and more preferably C3 to C5 straight or branched alkynyl having at least one triple bond at any positions. Examples include ethynyl, propynyl and butynyl.

The lower alkenyl part in "lower alkoxycarbonyl-lower-alkenyl" is the same as the above "lower alkenyl".

Examples of the substituents for "optionally substituted lower alkenyl" include halogen, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, lower alkylphenyl, lower alkoxyphenyl, naphthyl, heterocyclyl and/or the like.

"Acyl" includes (1) C1 to C10, more preferably C1 to C6 and most preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples include formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl and the like.

The acyl part in "acyloxy" is the same as the above.

"Cycloalkenyl" includes the above cycloalkyl with at least one double bond at any position(s) in the ring. Examples include cyclopropenyl, cyclobutenyl, cyclopentenyl, cyclohexenyl, cyclohexadienyl and the like.

Examples of substituents for "optionally substituted cycloalkenyl" include one or more groups selected from Substituent Group α (alpha).

Examples of substituents for "optionally substituted amino" include Substituent Group α (alpha), optionally substituted benzoyl and/or optionally substituted heterocyclylcarbonyl (wherein the substituent is hydroxy, lower alkyl, lower alkoxy and/or lower alkylthio).

"Carbocyclyl" includes "cycloalkyl", "cycloalkenyl", "bicycloalkyl" and "aryl".

"Aryl" includes monocyclic or polycyclic aromatic carbocyclyl, and examples include phenyl, naphtyl, anthryl and phenanthryl. It also includes aryl which is fused with another non-aromatic carbocyclyl, and examples include indanyl, indenyl, biphenylyl, acenaphthyl, tetrahydronaphthyl and fluorenyl. Especially preferred is phenyl.

The aryl part in "aryl lower alkoxycarbonyl" is the same as the above.

Examples of substituents for "optionally substituted aryl", "optionally substituted phenyl" and "a ring formed by taking together Z and $R^8$ with the adjacent nitrogen atom to which they are attached" include one or more groups selected from Substituent Group β (beta).

"Non-aromatic carbocyclyl" includes the above "cycloalkyl", "cycloalkenyl" and "bicycloalkyl".

"Optionally substituted carbocyclyl" includes the above "optionally substituted cycloalkyl", "optionally substituted cycloalkenyl", "optionally substituted bicycloalkyl" and "optionally substituted aryl".

As "carbocyclyl" of Z, preferred are the following:

[Formula 9]

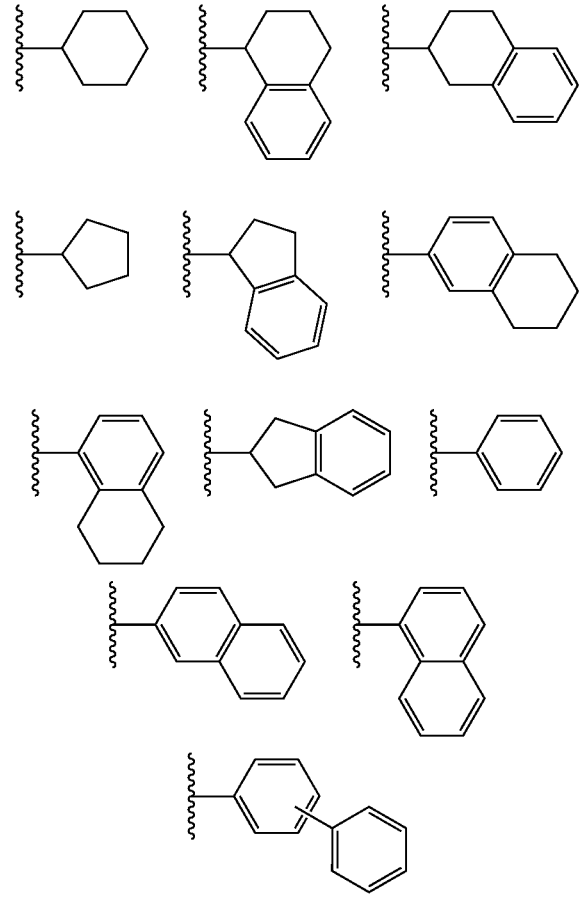

More preferred are the following:

[Formula 10]

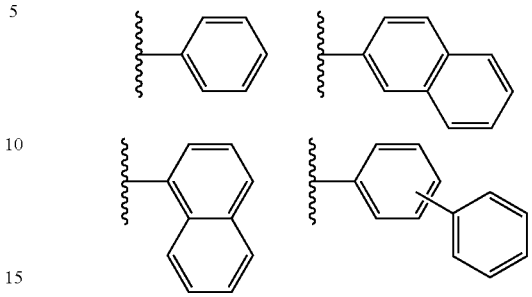

wherein examples of the substituents for "optionally substituted carbocyclyl" of Z include one or more groups selected from Substituent Group β (beta). Preferred are hydrogen, alkyl, halogeno lower alkyl, halogeno lower alkoxy, halogen and phenyl. These substituents may attach to either the aromatic or non-aromatic ring.

"Heterocyclyl" includes heterocycle which contains at least one hetero atom optionally selected from the group of O, S and N in the ring. Examples include 5 -to 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl; di-fused heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, naphthyridinyl, dihydropyridyl, tetrahydroquinolyl, tetrahydrobenzothienyl and oxazolopyridyl; tri-fused heterocyclyl such as carbazolyl, acridinyl, xanthenyl, phenothiazinyl, phenoxathiinyl, phenoxazinyl and dibenzofuryl; non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

"Fused heterocyclyl" which is fused with a ring other than heterocycle (e.g., benzothiazolyl) may have a bonding radical on any ring.

"Heteroaryl" refers to a hetrelocyclyl having aromatic character.

The substituents for "optionally substituted heterocyclyl", "optionally substituted heteroaryl" and "optionally substituted di-fused heterocyclyl " are the same as those for the above "optionally substituted aryl".

The heterocyclyl parts in "heterocyclylcarbonyl", "heterocyclyloxy", "heterocyclylthio" and "heterocyclyl-substituted phenyl" are the same as the above "heterocyclyl".

As "heterocyclyl" of Z, preferred are the following:

[Formula 11]

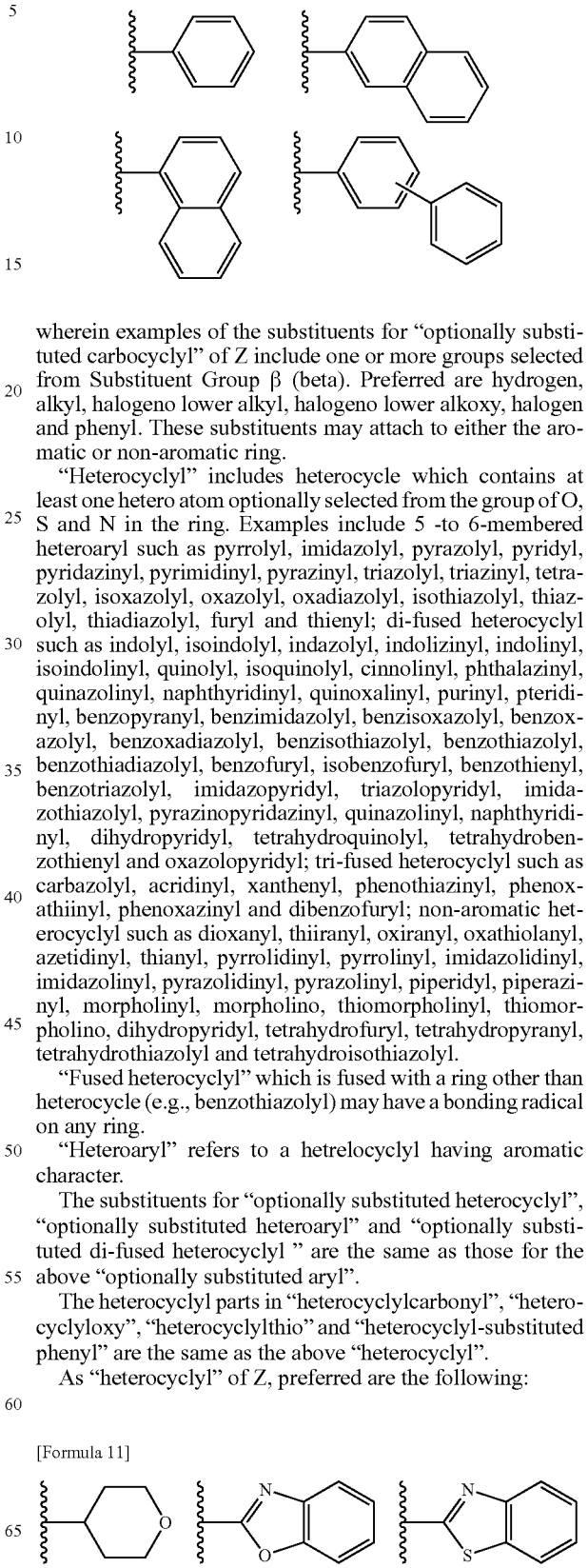

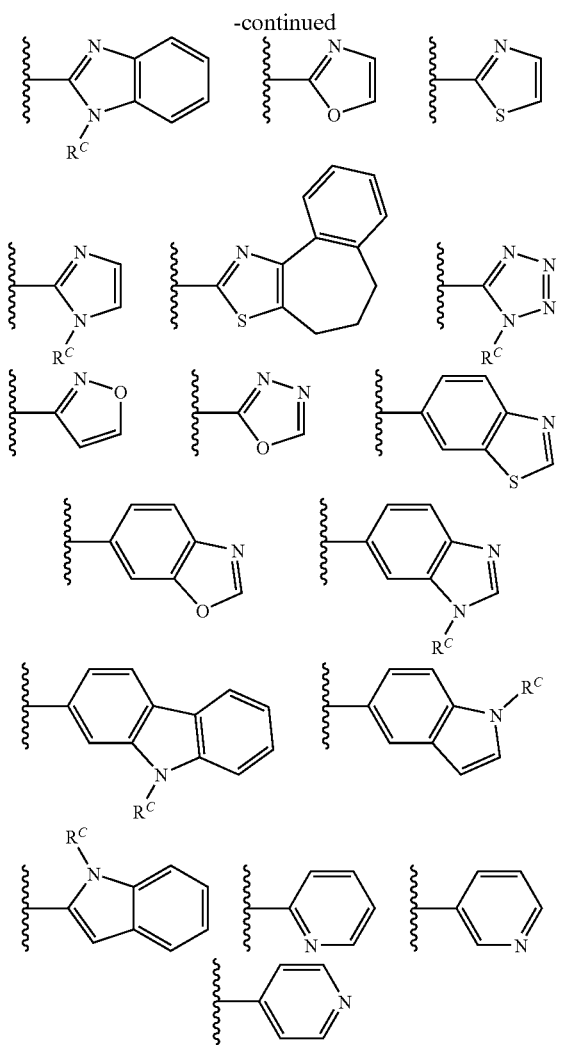

wherein $R^C$ is hydrogen, optionally substituted lower alkyl, optionally substituted carbocyclyl or optionally substituted heterocyclyl.

More preferred are the following:

[Formula 12]

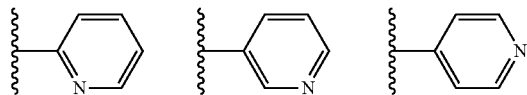

wherein examples of the substituents for "optionally substituted heterocyclyl" of Z include one or more groups selected from Substituent Group β (beta). Preferred is hydrogen, lower alkyl, halogeno lower alkyl, halogeno lower alkoxy, carbocyclyl or heterocyclyl.

As the substituents for "optionally substituted carbocyclyl" and "optionally substituted heterocyclyl" of Z, preferred are halogen, halogeno lower alkyl, halogeno lower alkoxy and phenyl.

"Lower alkylene" includes a bivalent group comprising 1 to 6 of methylene, preferably 2 to 6 of methylene and more preferably 3 to 6 of methylene. Examples are methylene, ethylene, trimethylene, tetramethylene, pentamethylene and hexamethylene. Especially preferred is tetramethylene.

When X is optionally substituted lower alkylene, preferred are trimethylene and tetramethylene.

The lower alkylene part in "lower alkylenedioxy" is the same as the above "lower alkylene". Preferred is methylenedioxy or ethylenedioxy.

"Lower alkenylene" includes a bivalent group comprising 2 to 6 of methylene, preferably 3 to 6 of methylene and more preferably 4 to 5 of methylene, and containing at least one carbon-carbon double bond.

"Optionally substituted —CO-lower alkylene" and "optionally substituted —CO-lower alkenylene" are a group represented by the formula: —CO-D-, wherein D is optionally substituted lower alkylene and a group represented by the formula: —CO-D-, wherein D is optionally substituted lower alkenylene, respectively.

"Cycloalkylene" includes a bivalent group which is derived by excluding one hydrogen atom from the above "cycloalkyl". As cycloalkylene of X, 1,4-cyclohexanediyl is preferable.

"Cycloalkenylene" includes a group containing at least one double bond in the above cycloalkylene.

"Bicycloalkylene" includes a group which is derived by excluding one hydrogen atom from the above "bicycloalkyl". Examples are bicyclo[2.1.0]pentylene, bicyclo[2.2.1]heptylene, bicyclo[2.2.2]octylene, bicyclo[3.2.1]octylene and the like.

"Heterocyclediyl" includes a bivalent group which is derived by excluding one hydrogen atom from the above "heterocyclyl". Preferred is piperidinediyl, piperazinediyl, pyridinediyl, pyrimidinediyl, pyrazinediyl, pyrrolidinediyl or pyrrolediyl. More preferred is piperidinediyl.

"Arylene" includes a bivalent group which is derived by excluding one hydrogen atom from the above "aryl". Preferred is phenylene.

"Heteroarylene" refers to the above "heterocyclediyl" having aromatic character. Examples are pyrrolediyl, imidazolediyl, pyrazolediyl, pyridinediyl, pyridazinediyl, pyrimidinediyl, pyrazinediyl, triazolediyl, triazinediyl, isoxazolediyl, oxazolediyl, oxadiazolediyl, isothiazolediyl, thiazolediyl, thiadiazolediyl, furandiyl, thiophenediyl and the like.

The substituent of "optionally substituted lower alkylene", "optionally substituted lower alkenylene", "optionally substituted cycloalkylene", "optionally substituted cyclohexylene", "optionally substituted bicycloalkylene", "optionally substituted cycloalkenylene", "optionally substituted phenylene", "optionally substituted heterocyclediyl" and "optionally substituted piperidinylene" is one or more groups selected from Substituent Group α (alpha). Preferred is halogen, hydroxy, lower alkyl, halogeno lower alkyl, lower alkoxy, amino, lower alkylamino, acyl, carboxy or lower alkoxycarbonyl. These substituents may be attached at any positions.

When —$NR^2$—X— is a group of the formula:

[Formula 13]

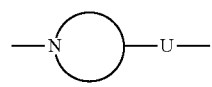

wherein a nitrogen atom (N) is attached to W. U is preferably a bond or methylene. More preferable is a group of the formula:

[Formula 14]

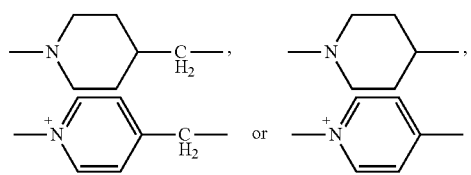

wherein, when a ring is pyridinediyl or pyrazinediyl, the nitrogen atom attached to W may be optionally quaternized.

A ring formed by taking together Z and $R^8$ with the adjacent nitrogen atom to which they are attached is a nonaromatic hetero ring or an aromatic hetero ring which may contain 1 to 4 oxygen and sulfar atoms besides the above nitrogen atom. For example, a group of the formula, which may include one or more groups selected from Substituent Group β (beta), is exemplified as follows:

[Formula 15]

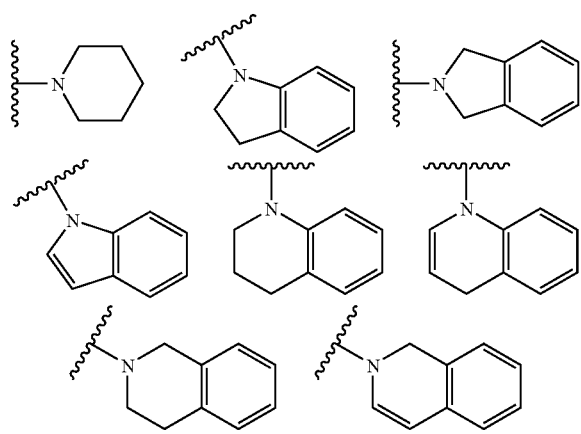

As meta-substituted phenyl, a group of the formula is exemplified as follows:

[Formula 16]

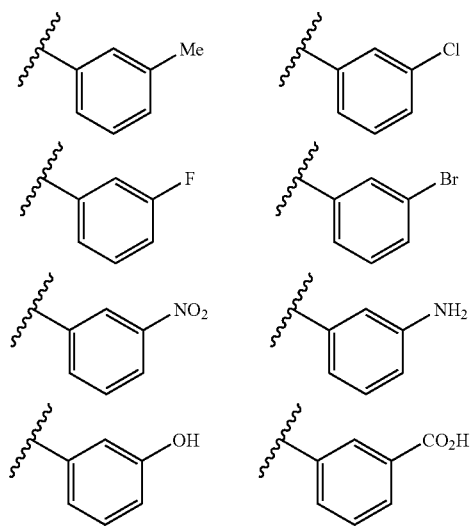

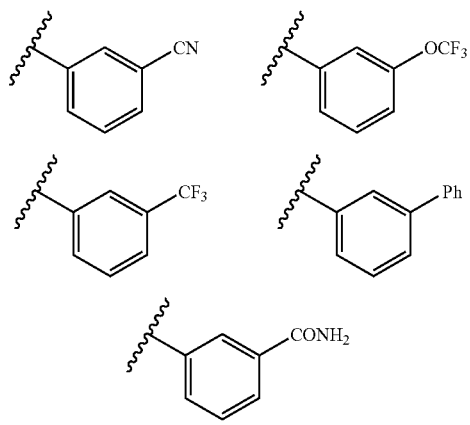

As para-substituted phenyl, a group of the formula is exemplified as follows:

[Formula 17]

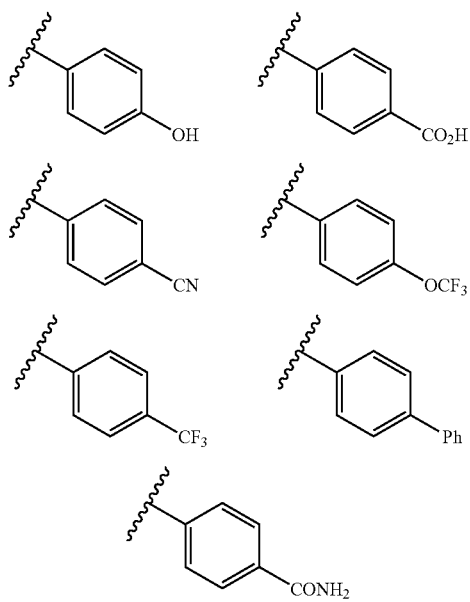

As meta- and para-disubstituted phenyl, a group of the formula is exemplified as follows:

[Formula 18]

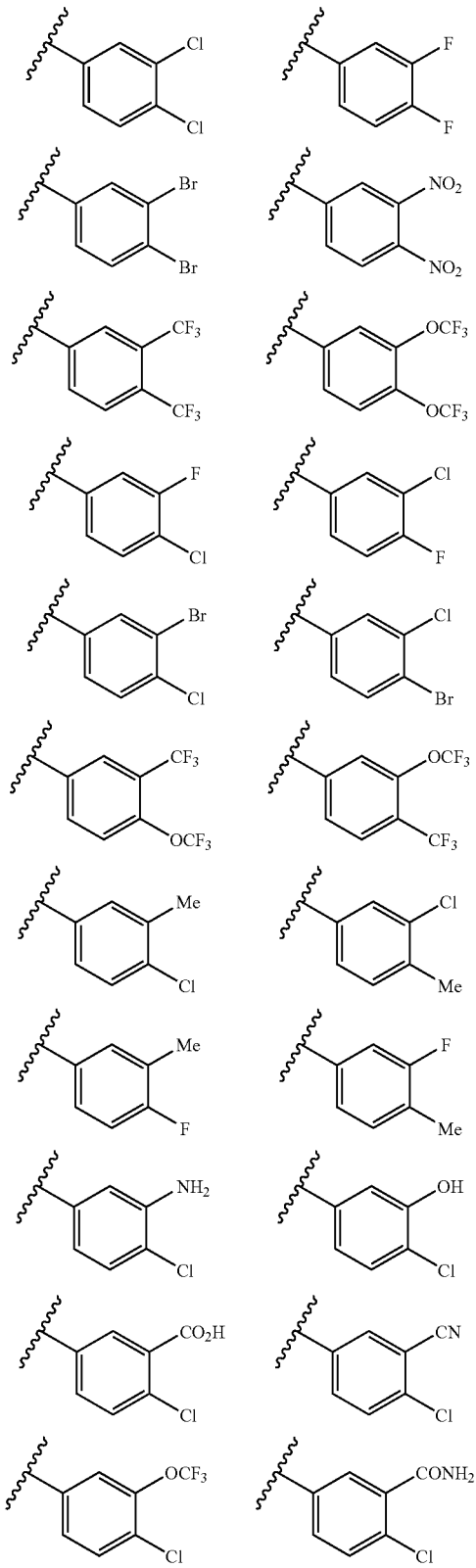

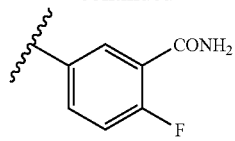

As meta-disubstituted phenyl, a group of the formula is exemplified as follows:

[Formula 19]

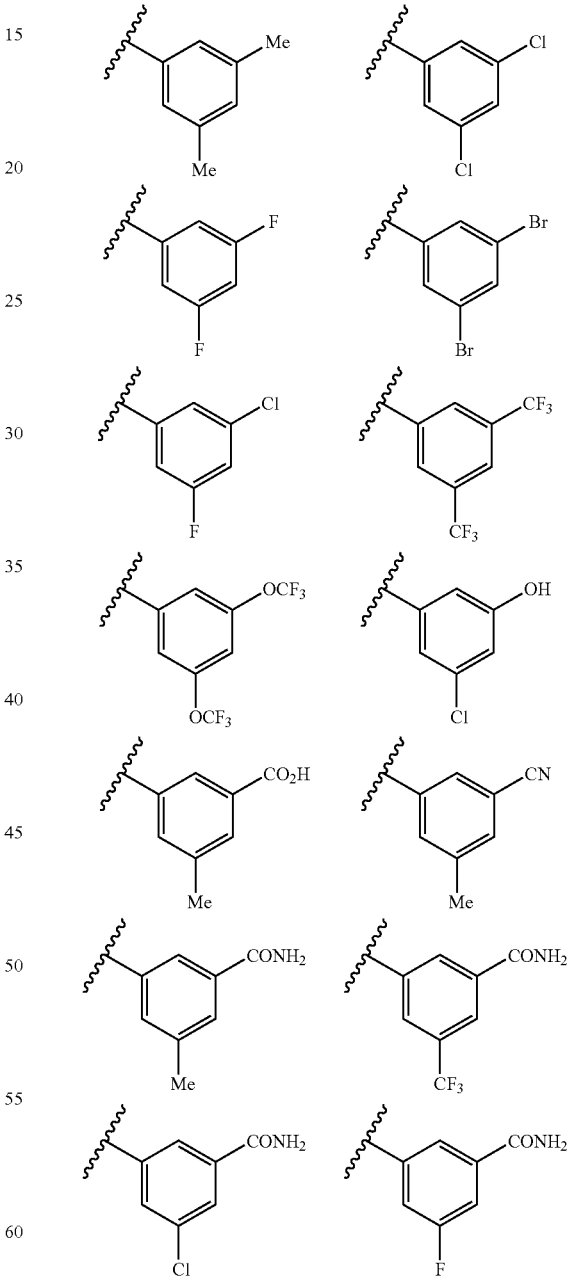

Examples of electron-withdrawing group include halogen, nitro, halogeno lower alkyl, halogeno lower alkoxy, cyano, formyl, acyl, optionally substituted carbamoyl, optionally substituted thiocarbamoyl, ester as exemplified by lower alkyloxycarbonyl, carboxy, phenyl and the like. The group can be selected from any conventional electron withdrawing group. Preferred are halogen, nitro, halogeno lower alkyl, halogeno lower alkoxy and phenyl. More preferred are halogen, halogeno lower alkyl, halogeno lower alkoxy and phenyl.

The compounds of the present invention include any pharmaceutically acceptable salts thereof which can be produced. Examples of "the pharmaceutically acceptable salt" are salts with inorganic acid such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of the present invention include any solvates thereof. Preferred is hydrate and any number of water molecules may be coordinated with the compound of the present invention.

When Compound (I) of the present invention has an asymmetric carbon atom, racemates, all of enantiomers and all of stereoisomers such as diastereomer, epimer and enantiomer thereof are within the scope of the present invention. When Compound (I) of the present invention having one or more double bonds forms an E isomer or Z isomer, both isomers are within the scope of the present invention. When A is cycloalkylene, both cis isomer and trans isomer are within the scope of the present invention. Especially preferred is a trans isomer.

For example, the compound of formula (I) of the present invention can be prepared by the following methods. Each symbol has the same meaning as the above (1). In addition, the treatment of the conventional organic synthesis such as extraction, purification and the like can be used for the preparation of the compound of the present invention.

Compounds wherein Y=CONR$^7$

[Formula 20]

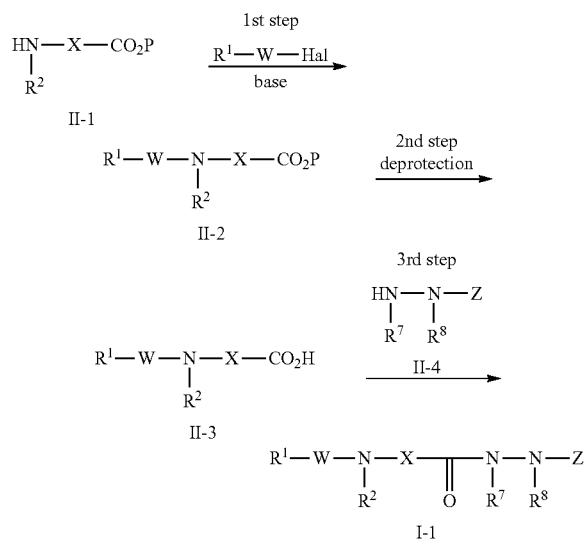

In the above scheme, Hal is halogen, P is carboxylic acid protecting group, and any other symbol has the same meaning as the above. As for Compound (II-1), known compounds or compounds derived from known compounds by conventional methods can be used.

1st Step

1st step is a process for preparing Compound of the formula (II-2) which comprises reacting Compound of the formula (II-1) with R$^1$—W-Hal in the presence of a base.

This reaction can be performed in a solvent of N-dimethylformamide, dimethylsulfoxide, aromatic hydrocarbons (for example, toluene, benzene, xylene or the like), saturated hydrocarbons (for example, cyclohexane, hexane or the like), halogenated hydrocarbons (for example, dichloromethane, chloroform, 1,2-dichloroethane or the like), ethers (for example, tetrahydrofuran, diethyl ether, dioxane, 1,2-dimethoxyethane or the like), esters (for example, methyl acetate, ethyl acetate or the like), ketons (for example, acetone, methyl ethylketone or the like), nitriles (for example, acetonitrile or the like), alcohols (for example, methanol, ethanole, t-butanol or the like), water, a mixed solvent thereof or the like. The base is, for example, metal hydrides (for example, sodium hydride or the like), metal hydroxides (for example, sodium hydroxide, potassium hydroxide, lithium hydroxide, barium hydroxide or the like), metal carbonates (for example, sodium carbonate, calcium carbonate, cesium carbonate or the like), metal alkoxides (for example, sodium methoxide, sodium ethoxide, potassium tert-butoxide or the like), sodium hydrogen carbonates, metallic sodiums and organic amines (for example, triethylamine, diisopropylethylamine, DBU, 2,6-lutidine, pyridin or the like). Preferably this reaction can be performed in a solvent of halogenated hydrocarbons (for example, dichloromethane, chloroform or the like), ethers (for example, tetrahydrofuran, diethyl ether, dioxane or the like) and N-dimethylformamide, with metal hydrides (for example, sodium hydride or the like) or metal alkoxides (for example, sodium methoxide, sodium ethoxide, potassium tert-butoxide or the like) as a base, in the presence of R$^1$—W-Hal within the range of −30 to 100° C. for 0.5 to 24 hours.

2nd Step

2nd step is a process for preparing Compound of the formula (II-3) which comprises deprotecting Compound of the formula (II-2).

This reaction can be performed in an appropriate solvent in the presence of a base. As the solvent and the base, the same solvent and the base described in the above 1st step can be used. Preferably this reaction can be performed in a solvent of alcohols (for example, methanol, ethanol, t-butanol or the like), water, a mixed solvent thereof or the like in the presence of metal hydroxide (for example, sodium hydroxide, potassium hydroxide, lithium hydroxide, barium hydroxide or the like), within the range of −20 to 50° C. for 0.5 to 24 hours. When carboxylic acid protecting group is t-Bu ester, this reaction can be performed in a solvent of halogenated hydrocarbons (for example, dichloromethane, chloroform or the like), esters (for example, methyl acetate, ethyl acetate or the like), ethers (for example, tetrahydrofuran, diethyl ether, dioxane, 1,2-dimethoxyethane or the like), alcohols (for example, methanol, ethanol, t-butanol or the like), water and a mixed solvent thereof in the presence of a strong acid, as exemplified by trifluoroacetic acid, hydrochloric acid or the like, within the range of −20 to 30° C. for 0.5 to 5 hours.

3rd Step

3rd step is a process for preparing Compound of the formula (I-1) which comprises reacting Compound of the formula (II-3) with Compound of the formula (II-4) to form amide compound.

This reaction can be performed in an appropriate solvent in the presence of HOBt, WSC, a base and a compound of the formula (II-4). As the solvent and the base, the same solvent and the base described in the above 1st step can be used.

Preferably this reaction can be performed in a solvent of halogenated hydrocarbons (for example, dichloromethane, chloroform or the like), ethers (for example, tetrahydrofuran, diethyl ether, dioxane, 1,2-dimethoxyethane or the like), and N-dimethylformamide in the presence of an organic amine (for example, triethylamine, diisopropylethylamine, DBU, 2,6-lutidine, pyridin or the like) within the range of −20 to 100° C. for 0.5 to 24 hours.

Compounds Wherein Y=OCONR$^7$

[Formula 21]

$$HN-X-OH \atop R^2 \quad II-5 \xrightarrow{\text{4th step} \atop OCN-NR^8Z}$$

$$HN-X-O-\underset{O}{\overset{\|}{C}}-\underset{R^7}{N}-\underset{R^8}{N}-Z \xrightarrow{\text{5th step} \atop R^1-W-Hal \atop base}$$

II-6

$$R^1-W-\underset{R^2}{N}-X-O-\underset{O}{\overset{\|}{C}}-\underset{R^7}{N}-\underset{R^8}{N}-Z$$

I-2

In the above scheme, Hal is halogen and any other symbol has the same meaning as the above. As for Compound (II-5), known compounds or compounds derived from known compounds by conventional methods can be used.

4th Step

4th step is a process for preparing Compound of the formula (II-6) which comprises reacting Compound of the formula (II-5) with OCNNR$^8$Z.

This reaction can be performed in an appropriate solvent in the presence of OCNNR$^8$Z. As the solvent, the same solvent described in the above 1st step can be used. Preferably this reaction can be performed in a solution of ethers (for example, tetrahydrofuran, diethyl ether, dioxane, 1,2-dimethoxyethane or the like), N-dimethylformamide or aromatic hydrocarbons (for example, toluene, benzene, xylene or the like) within the range of −20 to 100° C. for 0.5 to 24 hours.

5th Step

5th step is a process for preparing Compound of the formula (I-2) which comprises reacting Compound of the formula (II-6) with R$^1$—W-Hal in the presence of a base.

This reaction can be performed in an appropriate solvent in the presence of R$^1$—W-Hal and a base. As the solvent and the base, the same solvent and the base described in the above 1st step can be used. Preferably this reaction can be performed in a solvent of halogenated hydrocarbons (for example, dichloromethane, chloroform or the like), ethers (for example, tetrahydrofuran, diethyl ether, dioxane or the like) or N-dimethylformamide, with metal hydrides (for example, sodium hydride or the like) or metal alkoxides (for example, sodium methoxide, sodium ethoxide, potassium tert-butoxide or the like) as a base, in the presence of R$^1$—W-Hal within the range of −30 to 100° C. for 0.5 to 24 hours.

Compounds Wherein Y=CSNR$^7$

This is a step to prepare Compound (I) wherein Y is CSNR$^7$ which comprises reacting Compound (I) wherein Y is CONR$^7$, which is prepared by any of the above methods, with Lawesson's reagent or phosphorus pentasulfide in an appropriate solvent. As the solvent, the same solvent described in the above 1st step can be used. Preferably this reaction can be performed in a solvent of ethers (for example, tetrahydrofuran, diethyl ether, dioxane or the like), N-dimethylformamide or halogenated hydrocarbons (for example, dichloromethane, chloroform or the like) within the range of 30 to 100° C. for 0.5 to 24 hours.

All of the compounds of the present invention have an NPY Y5 receptor antagonistic activity. Especially preferred are the following compounds:

In the formula (I), a compound wherein R$^1$ is optionally substituted lower alkyl or optionally substituted cycloalkyl is included. Especially preferred is a compound wherein R$^1$ is optionally substituted lower alkyl, R$^2$ and R$^8$ are each independently hydrogen or lower alkyl, and especially preferred is a compound wherein R$^2$ and R$^8$ are hydrogen.

Preferred is a compound wherein X is optionally substituted lower alkylene, optionally substituted alkenylene or a group of the formula:

[Formula 22]

$$-(CR^3R^4)p-\boxed{A}-(CR^5R^6)q-$$

wherein R$^3$, R$^4$, R$^5$ and R$^6$ are each independently hydrogen or lower alkyl, and a group of the formula:

[Formula 23]

$$-\boxed{A}-$$

is optionally substituted cycloalkylene or optionally substituted cycloalkenylene.

p and q are each independently 0 or 1, and especially preferred is a compound wherein p and q are each independently 0.

Especially preferred in the above compounds is a compound wherein a group of the formula:

[Formula 24]

$$-\boxed{A}-$$

is optionally substituted cycloalkylene. Furthermore preferred is a compound wherein X is optionally substituted cycloalkylene.

Y is —OCONR$^7$—, —CONR$^7$— or —CSNR$^7$—, and —CONR$^7$— is especially preferable.

R$^7$ is hydrogen or lower alkyl, and hydrogen is especially preferable.

Z is optionally substituted carbocyclyl, optionally substituted heterocyclyl or optionally substituted lower alkyl, or Z and R$^8$ taken together with the adjacent nitrogen atom form an optionally substituted ring, and as Z, optionally substituted carbocyclyl or optionally substituted heterocyclyl is preferable.

W is —S(=O)n-, —C(=O) or optionally substituted alkylene, and —S(=O)n- or —C(=O) is preferable.

n is 1 or 2, and 2 is preferable.

The NPY Y5 receptor antagonist of the present invention is effective for all of the disorders associated with, directly or indirectly, NPY Y5. For example, disorders associated with NPY Y5 include feeding disorder, obesity, hyperorexia, sexual disorder, impaired fertility, depression, epileptic seizure, hypertension, cerebral hemorrhage, congestive heart failure and sleep disorders; and disorders for which obesity is a risk factor include diabetes, hypertension, hyperlipidemia, arteriosclerosis and acute coronary syndrome. Especially, the NPY Y5 receptor antagonist of the present invention is effective for preventing and/or treating obesity and suppressing food intake. The NPY Y5 receptor antagonist of the present invention can be administered combinationally with other drugs for the above disorders and can be used as a combination formulation for the above disorders.

In addition, the NPY Y5 receptor antagonist of the present invention has a low affinity for NPY Y1 and Y2 receptors, and has a high selectivity for NPY Y5 receptor. NPY has a sustained vasoconstrictive effect on the periphery and this effect is expressed mainly via Y1 receptor. Since Y5 receptor is not involved in this effect at all, the NPY Y5 receptor antagonist has a low risk of inducing side effects due to the peripheral vasoconstriction, and is expected to be used as a safe medicine.

The NPY Y5 receptor antagonist shows an anti-obesity effect by suppressing food intake. Therefore, it is one of the features of the present antagonist not to induce side effects such as dyspepsia caused by an anti-obesity agent which inhibits digestion and absorption, or central nervous system side-effects such as an antidepressant effect due to a serotonin transporter inhibitor that shows an anti-obesity effect.

As an anti-obesity agent or anorectic agent, the compound of the present invention can be administered orally and parenterally. In the case of oral administration, it may be in any usual dosage form such as tablets, granules, powders, capsules, pills, solutions, syrups, buccal tablets and sublingual tablets. In the case of parenteral administration, any usual dosage form is acceptable, for example, injections (e.g., intravenous, intramuscular), suppositories, endermic agents and inhalations. The compound of the present invention is well absorbed orally and therefore, suitably administered in an oral dosage form.

A pharmaceutical composition may be manufactured by mixing an effective amount of the compound of the present invention with various pharmaceutical additives suitable for the dosage form, such as excipients, binders, moistening agents, disintegrants, lubricants and diluents. When the composition is of an injection, an active ingredient can be sterilized together with a suitable carrier to give a pharmaceutical composition.

Examples of the excipients include lactose, saccharose, glucose, starch, calcium carbonate and crystalline cellulose. Examples of the binders include methylcellulose, carboxymethylcellulose, hydroxypropylcellulose, gelatin and polyvinylpyrrolidone. Examples of the disintegrants include carboxymethylcellulose, sodium carboxymethylcellulose, starch, sodium alginate, agar and sodium lauryl sulfate. Examples of the lubricants include talc, magnesium stearate and macrogol. Cacao oil, macrogol, methylcellulose or the like may be used as base materials of suppositories. When the composition is prepared as solutions, emulsified injections or suspended injections, solubilizing agents, suspending agents, emulsifiers, stabilizers, preservatives, isotonic agents and the like which are usually used may be added. For oral preparation, sweetening agents, flavors and the like which are usually used may be added.

The dosage of a compound of the present invention as an anti-obesity agent or anorectic agent should be determined in consideration of the patient's age and body weight, the type and degree of diseases, the administration route and the like. A usual oral dosage for an adult is 0.05 to 100 mg/kg/day and preferable is 0.1 to 10 mg/kg/day. For parenteral administration, although the dosage highly depends on administration routes, a usual dosage is 0.005 to 10 mg/kg/day and preferably 0.01 to 1 mg/kg/day. The daily dose may be administered once a day or in several divided doses.

The present invention is further explained by the following Examples, which are not intended to limit the scope of the present invention.

Example 1

[Formula 25]

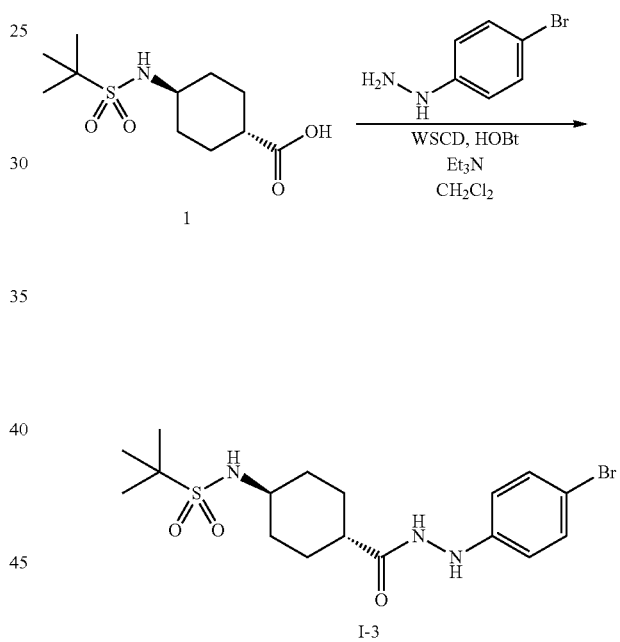

Compound 1 (the synthesis method was described in WO01/037826) (527 mg, 2.0 mmol) and 4-bromobenzoic hydrazide (492 mg, 2.2 mmol) were dissolved in methylene chloride (10 mL), then to the reaction mixture was added triethylamine (492 μL, 4.4 mmol) at room temperature. To the reaction mixture were added WSCD (460 mg, 1.2 mmol) and HOBt (324 mg, 1.2 mmol) successively, then the whole mixture was stirred at room temperature for 16 hours. The whole mixture was purified by silica-gel column chromatography to give Compound I-3 (720 mg, 83%).

$^1$H-NMR (DMSO-$d_6$) δ 1.26 (s, 9H), 1.27-1.51 (m, 4H), 1.80 (d, 2H, J=11.6 Hz), 1.95 (d, 2H, J=11.6 Hz), 2.06-2.18 (m, 1H), 2.95-3.09 (m, 1H), 6.62 (d, 2H, J=8.8 Hz), 6.77 (d, 1H, J=8.4 Hz), 7.26 (d, 2H, J=8.8 Hz), 7.85 (s, 1H), 9.59 (s, 1H).

Example 2

A compound of the formula below was prepared by reacting Compound 1 with the corresponding benzoic hydrazide.

[Formula 26]

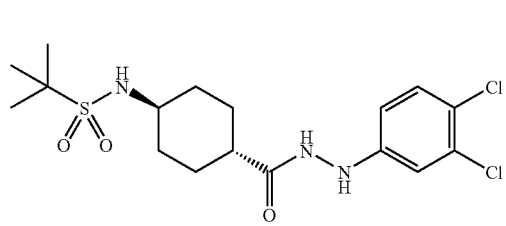

I-4

$^1$H-NMR (DMSO-d$_6$) δ 1.26 (s, 9H), 1.29-1.47 (m, 4H), 1.80 (d, 2H, J=11.6 Hz), 1.95 (d, 2H, J=11.6 Hz), 2.08-2.19 (m, 1H), 2.98-3.10 (m, 1H), 6.64 (dd, 1H, J=8.4, 2.0 Hz), 6.74-6.86 (m, 2H), 7.33 (d, 1H, J=8.4 Hz), 8.12 (s, 1H), 9.68 (s, 1H).

Example 3

[Formula 27]

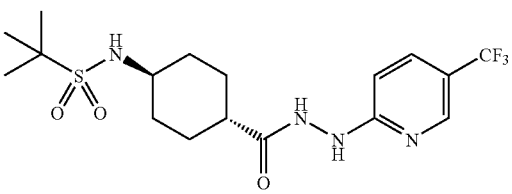

I-5

$^1$H-NMR (DMSO-d$_6$) δ 1.27 (s, 9H), 1.28-1.50 (m, 4H), 1.83 (d, 2H, J=10.4 Hz), 1.96 (d, 2H, J=10.4 Hz), 2.09-2.21 (m, 1H), 2.98-3.10 (m, 1H), 6.60 (d, 1H, J=8.8 Hz), 6.80 (d, 1H, J=8.8 Hz), 7.80 (d, 1H, J=8.8 Hz), 8.37 (s, 1H), 9.03 (s, 1H), 9.83 (s, 1H).

Example 4

[Formula 28]

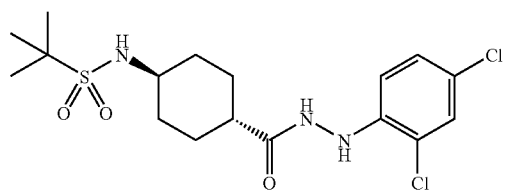

I-6

$^1$H-NMR (DMSO-d$_6$) δ 1.27 (s, 9H), 1.28-1.51 (m, 4H), 1.83 (d, 2H, J=11.6 Hz), 1.96 (d, 2H, J=11.6 Hz), 2.08-2.20 (m, 1H), 2.96-3.10 (m, 1H), 6.69 (d, 1H, J=8.4 Hz), 6.77 (d, 1H, J=8.4 Hz), 7.20 (d, 1H, J=8.8 Hz), 7.39 (s, 1H), 7.54 (s, 1H), 9.75 (s, 1H).

Example 5

[Formula 29]

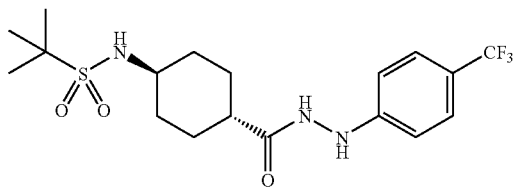

I-7

$^1$H-NMR (DMSO-d$_6$) δ 1.27 (s, 9H), 1.28-1.50 (m, 4H), 1.83 (d, 2H, J=11.4 Hz), 1.96 (d, 2H, J=11.4 Hz), 2.10-2.20 (m, 1H), 2.98-3.10 (m, 1H), 6.66-6.84 (m, 3H), 7.37-7.48 (m, 2H), 8.31 (s, 1H), 9.71 (s, 1H).

Example 6

[Formula 30]

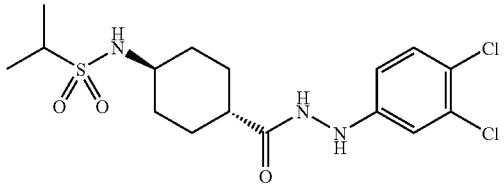

I-8

$^1$H-NMR (DMSO-d$_6$) δ 1.21 (s, 3H), 1.23 (s, 3H), 1.24-1.35 (m, 2H), 1.36-1.51 (m, 2H), 1.80 (d, 2H, J=12.0 Hz), 1.93 (d, 2H, J=12.0 Hz), 2.08-2.19 (m, 1H), 2.99-3.20 (m, 2H), 6.65 (d, 1H, J=8.8 Hz), 6.80 (s, 1H), 6.96 (d, 1H, J=8.0 Hz), 7.33 (d, 1H, J=8.8 Hz), 8.09 (s, 1H), 9.67 (s, 1H).

Example 7

[Formula 31]

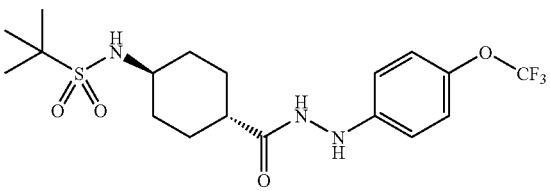

I-9

$^1$H-NMR (DMSO-d$_6$) δ 1.27 (s, 9H), 1.28-1.50 (m, 4H), 1.81 (d, 2H, J=10.4 Hz), 1.96 (d, 2H, J=10.4 Hz), 2.07-2.18

(m, 1H), 2.97-3.11 (m, 1H), 6.64-6.81 (m, 3H), 7.03-7.14 (m, 2H), 7.91 (s, 1H), 9.62 (s, 1H).

Example 8

[Formula 32]

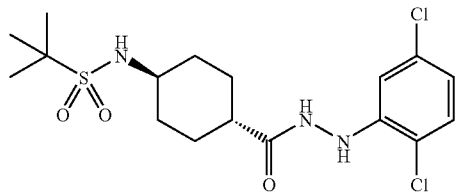

I-10

¹H-NMR (DMSO-d₆) δ 1.27 (s, 9H), 1.28-1.52 (m, 4H), 1.83 (d, 2H, J=11.6 Hz), 1.97 (d, 2H, J=11.6 Hz), 2.10-2.24 (m, 1H), 2.97-3.11 (m, 1H), 6.62 (s, 1H), 6.77 (t, 2H, J=8.4 Hz), 7.29 (d, 1H, J=8.4 Hz), 7.71 (s, 1H), 9.76 (s, 1H).

Example 9

[Formula 33]

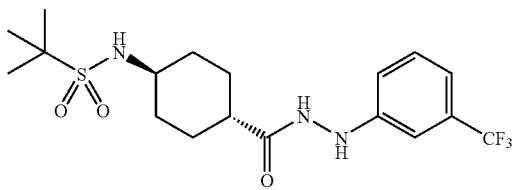

I-11

¹H-NMR (DMSO-d₆) δ 1.27 (s, 9H), 1.28-1.50 (m, 4H), 1.81 (d, 2H, J=11.6 Hz), 1.96 (d, 2H, J=11.6 Hz), 2.09-2.21 (m, 1H), 2.95-3.11 (m, 1H), 6.78 (d, 1H, J=8.4 Hz), 6.88-6.97 (m, 2H), 6.99 (d, 1H, J=8.4 Hz), 7.34 (t, 1H, J=8.0 Hz), 8.14 (s, 1H), 9.70 (s, 1H).

Example 10

[Formula 34]

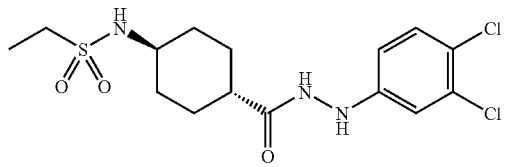

I-12

¹H-NMR (DMSO-d₆) δ 1.19 (t, 3H, J=7.6 Hz), 1.22-1.33 (m, 2H), 1.36-1.52 (m, 2H), 1.79 (d, 2H, J=10.6 Hz), 1.93 (d, 2H, J=10.6 Hz), 2.08-2.20 (m, 1H), 2.90-3.11 (m, 3H), 6.65 (d, 1H, J=8.8 Hz), 6.79 (s, 1H), 7.01 (d, 1H, J=7.6 Hz), 7.34 (d, 1H, J=8.8 Hz), 8.10 (s, 1H), 9.68 (s, 1H).

Example 11

[Formula 35]

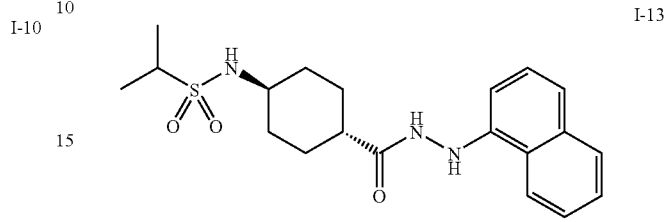

I-13

¹H-NMR (DMSO-d₆) δ 1.22 (s, 3H), 1.23 (s, 3H), 1.28-1.41 (m, 2H), 1.44-1.61 (m, 2H), 1.89 (d, 2H, J=11.6 Hz), 1.98 (d, 2H, J=11.6 Hz), 2.19-2.31 (m, 1H), 2.99-3.21 (m, 2H), 6.67 (d, 1H, J=6.8 Hz), 6.98 (d, 1H, J=8.0 Hz), 7.20-7.35 (m, 2H), 7.36-7.51 (m, 2H), 7.80 (d, 1H, J=7.6 Hz), 8.10-8.23 (m, 2H), 9.75 (s, 1H).

Example 12

[Formula 36]

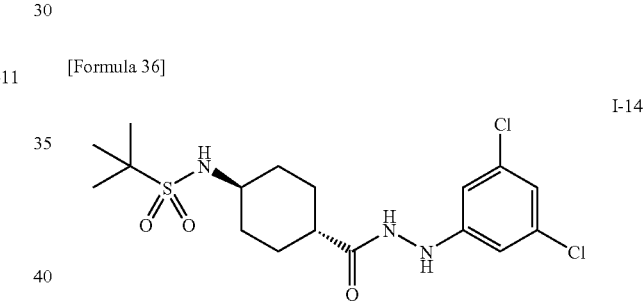

I-14

¹H-NMR (DMSO-d₆) δ 1.26 (s, 9H), 1.27-1.50 (m, 4H), 1.81 (d, 2H, J=11.6 Hz), 1.96 (d, 2H, J=11.6 Hz), 2.09-2.20 (m, 1H), 2.98-3.11 (m, 1H), 6.53-6.82 (m, 4H), 8.26 (s, 1H), 9.69 (s, 1H).

Example 13

[Formula 37]

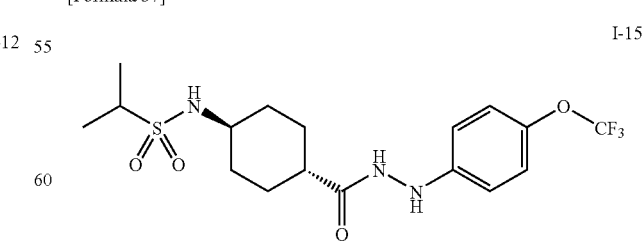

I-15

¹H-NMR (DMSO-d₆) δ 1.21 (s, 3H), 1.23 (s, 3H), 1.24-1.35 (m, 2H), 1.36-1.51 (m, 2H), 1.80 (d, 2H, J=12.0 Hz), 1.93 (d, 2H, J=12.0 Hz), 2.07-2.20 (m, 1H), 2.93-3.20 (m,

2H), 6.65-6.80 (m, 2H), 6.96 (d, 1H, J=7.6 Hz), 7.05-7.16 (m, 2H), 7.91 (s, 1H), 9.63 (s, 1H).

Example 14

[Formula 38]

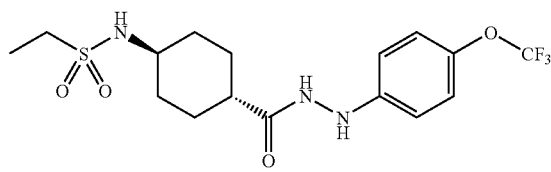

I-16

$^1$H-NMR (DMSO-d$_6$) δ 1.19 (t, 3H, J=7.2 Hz), 1.20-1.33 (m, 2H), 1.36-1.52 (m, 2H), 1.80 (d, 2H, J=11.6 Hz), 1.93 (d, 2H, J=11.6 Hz), 2.05-2.20 (m, 1H), 2.90-3.10 (m, 3H), 6.71 (d, 2H, J=8.8 Hz), 7.02 (d, 1H, J=8.0 Hz), 7.12 (d, 2H, J=8.8 Hz), 7.91 (s, 1H), 9.63 (s, 1H).

Example 15

[Formula 39]

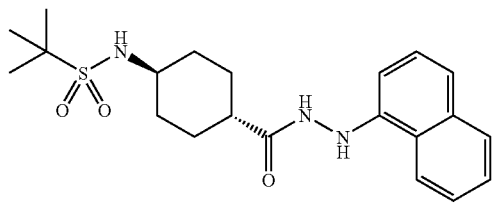

I-17

$^1$H-NMR (DMSO-d$_6$) δ 1.27 (s, 9H), 1.30-1.58 (m, 4H), 1.89 (d, 2H, J=12.8 Hz), 1.99 (d, 2H, J=12.8 Hz), 2.18-2.30 (m, 1H), 2.98-3.12 (m, 1H), 6.64 (d, 1H, J=6.0 Hz), 6.80 (d, 1H, J=8.4 Hz), 7.20-7.35 (m, 2H), 7.38-7.52 (m, 2H), 7.80 (d, 1H, J=7.6 Hz), 8.18 (d, 2H, J=7.6 Hz), 9.73 (s, 1H).

Example 16

[Formula 40]

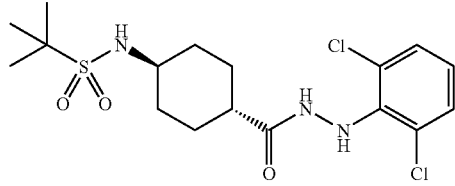

I-18

$^1$H-NMR (DMSO-d$_6$) δ 1.25 (s, 9H), 1.26-1.42 (m, 4H), 1.73 (d, 2H, J=11.6 Hz), 1.91 (d, 2H, J=11.6 Hz), 2.05-2.17 (m, 1H), 2.90-3.07 (m, 1H), 6.75 (d, 1H, J=8.4 Hz), 6.89 (t, 1H, J=8.0 Hz), 7.06 (s, 1H), 7.29 (d, 2H, J=8.0 Hz), 9.85 (s, 1H).

Example 17

[Formula 41]

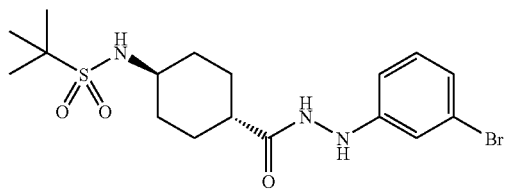

I-19

$^1$H-NMR (DMSO-d$_6$) δ 1.26 (s, 9H), 1.27-1.50 (m, 4H), 1.80 (d, 2H, J=11.6 Hz), 1.96 (d, 2H, J=11.6 Hz), 2.08-2.19 (m, 1H), 2.95-3.11 (m, 1H), 6.65 (d, 1H, J=8.4 Hz), 6.73-6.88 (m, 3H), 7.07 (t, 1H, J=8.0 Hz), 7.94 (s, 1H), 9.61 (s, 1H).

Example 18

[Formula 42]

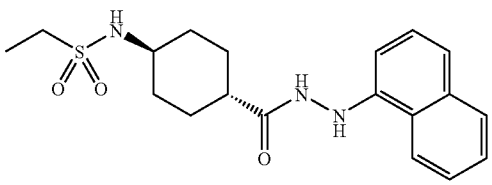

I-20

$^1$H-NMR (DMSO-d$_6$) δ 1.20 (t, 3H, J=7.2 Hz), 1.24-1.39 (m, 2H), 1.43-1.60 (m, 2H), 1.88 (d, 2H, J=11.6 Hz), 1.97 (d, 2H, J=11.6 Hz), 2.18-2.31 (m, 1H), 2.89-3.13 (m, 3H), 6.66 (d, 1H, J=6.0 Hz), 7.04 (d, 1H, J=7.6 Hz), 7.21-7.34 (m, 2H), 7.35-7.51 (m, 2H), 7.80 (d, 1H, J=7.6 Hz), 8.10-8.21 (m, 2H), 9.74 (s, 1H).

Example 19

[Formula 43]

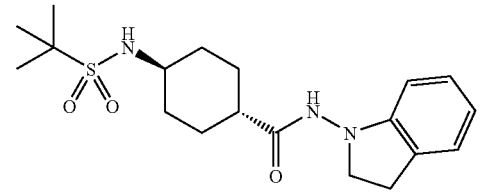

I-21

$^1$H-NMR (DMSO-d$_6$) δ 1.26 (s, 9H), 1.28-1.49 (m, 3H), 1.80 (d, 2H, J=12.0 Hz), 1.94 (d, 2H, J=12.0 Hz), 2.00-2.10 (m, 2H), 2.91 (t, 2H, J=8.0 Hz), 2.95-3.07 (m, 1H), 3.49 (t,

2H, J=8.0 Hz), 6.41 (d, 1H, J=7.6 Hz), 6.69-6.81 (m, 2H), 6.97-7.12 (m, 2H), 9.54 (s, 1H).

Example 20

[Formula 25]

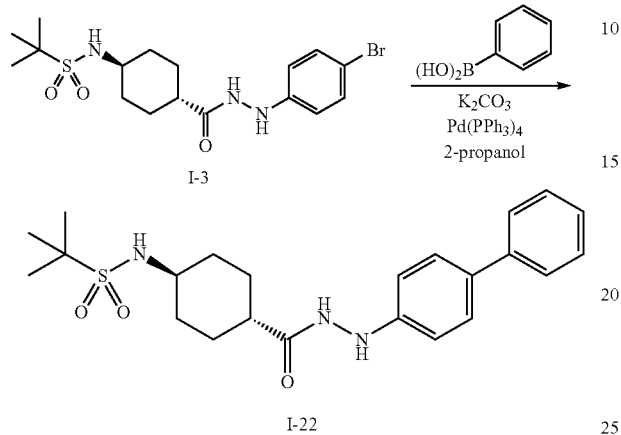

Compound I-3 (432 mg, 1.0 mmol) and phenylboronic acid (183 mg, 1.5 mmol) were dissolved in 2-propanol (2 mL). To the reaction mixture, which was stirred at room temperature, were added 2 M-potassium carbonate aqueous solution (2 mL, 4.0 mmol) and tetrakis(triphenylphosphine)palladium (35 mg, 0.03 mmol). The mixture was stirred using hot water bath of which temperature is 100° C., for 75 min. The whole mixture was poured into saturated ammonium chloride aqueous solution and extracted with ethyl acetate. The extract was washed with water and saturated saline successively, then dried with sodium sulfate. The resulting crude product was purified by silica-gel column chromatography to give Compound I-22 (227 mg, 53%).

$^1$H-NMR (DMSO-$d_6$) δ 1.27 (s, 9H), 1.28-1.52 (m, 4H), 1.82 (d, 2H, J=11.6 Hz), 1.97 (d, 2H, J=11.6 Hz), 2.10-2.21 (m, 1H), 2.97-3.11 (m, 1H), 6.69-6.82 (m, 3H), 7.25 (t, 1H, J=7.6 Hz), 7.39 (t, 2H, J=7.6 Hz), 7.45 (d, 2H, J=8.0 Hz), 7.55 (d, 2H, J=7.6 Hz), 7.81 (s, 1H), 9.62 (s, 1H).

Example 21

A Compound of the formula below was synthesized by reacting Compound I-19 with phenylboronic acid.

[Formula 45]

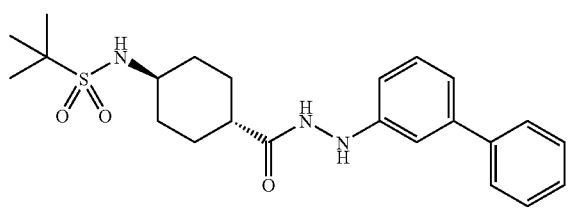

$^1$H-NMR (DMSO-$d_6$) δ 1.27 (s, 9H), 1.30-1.53 (m, 4H), 1.83 (d, 2H, J=11.6 Hz), 1.97 (d, 2H, J=11.6 Hz), 2.10-2.23 (m, 1H), 2.96-3.12 (m, 1H), 6.69 (d, 1H, J=8.4 Hz), 6.79 (d, 1H, J=8.4 Hz), 6.89-7.01 (m, 2H), 7.22 (t, 1H, J=8.0 Hz), 7.34 (t, 1H, J=7.6 Hz), 7.45 (t, 2H, J=7.6 Hz), 7.55 (d, 2H, J=7.6 Hz), 7.78 (s, 1H), 9.64 (s, 1H).

As a compound of the present invention, the following compounds can be synthesized as well as the above Examples. The abbreviations used for $R^1$ are as follows:

[Formula 46]

| | |
|---|---|
| t-Bu | $R^1$-1 |
| i-Pr | $R^1$-2 |
| Et | $R^1$-3 |
| Me | $R^1$-4 |
| $(CH_3)_2N$ | $R^1$-5 |
| cyclopropyl | $R^1$-6 |
| n-Pr | $R^1$-7 |

The abbreviations used for W are as follows:

[Formula 47]

| | |
|---|---|
| SO | W-1 |
| $SO_2$ | W-2 |
| CO | W-3 |

The abbreviations used for $R^2$ are as follows:

[Formula 48]

| | |
|---|---|
| H | $R^2$-1 |
| Me | $R^2$-2 |

The abbreviations used for X are as follows:

[Formula 49]

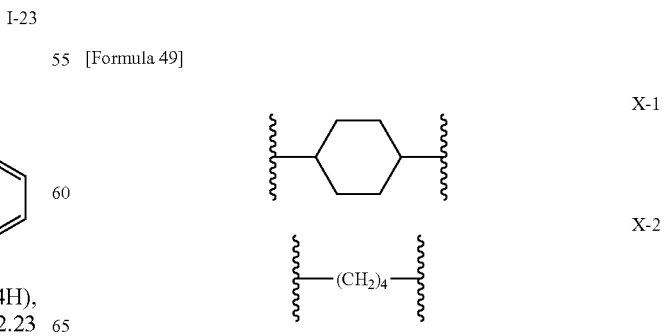

X-1

X-2

The abbreviations used for Y are as follows:
[Formula 50]
CONH     Y-1
CON(CH₃)     Y-2
CSNH     Y-3
CSN(CH₃)     Y-4
The abbreviations used for R⁸ are as follows:
[Formula 51]
H     R⁸-1
Me     R⁸-2
The abbreviations used for Z are as follows:
[Formula 52]
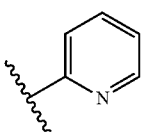 Z-1
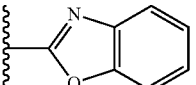 Z-2
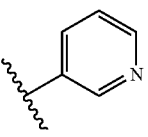 Z-3
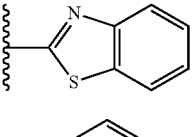 Z-4
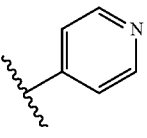 Z-5
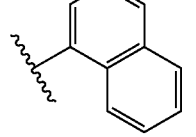 Z-6
-continued
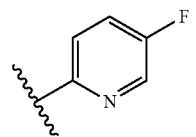 Z-7
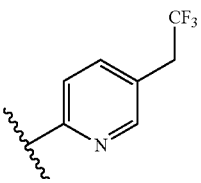 Z-8
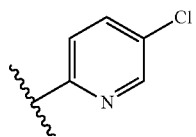 Z-9
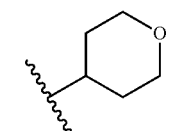 Z-10
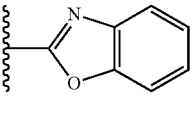 Z-11
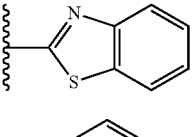 Z-12
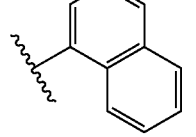 Z-13
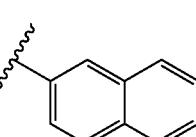 Z-14
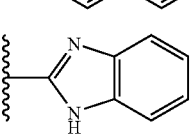 Z-15
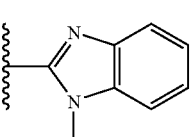 Z-16
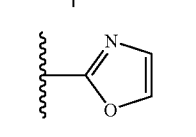 Z-17
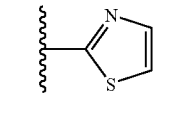 Z-18

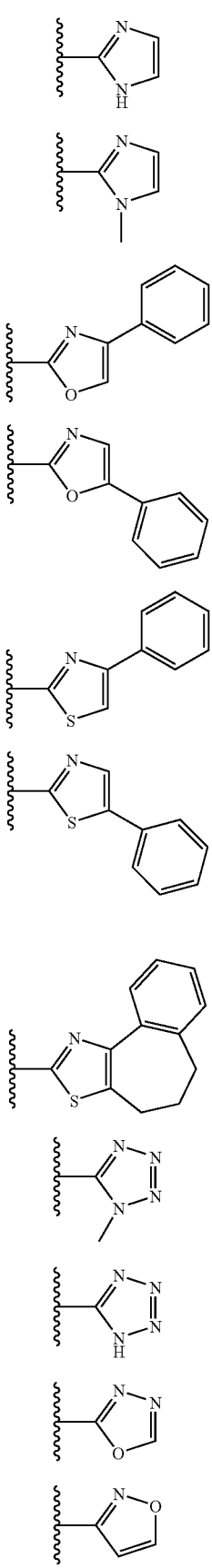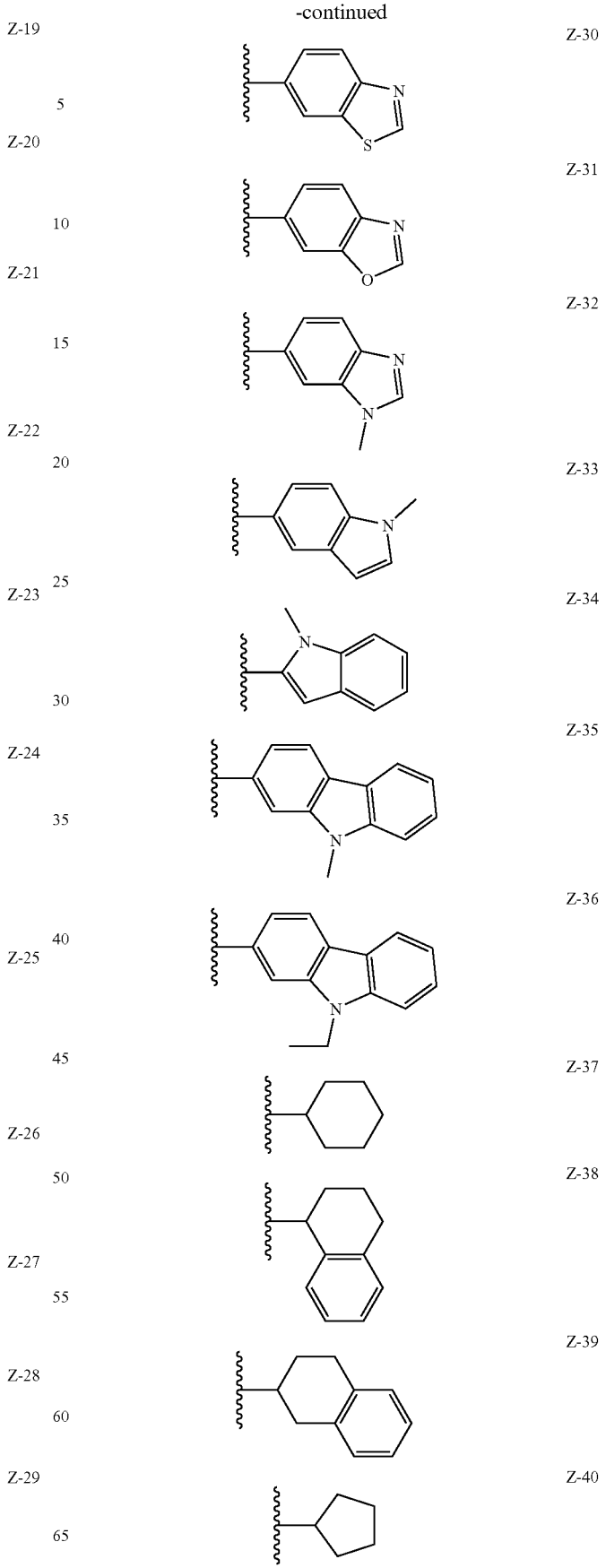

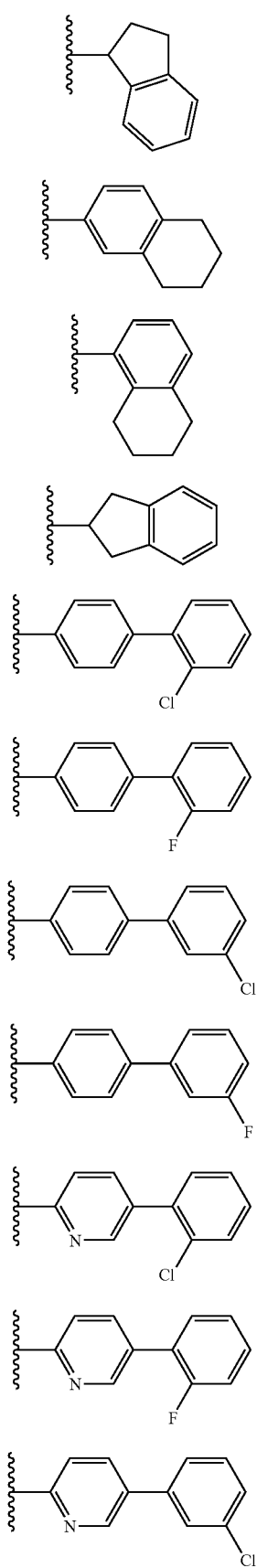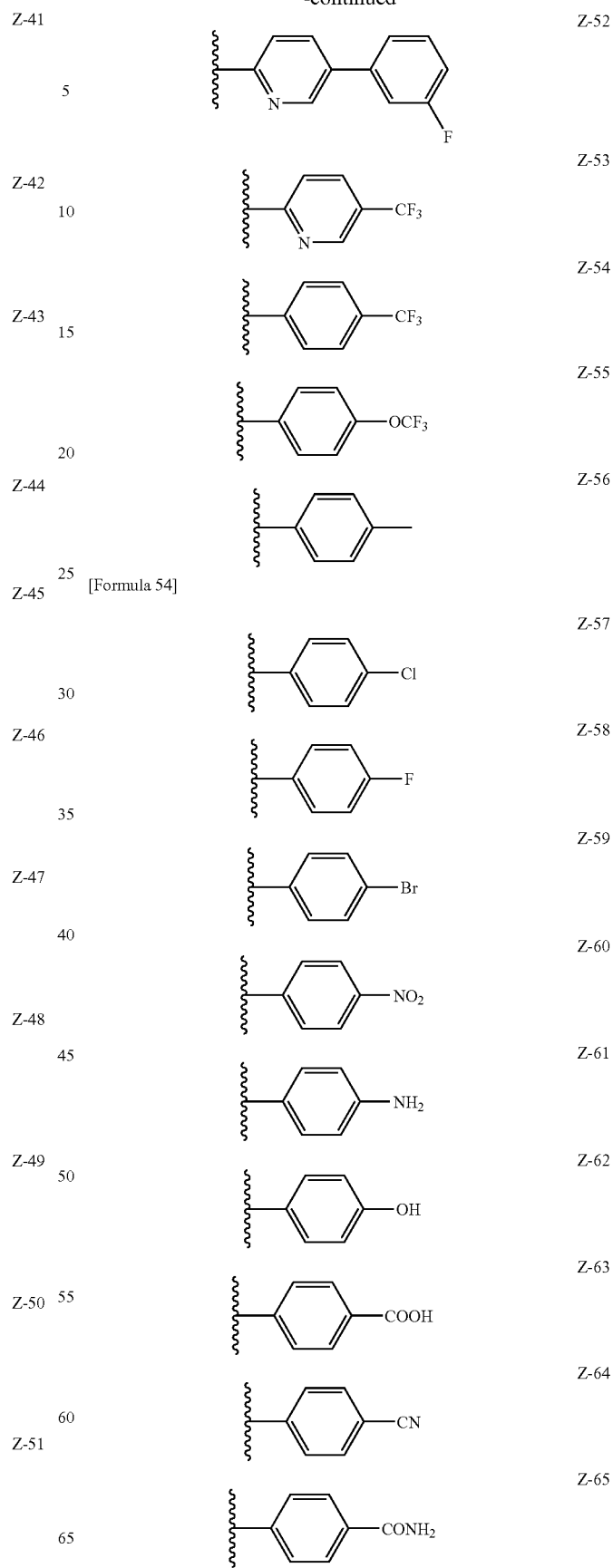

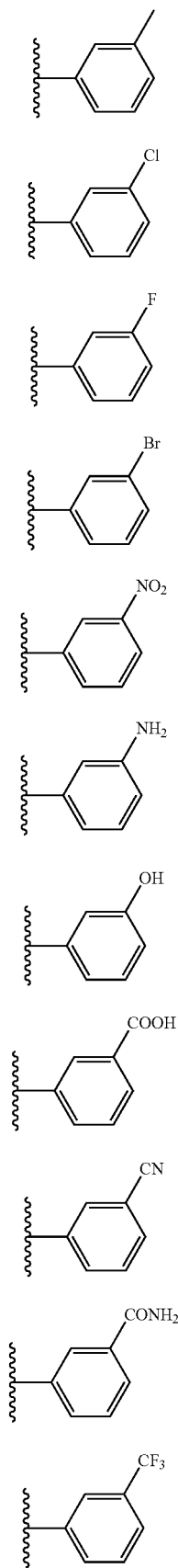
Z-66
Z-67
Z-68
Z-69
Z-70
Z-71
Z-72
Z-73
Z-74
Z-75
Z-76
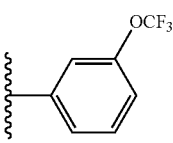
Z-77
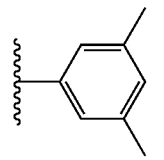
Z-78
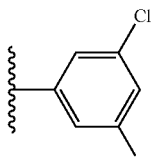
Z-79
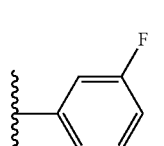
Z-80
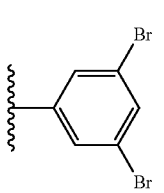
Z-81
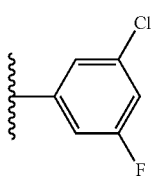
Z-82
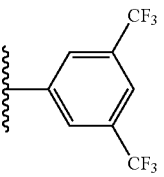
Z-83
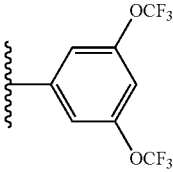
Z-84
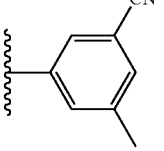
Z-85

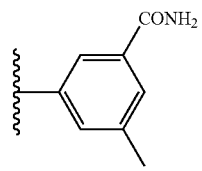 Z-86
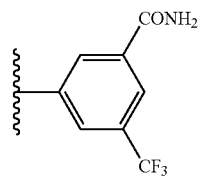 Z-87
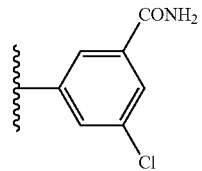 Z-88
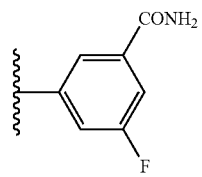 Z-89
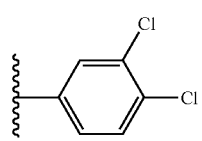 Z-90
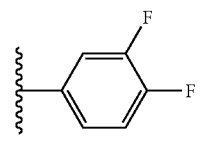 Z-91
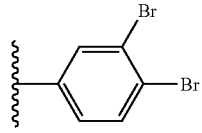 Z-92
[Formula 55]
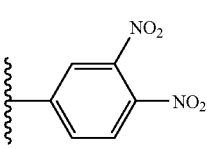 Z-93
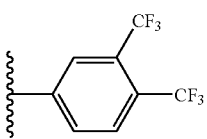 Z-94
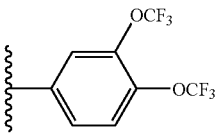 Z-95
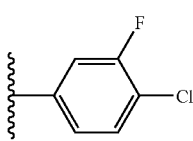 Z-96
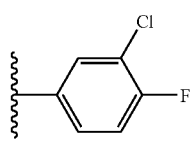 Z-97
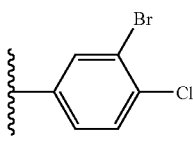 Z-98
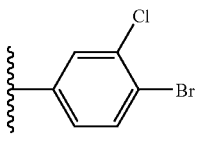 Z-99
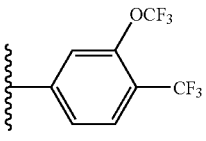 Z-100
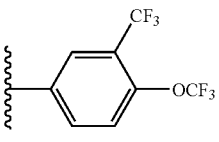 Z-101
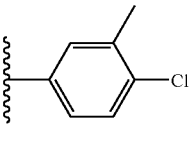 Z-102
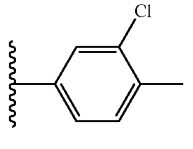 Z-103
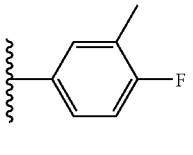 Z-104
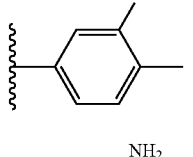 Z-105
Z-106

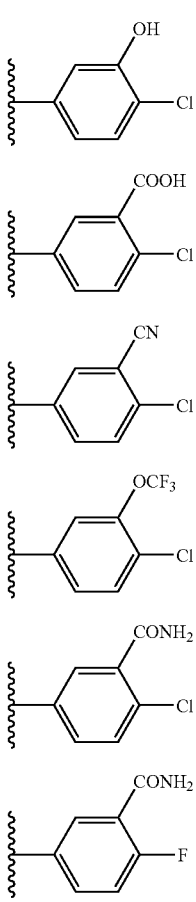

Z-107

Z-108

Z-109

Z-110

Z-111

Z-112

Concretely described below is a compound defined by using the formula (I).

$(R^1, W, R^2, X, Y, R^8, Z) = (R^1-1, W-2, R^2-1, X-1, Y-1, R^8-1, Z-1)$, $(R^1-1, W-2, R^2-1, X-1, Y-1, R^8-1, Z-5)$, $(R^1-1, W-2, R^2-1, X-1, Y-1, R^8-1, Z-6)$, $(R^1-1, W-2, R^2-1, X-1, Y-1, R^8-1, Z-7)$, $(R^1-1, W-2, R^2-1, X-1, Y-1, R^8-1, Z-8)$, $(R^1-1, W-2, R^2-1, X-1, Y-1, R^8-1, Z-9)$, $(R^1-1, W-2, R^2-1, X-1, Y-1, R^8-1, Z-11)$, $(R^1-1, W-2, R^2-1, X-1, Y-1, R^8-1, Z-12)$, $(R^1-1, W-2, R^2-1, X-1, Y-1, R^8-1, Z-13)$, $(R^1-1, W-2, R^2-1, X-1, Y-1, R^8-1, Z-14)$, $(R^1-1, W-2, R^2-1, X-1, Y1, R^8-1, Z-16)$, $(R^1-1, W-2, R^2-1, X-1, Y-1, R^8-1, Z-17)$, $(R^1-1, W-2, R^2-1, X-1, Y-1, R^8-1, Z-18)$, $(R^1-1, W-2, R^2-1, X-1, Y-1, R^8-1, Z-20)$, $(R^1-1, W-2, R^2-1, X-1, Y-1, R^8-1, Z-21)$, $(R^1-1, W-2, R^2-1, X-1, Y-1, R^8-1, Z-22)$, $(R^1-1, W-2, R^2-1, X-1, Y-1, R^8-1, Z-23)$, $(R^1-1, W-2, R^2-1, X-1, Y-1, R^8-1, Z-24)$, $(R^1-1, W-2, R^2-1, X-1, Y-1, R^8-1, Z-25)$, $(R^1-1, W-2, , R^2-1, X-1, Y-1, R^8-1, Z-26)$, $(R^1-1, W-2, R^2-1, X-1, Y-1, R^8-1, Z-28)$, $(R^1-1, W-2, R^2-1, X-1, Y-1 R^8-1, Z-29)$, $(R^1-1, W-2, R^2-1, X-1, Y-1, R^8-1, Z-30)$, $(R^1-1, W-2, R^2-1, X-1, Y-1, R^8-1, Z-31)$, $(R^1-1, W-2, R^2-1, X-1, Y-1, R^8-1, Z-32)$, $(R^1-1, W-2, R^2-1, X-1, Y-1, R^8-1, Z-33)$, $(R^1-1, W-2, R^2-1, X-1, Y-1, R^8-1, Z-34)$, $(R^1-1, W-2, R^2-1, X-1, Y-1, R^8-1, Z-35)$, $(R^1-1, W-2, R^2-1, X-1, Y-1, R^8-1, Z-36)$, $(R^1-1, W-2, R^2-1, X-1, Y-1, R^8-1, Z-38)$, $(R^1-1, W-2, R^2-1, X-1, Y-1, R^8-1, Z-39)$, $(R^1-1, W-2, R^2-1, X-1, Y-1, R^8-1, Z-41)$, $(R^1-1, W-2, R^2-1, X-1, Y-1, R^8-1, Z-42)$, $(R^1-1, W-2, R^2-1, X-1, Y-1, R^8-1, Z-43)$, $(R^1-1, W-2, R^2-1, X-1, Y-1, R^8-1, Z-44)$, $(R^1-1, W-2, R^2-1, X-1, Y-1, R^8-1, Z-45)$, $(R^1-1, W-2, R^2-1, X-1, Y-1, R^8-1, Z-46)$, $(R^1-1, W-2, R^2-1, X-1, Y-1, R^8-1, Z-47)$, $(R^1-1, W-2, R^2-1, X-1, Y-1, R^8-1, Z-48)$, $(R^1-1, W-2, R^2-1, X-1, Y-1, R^8-1, Z-49)$, $(R^1-1, W-2, , R^2-1, X-1, Y-1, R^8-1, Z-50)$, $(R^1-1, W-2, R^2-1, X-1, Y-1, R^8-1, Z-51)$, $(R^1-1, W-2, R^2-1, X-1, Y-1, R^8-1, Z-52)$, $(R^1-1, W-2, R^2-1, X-1, Y-1, R^8-1, Z-53)$, $(R^1-1, W-2, R^2-1, X-1, Y-1, R^8-1, Z-54)$, $(R^1-1, W-2, R^2-1, X-1, Y-1, R^8-1, Z-55)$, $(R^1-1, W-2, R^2-1, X-1, Y-1, R^8-1, Z-57)$, $(R^1-1, W-2, R^2-1, X-1, Y-1, R^8-1, Z-58)$, $(R^1-1, W-2, R^2-1, X-1, Y-1, R^8-1, Z-59)$, $(R^1-1, W-2, R^2-1, X-1, Y-1, R^8-1, Z-60)$, $(R^1-1, W-2, R^2-1, X-1, Y-1, R^8-1, Z-64)$, $(R^1-1, W-2, R^2-1, X-1, Y-1, R^8-1, Z-67)$, $(R^1-1, W-2, R^2-1, X-1, Y-1, R^8-1, Z-68)$, $(R^1-1, W-2, R^2-1, X-1, Y-1, R^8-1, Z-69)$, $(R^1-1, W-2, R^2-1, X-1, Y-1, R^8-1, Z-70)$, $(R^1-1, W-2, R^2-1, X-1, Y-1, R^8-1, Z-74)$, $(R^1-1, W-2, R^2-1, X-1, Y-1, R^8-1, Z-76)$, $(R^1-1, W-2, R^2-1, X-1, Y-1, R^8-1, Z-77)$, $(R^1-1, W-2, R^2-1, X-1, Y-1, R^8-1, Z-79)$, $(R^1-1, W-2, R^2-1, X-1, Y-1, R^8-1, Z-80)$, $(R^1-1, W-2, R^2-1, X-1, Y-1, R^8-1, Z-81)$, $(R^1-1, W-2, R^2-1, X-1, Y-1, R^8-1, Z-82)$, $(R^1-1, W-2, R^2-1, X-1, Y-1, R^8-1, Z-83)$, $(R^1-1, W-2, R^2-1, X-1, Y-1, R^8-1, Z-84)$, $(R^1-1, W-2, R^2-1, X-1, Y-1, R^8-1, Z-90)$, $(R^1-1, W-2, R^2-1, X-1, Y-1, R^8-1, Z-91)$, $(R^1-1, W-2, R^2-1, X-1, Y-1, R^8-1, Z-92)$, $(R^1-1, W-2, R^2-1, X-1, Y-1, R^8-1, Z-94)$, $(R^1-1, W-2, R^2-1, X-1, Y-1, R^8-1, Z-95)$, $(R^1-1, W-2, R^2-1, X-1, Y-1, R^8-1, Z-96)$, $(R^1-1, W-2, R^2-1, X-1, Y-1, R^8-1, Z-97)$, $(R^1-1, W-2, R^2-1, X-1, Y-1, R^8-1, Z-98)$, $(R^1-1, W-2, R^2-1, X-1, Y-1, R^8-1, Z-99)$, $(R^1-1, W-2, R^2-1, X-1, Y-1, R^8-1, Z-100)$, $(R^1-1, W-2, R^2-1, X-1, Y-1, R^8-1, Z-101)$, $(R^1-1, W-2, R^2-1, X-1, Y-1, R^8-1, Z-109)$, $(R^1-1, W-2, R^2-1, X-1, Y-1, R^8-1, Z-110)$, $(R^1-1, W-3, R^2-1, X-1, Y-1, R^8-1, Z-1)$, $(R^1-1, W-3, R^2-1, X-1, Y-1, R^8-1, Z-5)$, $(R^1-1, W-3, R^2-1, X-1, Y-1, R^8-1, Z-6)$, $(R^1-1, W-3, R^2-1, X-1, Y-1, R^8-1, Z-7)$, $(R^1, W-3, R^2-1, X-1, Y-1, R^8-1, Z-8)$, $(R^1-1, W-3, R^2-1, X-1, Y-1, R^8-1, Z-9)$, $(R^1-1, W-3, R^2-1, X-1, Y-1, R^8-1, Z-11)$, $(R^1-1, W-3, R^2-1, X-1, Y-1, R^8-1, Z-12)$, $(R^1-1, W-3, R^2-1, X-1, Y-1, R^8-1, Z-13)$, $(R^1-1, W-3, R^2-1, X-1, Y-1, R^8-1, Z-14)$, $(R^1-1, W-3, R^2-1, X-1, Y-1, R^8-1, Z-16)$, $(R^1-1, W-3, R^2-1, X-1, Y-1, R^8-1, Z-17)$, $(R^1-1, W-3, R^2-1, X-1, Y-1, R^8-1, Z-18)$, $(R^1-1, W-3, R^2-1, X-1, Y-1, R^8-1, Z-20)$, $(R^1-1, W-3, R^2-1, X-1, Y-1, R^8-1, Z-21)$, $(R^1-1, W-3, R^2-1, X-1, Y-1, R^8-1, Z-22)$, $(R^1-1, W-3, R^2-1, X-1, Y-1, R^8-1, Z-23)$, $(R^1-1, W-3, R^2-1, X-1, Y-1, R^8-1, Z-24)$, $(R^1-1, W-3, R^2-1, X-1, Y-1, R^8-1, Z-25)$, $(R^1-1, W-3, R^2-1, X-1, Y-1, R^8-1, Z-26)$, $(R^1-1, W-3, R^2-1, X-1, Y-1, R^8-1, Z-28)$, $(R^1-1, W-3, R^2-1, X-1, Y-1, R^8-1, Z-29)$, $(R^1-1, W-3, R^2-1, X-1, Y-1, R^8-1, Z-30)$, $(R^1-1, W-3, R^2-1, X-1, Y-1, R^8-1, Z-31)$, $(R^1-1, W-3, R^2-1, X-1, Y-1, R^8-1, Z-32)$, $(R^1-1, W-3, R^2-1, X-1, Y-1, R^8-1, Z-33)$, $(R^1-1, W-3, R^2-1, X-1, Y-1, R^8-1, Z-34)$, $(R^1-1, W-3, R^2-1, X-1, Y-1, R^8-1, Z-35)$, $(R^1-1, W-3, R^2-1, X-1, Y-1, R^8-1, Z-36)$, $(R^1-1, W-3, R^2-1, X-1, Y-1, R^8-1, Z-38)$, $(R^1-1, W-3, R^2-1, X-1, Y-1, R^8-1, Z-39)$, $(R^1-1, W-3, R^2-1, X-1, Y-1, R^8-1, Z-41)$, $(R^1-1, W-3, R^2-1, X-1, Y-1, R^8-1, Z-42)$, $(R^1-1, W-3, R^2-1, X-1, Y-1, R^8-1, Z-43)$, $(R^1-1, W-3, R^2-1, X-1, Y-1, R^8-1, Z-44)$, $(R^1-1, W-3, R^2-1, X-1, Y-1, R^8-1, Z-45)$, $(R^1-1, W-3, R^2-1, X-1, Y-1, R^8-1, Z-46)$, $(R^1-1, W-3, R^2-1, X-1, Y-1, R^8-1, Z-47)$, $(R^1-1, W-3, R^2-1, X-1, Y-1, R^8-1, Z-48)$, $(R^1-1, W-3, R^2-1, X-1, Y-1, R^8-1, Z-49)$, $(R^1-1, W-3, R^2-1, X-1, Y-1, R^8-1, Z-50)$, $(R^1-1, W-3, R^2-1, X-1, Y-1, R^8-1, Z-51)$, $(R^1-1, W-3, R^2-1, X-1, Y-1, R^8-1, Z-52)$, $(R^1-1, W-3, R^2-1, X-1, Y-1, R^8-1, Z-53)$, $(R^1-1, W-3, R^2-1, X-1, Y-1, R^8-1, Z-54)$, $(R^1-1, W-3, R^2-1, X-1, Y-1, R^8-1, Z-55)$, $(R^1-1, W-3, R^2-1, X-1, Y-1, R^8-1, Z-57)$, $(R^1-1, W-3, R^2-1, X-1, Y-1, R^8-1, Z-58)$, $(R^1-1, W-3, R^2-1, X-1, Y-1, R^8-1, Z-59)$, $(R^1-1, W-3, R^2-1, X-1, Y-1, R^8-1, Z-60)$, $(R^1-1, W-3, R^2-1, X-1, Y-1, R^8-1, Z-64)$, $(R^1-1, W-3, R^2-1, X-1, Y-1, R^8-1, Z-67)$, $(R^1-1, W-3, R^2-1, X-1, Y-1, R^8-1, Z-68)$, $(R^1-1, W-3, R^2-1, X-1, Y-1, R^8-1, Z-69)$, $(R^1-1, W-3, R^2-1, X-1, Y-1, R^8-1, Z-70)$, $(R^1-1, W-3, R^2-1, X-1, Y-1, R^8-1, Z-74)$, $(R^1-1, W-3, R^2-1, X-1, Y-1, R^8-1, Z-76)$, $(R^1-1, W-3, R^2-1, X-1, Y-1, R^8-1, Z-77)$, $(R^1-1, W-3, R^2-1, X-1, Y-1, R^8-1, Z-79)$, $(R^1-1, W-3, R^2-1, X-1, Y-1, R^8-1, Z-80)$, $(R^1-1, W-3, R^2-1, X-1, Y-1, R^8-1, Z-81)$, $(R^1-1, W-3, R^2-1, X-1, Y-1, R^8-1, Z-82)$, $(R^1-1, W-3, R^2-1, X-1, Y-1, R^8-1, Z-83)$, $(R^1-1, W-3, R^2-1, X-1, Y-1, R^8-1, Z-84)$,

R⁸-1, Z-90), (R1-1, W-3, R²-1, X-1, Y-1, R⁸-1, Z-91), (R¹-1, W-3, R²-1, X-1, Y-1, R⁸-1, Z-92), (R¹-1, W-3, R²-1, X-1, Y-1, R⁸-1, Z-94), (R¹-1, W-3, R²-1, X-1, Y-1, R⁸-1, Z-95), (R¹-1, W-3, R²-1, X-1, Y-1, R⁸-1, Z-96), (R¹-1, W-3, R²-1, X-1, Y-1, R⁸-1, Z-97), (R¹-1, W-3, R²-1, X-1, Y-1, R⁸-1, Z-98), (R¹-1, W-3, R²-1, X-1, Y-1, R⁸-1, Z-99), (R¹-1, W-3, R²-1, X-1, Y-1, R⁸-1,Z-100), (R¹-1, W-3, R²-1, X-1, Y-1, R⁸-1, Z-101), (R¹-1, W-3, R²-1, X-1, Y-1, R⁸-1, Z-109), (R¹-1, W-3, R²-1, X-1, Y-1,Z-110), (R¹-1, W-2, R²-1, X-1, Y-2, R⁸-1, Z-1), (R¹-1, W-2, R²-1, X-1, Y-2, R⁸-1, Z-5), (R¹-1, W-2, R²-1, X-1, Y-2, R⁸-1, Z-6), (R¹-1, W-2, R²-1, X-1, Y-2, R⁸-1, Z-7), (R¹-1, W-2, R²-1, X-1, Y-2, R⁸-1, Z-8), (R¹-1, W-2, R²-1, X-1, Y-2, R⁸-1, Z-9), (R¹-1, W-2, R²-1, X-1, Y-2, R⁸-1, Z-11), (R¹-1, W-2, R²-1, X-1, Y-2, R⁸-1, Z-12), (R¹-1, W-2, R²-1, X-1;Y-2, R⁸-1, Z-13), (R¹-1, W-2, R²-1, X-1, Y-2, R⁸-1, Z-14), (R¹-1, W-2, R²-1, X-1, Y-2, R⁸-1, Z-16), (R¹-1, W-2, R²-1, X-1, Y-2, R⁸-1, Z-17), (R¹-1, W-2, R²-1, X-1, Y-2, R⁸-1, Z-18), (R¹-1, W-2, R²-1, X-1, Y-2, R⁸-1, Z-20), (R¹-1, W-2, R²-1,X-1,Y-2, R⁸-1, Z-21), (R¹-1, W-2, R²-1, X-1, Y-2, R⁸-1, Z-22), (R¹-1, W-2, R²-1, X-1, Y-2, R⁸-1, Z-23), (R¹-1, W-2, R²-1, X-1, Y-2, R⁸-1, Z-24), (R¹-1, W-2, R²-1, X-1, Y-2, R⁸-1, Z-25), (R¹-1, W-2, R²-1, X-1, Y-2, R⁸-1, Z-26), (R¹-1, W-2, R²-1, X-1, Y-2, R⁸-1, Z-28), (R1-1, W-2, R²-1,X-1,Y-2, R⁸-1, Z-29), (R¹-1, W-2, R²-1, X-1, Y-2, R⁸-1, Z-30), (R¹-1, W-2, R²-1, X-1, Y-2, R⁸-1, Z-31), (R¹-1, W-2, R²-1, X-1, Y-2, R⁸-1, Z-32), (R¹-1, W-2, R²-1, X-1, Y-2, R⁸-1, Z-33), (R¹-1, W-2, R²-1, X-1, Y-2, R⁸-1, Z-34), (R¹-1, W-2, R²-1, X-1, Y-2, R⁸-1, Z-35), (R¹-1, W-2, R²-1,X-1,Y-2, R⁸-1, Z-36), (R¹-1, W-2, R²-1, X-1, Y-2, R⁸-1, Z-38), (R¹-1, W-2, R²-1, X-1, Y-2, R⁸-1, Z-39), (R¹-1, W-2, R²-1, X-1, Y-2, R⁸-1, Z-41), (R¹-1, W-2, R²-1, X-1, Y-2, R⁸-1, Z-42), (R¹-1, W-2, R²-1, X-1, Y-2, R⁸-1, Z-43), (R¹-1, W-2, R²-1, X-1, Y-2, R⁸-1, Z-44), (R¹-1, W-2, R²-1,X-1,Y-2, R⁸-1, Z-45), (R¹-1, W-2, R²-1, X-1, Y-2, R⁸-1, Z-46), (R¹-1, W-2, R²-1, X-1, Y-2, R⁸-1, Z-47), (R¹-1, W-2, R²-1, X-1, Y-2, R⁸-1, Z-48), (R¹-1, W-2, R²-1, X-1, Y-2, R⁸-1, Z-49), (R¹-1, W-2, R²-1, X-1, Y-2, R⁸-1, Z-50), (R¹-1, W-2, R²-1, X-1, Y-2, R⁸-1, Z-5 1), (R¹-1, W-2, R²-1, X-1, Y-2, R⁸-1, Z-52), (R¹-1, W-2, R²-1, X-1, Y-2, R⁸-1, Z-53), (R¹-1, W-2, R²-1, X-1, Y-2, R⁸-1, Z-54), (R¹-1, W-2, R²-1, X-1, Y-2, R⁸-1, Z-55), (R¹-1, W-2, R²-1, X-1, Y-2, R⁸-1, Z-57), (R¹-1, W-2, R²-1, X-1, Y-2, R⁸-1, Z-58), (R¹-1, W-2, R²-1,X-1,Y-2, R⁸-1, Z-59), (R¹-1, W-2, R²-1, X-1, Y-2, R⁸-1, Z-60), (R¹-1, W-2, R²-1, X-1, Y-2, R⁸-1, Z-64), (R¹-1, W-2, R²-1, X-1, Y-2, R⁸-1, Z-67), (R¹-1, W-2, R²-1, X-1, Y-2, R⁸-1, Z-68), (R¹-1, W-2, R²-1, X-1, Y-2, R⁸-1, Z-69), (R¹-1, W-2, R²-1, X-1, Y-2, R⁸-1, Z-70), (R¹-1, W-2, R²-1, X-1, Y-2, R⁸-1, Z-74), (R¹-1, W-2, R²-1,X-1,Y-2, R⁸-1, Z-76), (R¹-1, W-2, R²-1, X-1, Y-2, R⁸-1, Z-77), (R¹-1, W-2, R²-1, X-1, Y-2, R⁸-1, Z-79), (R¹-1, W-2, R²-1, X-1, Y-2, R⁸-1, Z-80), (R¹-1, W-2, R²-1, X-1, Y-2, R⁸-1, Z-81), (R¹-1, W-2, R²-1, X-1, Y-2, R⁸-1, Z-82), (R¹-1, W-2, R²-1, X-1, Y-2, R⁸-1, Z-83), (R¹-1, W-2, R²-1,X-1,Y-2, R⁸-1, Z-84), (R¹-1, W-2, R²-1, X-1, Y-2, R⁸-1, Z-90), (R¹-1, W-2, R²-1, X-1, Y-2, R⁸-1, Z-91), (R¹-1, W-2, R²-1, X-1, Y-2, R⁸-1, Z-92), (R¹-1, W-2, R²-1, X-1, Y-2, R⁸-1, Z-94), (R¹-1, W-2, R²-1, X-1, Y-2, R⁸-1, Z-95), (R¹-1, W-2, R²-1, X-1, Y-2, R⁸-1, Z-96), (R¹-1, W-2, R²-1,X-1,Y-2, R⁸-1, Z-97), (R¹-1, W-2, R²-1,X-1,Y-2, R⁸-1,Z-98), (R¹-1, W-2, R²-1, X-1, Y-2, R⁸-1, Z-99), (R¹-1, W-2, R²-1, X-1, Y-2, R⁸-1,Z-100), (R¹-1, W-2, R²-1, X-1, Y-2, R⁸-1, Z-101), (R¹-1, W-2, R²-1, X-1, Y-2, R⁸-1, Z-109), (R¹-1, W-2, R²-1, X-1, Y-2, R⁸-1, Z-110), (R¹-1, W-3, R²-1, X-1, Y-2, R⁸-1, Z-1), (R¹-1, W-3, R²-1, X-1, Y-2, R⁸-1, Z-5), (R¹-1, W-3, R²-1, X-1, Y-2, R⁸-1, Z-6), (R¹-1, W-3, R²-1, X-1, Y-2, R⁸-1, Z-7), (R¹-1, W-3, R²-1, X-1, Y-2, R⁸-1, Z-8), (R¹-1, W-3, R²-1,X-1,Y-2, R⁸-1, Z-9), (R¹-1, W-3, R²-1, X-1, Y-2, R⁸-1, Z-11), (R¹-1, W-3, R²-1, X-1, Y-2, R⁸-1, Z-12), (R¹-1, W-3, R²-1, X-1, Y-2, R⁸-1, Z-13), (R¹-1, W-3, R²-1, X-1, Y-2, R⁸-1, Z-14), (R¹-1, W-3, R²-1, X-1, Y-2, R⁸-1, Z-16), (R¹-1, W-3, R²-1, X-1, Y-2, R⁸-1, Z-17), (R¹-1, W-3, R²-1, X-1, Y-2, R⁸-1, Z-18), (R¹-1, W-3, R²-1, X-1, Y-2, R⁸-1, Z-20), (R¹-1, W-3, R²-1, X-1, Y-2, R⁸-1, Z-21), (R¹-1, W-3, R²-1, X-1, Y-2, R⁸-1, Z-22), (R¹-1, W-3, R²-1, X-1, Y-2, R⁸-1, Z-23), (R¹-1, W-3, R²-1, X-1, Y-2, R⁸-1, Z-24), (R¹-1, W-3, R²-1, X-1, Y-2, R⁸-1, Z-25), (R¹-1, W-3, R²-1, X-1, Y-2, R⁸-1, Z-26), (R¹-1, W-3, R²-1, X-1, Y-2, R⁸-1, Z-28), (R¹-1, W-3, R²-1, X-1, Y-2, R⁸-1, Z-29), (R¹-1, W-3, R²-1, X-1, Y-2, R⁸-1, Z-30), (R¹-1, W-3, R²-1, X-1, Y-2, R⁸-1, Z-31), (R¹-1, W-3, R²-1,X-1,Y-2, R⁸-1, Z-32), (R¹-1, W-3, R²-1, X-1, Y-2, R⁸-1, Z-33), (R¹-1, W-3, R²-1, X-1, Y-2, R⁸-1, Z-34), (R¹-1, W-3, R²-1, X-1, Y-2, R⁸-1, Z-35), (R¹-1, W-3, R²-1, X-1, Y-2, R⁸-1, Z-36), (R¹-1, W-3, R²-1, X-1, Y-2, R⁸-1, Z-38), (R¹-1, W-3, R²-1, X-1, Y-2, R⁸-1, Z-39), (R¹-1, W-3, R²-1, X-1, Y-2, R⁸-1, Z-41), (R¹-1, W-3, R²-1, X-1, Y-2, R⁸-1, Z-42), (R¹-1, W-3, R²-1, X-1, Y-2, R⁸-1, Z-43), (R¹-1, W-3, R²-1, X-1, Y-2, R⁸-1, Z-44), (R¹-1, W-3, R²-1, X-1, Y-2, R⁸-1, Z-45), (R¹-1, W-3, R²-1, X-1, Y-2, R⁸-1, Z-46), (R¹-1, W-3, R²-1, X-1, Y-2, R⁸-1, Z-47), (R¹-1, W-3, R²-1,X-1,Y-2, R⁸-1, Z-48), (R¹-1, W-3, R²-1, X-1, Y-2, R⁸-1, Z-49), (R¹-1, W-3, R²-1, X-1, Y-2, R⁸-1, Z-50), (R¹-1, W-3, R²-1, X-1, Y-2, R⁸-1, Z-51), (R¹-1, W-3, R²-1, X-1, Y-2, R⁸-1, Z-52), (R¹-1, W-3, R²-1, X-1, Y-2, R⁸-1, Z-53), (R¹-1, W-3, R²-1,X-1,Y-2, R⁸-1, Z-54), (R¹-1, W-3, R²-1, X-1, Y-2, R⁸-1, Z-55), (R¹-1, W-3, R²-1, X-1, Y-2, R⁸-1, Z-57), (R¹-1, W-3, R²-1, X-1, Y-2, R⁸-1, Z-58), (R¹-1, W-3, R²-1, X-1, Y-2, R⁸-1, Z-59), (R¹-1, W-3, R²-1, X-1, Y-2, R⁸-1, Z-60), (R¹-1, W-3, R²-1,X-1, Y-2, R⁸-1,Z-64), (R¹-1, W-3, R²-1, X-1, Y-2, R⁸-1,Z-67), (R¹-1, W-3, R²-1, X-1, Y-2, R⁸-1,Z-68), (R¹-1, W-3, R²-1,X-1,Y-2, R⁸-1,Z-69), (R¹-1, W-3, R²-1,X-1,Y-2, R⁸-1, Z-70), (R¹-1, W-3, R²-1,X-1, Y-2, R⁸-1, Z-74), (R¹-1, W-3, R²-1,X-1, Y-2, R⁸-1,Z-76), (R¹-1, W-3, R²-1,X-1,Y-2, R⁸-1,Z-77), (R¹-1, W-3, R²-1, X-1, Y-2, R⁸-1,Z-79), (R¹-1, W-3, R²-1, X-1, Y-2, R⁸-1,Z-80), (R¹-1, W-3, R²-1,X-1,Y-2, R⁸-1,Z-81), (R¹-1, W-3, R²-1,X-1, Y-2, R⁸-1, Z-82), (R¹-1, W-3, R²-1,X-1,Y-2, R⁸-1,Z-83), (R¹-1, W-3, R²-1, X-1, Y-2, R⁸-1, Z-84), (R¹-1, W-3, R²-1, X-1, Y-2, R⁸-1, Z-90), (R¹-1, W-3, R²-1, X-1, Y-2, R⁸-1, Z-91), (R¹-1, W-3, R²-1,X-1,Y-2, R⁸-1, Z-92), (R¹-1, W-3, R²-1, X-1, Y-2, R⁸-1, Z-94), (R¹-1, W-3, R²-1, X-1, Y-2, R⁸-1,Z-95), (R¹-1, W-3, R²-1, X-1, Y-2, R⁸-1, Z-96), (R¹-1, W-3, R²-1, X-1, Y-2, R⁸-1, Z-97), (R¹-1, W-3, R²-1, X-1, Y-2, R⁸-1, Z-98), (R¹-1, W-3, R²-1, X-1, Y-2, R⁸-1, Z-99), (R¹-1, W-3, R²-1, X-1, Y-2, R⁸-1, Z-100), (R¹-1, W-3, R²-1, X-1, Y-2, R⁸-1, Z-101), (R¹-1, W-3, R²-1, X-1, Y-2, R⁸-1, Z-109), (R¹-1, W-3, R²-1, X-1, Y-2, R⁸-1, Z-110)

(R¹-2, W-2, R²-1, X-1, Y-1, R⁸-1, Z-1), (R¹-2, W-2, R²-1, X-1, Y-1, R⁸-1, Z-5), (R¹-2, W-2, R²-1, X-1, Y-1, R⁸-1, Z-6), (R¹-2, W-2, R²-1, X-1, Y-1, R⁸-1, Z-7), (R¹-2, W-2, R²-1, X-1, Y-1, R⁸-1, Z-8), (R¹-2, W-2, R²-1, X-1, Y-1, R⁸-1, Z-9), (R¹-2, W-2, R²-1, X-1, Y-1, R⁸-1,Z-1), (R¹-2, W-2, R²-1, X-1, Y-1, R⁸-1, Z-12), (R¹-2, W-2, R²-1, X-1, Y-1, R⁸-1, Z-13), (R¹-2, W-2, R²-1,X-1,Y-1, R⁸-1, Z-14), (R¹-2, W-2, R²-1, X-1, Y-1, R⁸-1, Z-16), (R¹-2, W-2, R²-1, X-1, Y-1, R⁸-1, Z-17), (R¹-2, W-2, R²-1, X-1, Y-1, R⁸-1, Z-18), (R¹-2, W-2, R²-1, X-1, Y-1, R⁸-1, Z-20), (R¹-2, W-2, R²-1, X-1, Y-1, R⁸-1, Z-21), (R¹-2, W-2, R²-1, X-1, Y-1, R⁸-1, Z-22), (R¹-2, W-2, R²-1, X-1, Y-1, R⁸-1, Z-23), (R¹-2, W-2, R²-1, X-1, Y-1, R⁸-1, Z-24), (R¹-2, W-2, R²-1, X-1, Y-1, R⁸-1, Z-25), (R¹-2, W-2, R²-1, X-1, Y-1, R⁸-1, Z-26), (R¹-2, W-2, R²-1, X-1, Y-1, R⁸-1, Z-28), (R¹-2, W-2, R²-1,X-1,Y-1, R⁸-1, Z-29), (R¹-2, W-2, R²-1, X-1, Y-1, R⁸-1, Z-30), (R¹-2, W-2, R²-1, X-1, Y-1, R⁸-1, Z-31), (R¹-2, W-2, R²-1, X-1, Y-1, R⁸-1, Z-32), (R¹-2, W-2, R²-1, X-1, Y-1, R⁸-1, Z-33), (R¹-2, W-2, R²-1, X-1, Y-1, R⁸-1, Z-34), (R¹-2, W-2, R²-1, X-1, Y-1, R⁸-1, Z-35), (R¹-2, W-2, R²-1, X-1, Y-1, R⁸-1, Z-36), (R¹-2, W-2, R²-1, X-1, Y-1, R⁸-1, Z-38), (R¹-2, W-2, R²-1, X-1, Y-1, R⁸-1, Z-39), (R¹-2, W-2, R²-1, X-1, Y-1, R⁸-1, Z-41), (R¹-2, W-2, R²-1, X-1, Y-1, R⁸-1, Z-42), (R¹-2, W-2, R²-1,X-1, Y-1, R⁸-1, Z-43), (R¹-2, W-2, R²-1,X-1, Y-1,

R$^8$-1, Z-44), (R$^1$-2, W-2, R$^2$-1,X-1, Y-1, R$^8$-1, Z-45), (R$^1$-2, W-2, R$^2$-1, X-1,Y-1, R$^8$-1, Z-46), (R$^1$-2, W-2, R$^2$-1, X-1, Y-1, R$^8$-1,Z-47), (R$^1$-2, W-2, R$^2$-1, X-1, Y-1, R$^8$-1, Z-48), (R$^1$-2, W-2, R$^2$-1, X-1, Y-1, R$^8$-1, Z-49), (R$^1$-2, W-2, R$^2$-1, X-1, Y-1, R$^8$-1, Z-50), (R$^1$-2, W-2, R$^2$-1, X-1, Y-1, R$^8$-1, Z-51), (R$^1$-2, W-2, R$^2$-1,X-1, Y-1, R$^8$-1, Z-52), (R$^1$-2, W-2, R$^2$-1, X-1, Y-1, R$^8$-1, Z-53), (R$^1$-2, W-2, R$^2$-1, X-1, Y-1, R$^8$-1,Z-54), (R$^1$-2, W-2, R$^2$-1, X-1, Y-1, R$^8$-1, Z-55), (R$^1$-2, W-2, R$^2$-1, X-1, Y-1, R$^8$-1, Z-57), (R$^1$-2, W-2, R$^2$-1, X-1, Y-1, R$^8$-1, Z-58), (R$^1$-2, W-2, R$^2$-1, X-1, Y-1, R$^8$-1, Z-59), (R$^1$-2, W-2, R$^2$-1, X-1, Y-1, R$^8$-1, Z-60), (R$^1$-2, W-2, R$^2$-1, X-1, Y-1, R$^8$-1, Z-64), (R$^1$-2, W-2, R$^2$-1, X-1, Y-1, R$^8$-1, Z-67), (R$^1$-2, W-2, R$^2$-1, X-1, Y-1, R$^8$-1, Z-68), (R$^1$-2, W-2, R$^2$-1, X-1, Y-1, R$^8$-1, Z-69), (R$^1$-2, W-2, R$^2$-1, X-1, Y-1, R$^8$-1, Z-70), (R$^1$-2, W-2, R$^2$-1X-1, Y-1, R$^8$-1, Z-74), (R$^1$-2, W-2, R$^2$-1,X-1, Y-1, R$^8$-1, Z-76), (R$^1$-2, W-2, R$^2$-1, X-1, Y-1, R$^8$-1, Z-77), (R$^1$-2, W-2, R$^2$-1, X-1, Y-1, R$^8$-1,Z-79), (R$^1$-2, W-2, R$^2$-1, X-1, Y-1, R$^8$-1, Z-80), (R$^1$-2, W-2, R$^2$-1, X-1, Y-1, R$^8$-1, Z-81), (R$^1$-2, W-2, R$^2$-1, X-1, Y-1, R$^8$-1, Z-82), (R$^1$-2, W-2, R$^2$-1, X-1, Y-1, R$^8$-1, Z-83), (R$^1$-2, W-2, R$^2$-1,X-1, Y-1, R$^8$-1, Z-84), (R$^1$-2, W-2, R$^2$-1, X-1, Y-1, R$^8$-1, Z-90), (R$^1$-2, W-2, R$^2$-1, X-1, Y-1, R$^8$-1,Z-91), (R$^1$-2, W-2, R$^2$-1, X-1, Y-1, R$^8$-1, Z-92), (R$^1$-2, W-2, R$^2$-1, X-1, Y-1, R$^8$-1, Z-94), (R$^1$-2, W-2, R$^2$-1,X-1, Y-1, R$^8$-1, Z-95), (R$^1$-2, W-2, R$^2$-1,X-1, Y-1, R$^8$-1, Z-96), (R$^1$-2, W-2, R$^2$-1,X-1, Y-1, R$^8$-1, Z-97), (R$^1$-2, W-2, R$^2$-1, X-1, Y-1, R$^8$-1, Z-98), (R$^1$-2, W-2, R$^2$-1, X-1, Y-1, R$^8$-1,Z-99), (R$^1$-2, W-2, R$^2$-1, X-1, Y-1, R$^8$-1,Z-100), (R$^1$-2, W-2, R$^2$-1, X-1, Y-1, R$^8$-1, Z-101),(R$^1$-2, W-2, R$^2$-1, X-1, Y-1, R$^8$-1, Z-109), (R$^1$-2, W-2, R$^2$-1, X-1, Y-1, R$^8$-1, Z-110), (R$^1$-2, W-3, R$^2$-1,X-1, Y-1, R$^8$-1,Z-1), (R$^1$-2, W-3, R$^2$-1,X-1, Y-1, R$^8$-1, Z-5),(R$^1$-2, W-3, R$^2$-1,X-1, Y-1,R$^8$-1, Z-6), (R$^1$-2, W-3, R$^2$-1, X-1, Y-1, R$^8$-1, Z-7), (R$^1$-2, W-3, R$^2$-1, X-1, Y-1, R$^8$-1, Z-8), (R$^1$-2, W-3, R$^2$-1, X-1, Y-1, R$^8$-1, Z-9), (R$^1$-2, W-3, R$^2$-1, X-1, Y-1, R$^8$-1, Z-11), (R$^1$-2, W-3, R$^2$-1, X-1, Y-1, R$^8$-1, Z-12), (R$^1$-2, W-3, R$^2$-1, X-1, Y-1, R$^8$-1, Z-13), (R$^1$-2, W-3, R$^2$-1, X-1, Y-1, R$^8$-1, Z-14), (R$^1$-2, W-3, R$^2$-1, X-1, Y-1, R$^8$-1,Z-16), (R$^1$-2, W-3, R$^2$-1,X-1,Y-1, R$^8$-1,Z-17), (R$^1$-2, W-3, R$^2$-1, X-1, Y-1, R$^8$-1,Z-18), (R$^1$-2, W-3, R$^2$-1,X-1, Y-1, R$^8$-1,Z-20), (R$^1$-2, W-3, R$^2$-1,X-1, Y-1, R$^8$-1,Z-21), (R$^1$-2, W-3, R$^2$-1,X-1, Y-1, R$^8$-1,Z-22), (R$^1$-2, W-3, R$^2$-1,X-1, Y-1, R$^8$-1,Z-23), (R$^1$-2, W-3, R$^2$-1,X-1,Y-1, R$^8$-1, Z-24), (R$^1$-2, W-3, R$^2$-1, X-1, Y-1, R$^8$-1, Z-25), (R$^1$-2, W-3, R$^2$-1, X-1, Y-1, R$^8$-1, Z-26), (R$^1$-2, W-3, R$^2$-1, X-1, Y-1, R$^8$-1, Z-28), (R$^1$-2, W-3, R$^2$-1, X-1, Y-1, R$^8$-1, Z-29), (R$^1$-2, W-3, R$^2$-1, X-1, Y-1, R$^8$-1, Z-30), (R$^1$-2, W-3, R$^2$-1, X-1, Y-1, R$^8$-1, Z-31), (R$^1$-2, W-3, R$^2$-1, X-1, Y-1, R$^8$-1, Z-32), (R$^1$-2, W-3, R$^2$-1, X-1, Y-1, R$^8$-1, Z-33), (R$^1$-2, W-3, R$^2$-1,X-1, Y-1, R$^8$-1,Z-34), (R$^1$-2, W-3, R$^2$-1, X-1, Y-1, R$^8$-1, Z-35), (R$^1$-2, W-3, R$^2$-1, X-1, Y-1, R$^8$-1, Z-36), (R$^1$-2, W-3, R$^2$-1, X-1, Y-1, R$^8$-1, Z-38), (R$^1$-2, W-3, R$^2$-1, X-1, Y-1, R$^8$-1, Z-39), (R$^1$-2, W-3, R$^2$-1,X-1,Y-1, R$^8$-1, Z-41), (R$^1$-2, W-3, R$^2$-1, X-1, Y-1, R$^8$-1, Z-42), (R$^1$-2, W-3, R$^2$-1, X-1, Y-1, R$^8$-1,Z-43), (R$^1$-2, W-3, R$^2$-1, X-1, Y-1, R$^8$-1, Z-44), (R$^1$-2, W-3, R$^2$-1, X-1, Y-1, R$^8$-1, Z-45), (R$^1$-2, W-3, R$^2$-1, X-1, Y-1, R$^8$-1,Z-46), (R$^1$-2, W-3, R$^2$-1, X-1, Y-1, R$^8$-1, Z-47), (R$^1$-2, W-3, R$^2$-1,X-1, Y-1, R$^8$-1, Z-48), (R$^1$-2, W-3, R$^2$-1, X-1, Y-1, R$^8$-1, Z-49), (R$^1$-2, W-3, R$^2$-1, X-1, Y-1, R$^8$-1,Z-50), (R$^1$-2, W-3, R$^2$-1, X-1, Y-1, R$^8$-1, Z-51), (R$^1$-2, W-3, R$^2$-1, X-1, Y-1, R$^8$-1,Z-52), (R$^1$-2, W-3, R$^2$-1, X-1, Y-1, R$^8$-1, Z-53), (R$^1$-2, W-3, R$^2$-1, X-1, Y-1, R$^8$-1, Z-54), (R$^1$-2, W-3, R$^2$-1,X-1,Y-1, R$^8$-1, Z-55), (R$^1$-2, W-3, R$^2$-1, X-1,Y-1,R$^8$-1, Z-57), (R$^1$-2, W-3, R$^2$-1, X-1, Y-1, R$^8$-1,Z-58), (R$^1$-2, W-3, R$^2$-1, X-1, Y-1, R$^8$-1, Z-59), (R$^1$-2, W-3, R$^2$-1, X-1, Y-1, R$^8$-1, Z-60), (R$^1$-2, W-3, R$^2$-1,X-1, Y-1,R$^8$-1, Z-64), (R$^1$-2, W-3, R$^2$-1,X-1, Y-1, R$^8$-1, Z-67), (R$^1$-2, W-3, R$^2$-1,X-1, Y-1, R$^8$-1, Z-68), (R$^1$-2, W-3, R$^2$-1, X-1, Y-1, R$^8$-1,Z-69), (R$^1$-2, W-3, R$^2$-1, X-1, Y-1, R$^8$-1,Z-70), (R$^1$-2, W-3, R$^2$-1, X-1, Y-1, R$^8$-1, Z-74), (R$^1$-2, W-3, R$^2$-1, X-1, Y-1, R$^8$-1, Z-76), (R$^1$-2, W-3, R$^2$-1, X-1, Y-1, R$^8$-1, Z-77), (R$^1$-2, W-3, R$^2$-1, X-1, Y-1, R$^8$-1, Z-79), (R$^1$-2, W-3, R$^2$-1, X-1, Y-1, R$^8$-1, Z-80), (R$^1$-2, W-3, R$^2$-1, X-1, Y-1, R$^8$-1, Z-81), (R$^1$-2, W-3, R$^2$-1,X-1, Y-1, R$^8$-1,Z-82), (R$^1$-2, W-3, R$^2$-1, X-1, Y-1, R$^8$-1, Z-83), (R$^1$-2, W-3, R$^2$-1, X-1, Y-1, R$^8$-1, Z-84), (R$^1$-2, W-3, R$^2$-1, X-1, Y-1, R$^8$-1, Z-90), (R$^1$-2, W-3, R$^2$-1, X-1, Y-1, R$^8$-1, Z-91), (R$^1$-2, W-3, R$^2$-1,X-1,Y-1, R$^8$-1, Z-92), (R$^1$-2, W-3, R$^2$-1, X-1, Y-1, R$^8$-1, Z-94), (R$^1$-2, W-3, R$^2$-1, X-1, Y-1, R$^8$-1,Z-95), (R$^1$-2, W-3, R$^2$-1, X-1, Y-1, R$^8$-1, Z-96), (R$^1$-2, W-3, R$^2$-1, X-1, Y-1, R$^8$-1, Z-97), (R$^1$-2, W-3, R$^2$-1, X-1, Y-1, R$^8$-1, Z-98), (R$^1$-2, W-3, R$^2$-1,X-1,Y-1, R$^8$-1, Z-99), (R$^1$-2, W-3, R$^2$-1,X-1,Y-1, R$^8$-1, Z-100), (R$^1$-2, W-3, R$^2$-1,X-1, Y-1, R$^8$-1, Z-100), (R$^1$-2, W-3, R$^2$-1, X-1, Y-1, R$^8$-1,Z-109), (R$^1$-2, W-3, R$^2$-1,X-1,Y-1, R$^8$-1, Z-11o), (R$^1$-2, W-2, R$^2$-1, X-1, Y-2, R$^8$-1, Z-1), (R$^1$-2, W-2, R$^2$-1, X-1, Y-2, R$^8$-1, Z-5), (R$^1$-2, W-2, R$^2$-1, X-1, Y-2, R$^8$-1, Z-6), (R$^1$-2, W-2, R$^2$-1,X-1,Y-2, R$^8$-1, Z-7), (R$^1$-2, W-2, R$^2$-1, X-1, Y-2, R$^8$-1,Z-8), (R$^1$-2, W-2, R$^2$-1, X-1, Y-2, R$^8$-1, Z-9), (R$^1$-2, W-2, R$^2$-1, X-1, Y-2, R$^8$-1, Z-11), (R$^1$-2, W-2, R$^2$-1, X-1, Y-2, R$^8$-1, Z-12), (R$^1$-2, W-2, R$^2$-1,X-1, Y-2, R$^8$-1, Z-13), (R$^1$-2, W-2, R$^2$-1, X-1, Y-2, R$^8$-1, Z-14), (R$^1$-2, W-2, R$^2$-1,X-1, Y-2, R$^8$-1,Z-16), (R$^1$-2, W-2, R$^2$-1, X-1, Y-2, R$^8$-1, Z-17), (R$^1$-2, W-2, R$^2$-1, X-1, Y-2, R$^8$-1, Z-18), (R$^1$-2, W-2, R$^2$-1,X-1, Y-2, R$^8$-1, Z-20), (R$^1$-2, W-2, R$^2$-1, X-1, Y-2, R$^8$-1, Z-21), (R$^1$-2, W-2, R$^2$-1,X-1,Y-2, R$^8$-1, Z-22), (R$^1$-2, W-2, R$^2$-1, X-1, Y-2, R$^8$-1, Z-23), (R$^1$-2, W-2, R$^2$-1, X-1, Y-2, R$^8$-1,Z-24), (R$^1$-2, W-2, R$^2$-1, X-1, Y-2, R$^8$-1, Z-25), (R$^1$-2, W-2, R$^2$-1, X-1, Y-2, R$^8$-1, Z-26), (R$^1$-2, W-2, R$^2$-1, X-1, Y-2, R$^8$-1, Z-28), (R$^1$-2, W-2, R$^2$-1,X-1, Y-2, R$^8$-1, Z-29), (R$^1$-2, W-2, R$^2$-1,X-1,Y-2, R$^8$-1, Z-30), (R$^1$-2, W-2, R$^2$-1, X-1, Y-2, R$^8$-1,Z-31), (R$^1$-2, W-2, R$^2$-1, X-1, Y-2, R$^8$-1,Z-32), (R$^1$-2, W-2, R$^2$-1, X-1, Y-2, R$^8$-1, Z-33), (R$^1$-2, W-2, R$^2$-1, X-1, Y-2, R$^8$-1, Z-34), (R$^1$-2, W-2, R$^2$-1, X-1, Y-2, R$^8$-1, Z-35), (R$^1$-2, W-2, R$^2$-1,X-1,Y-2, R$^8$-1,Z-36), (R$^1$-2, W-2, R$^2$-1,X-1,Y-2, R$^8$-1, Z-38), (R$^1$-2, W-2, R$^2$-1, X-1, Y-2, R$^8$-1, Z-39), (R$^1$-2, W-2, R$^2$-1, X-1, Y-2, R$^8$-1,Z-41), (R$^1$-2, W-2, R$^2$-1, X-1, Y-2, R$^8$-1, Z-42), (R$^1$-2, W-2, R$^2$-1, X-1, Y-2, R$^8$-1, Z-43), (R -2, W-2, R$^2$-1, X-1, Y-2, R$^8$-1, Z-44), (R$^1$-2, W-2, R$^2$-1,X-1, Y-2, R$^8$-1,Z-45), (R$^1$-2, W-2, R$^2$-1, X-1, Y-2, R$^8$-1, Z-46), (R$^1$-2, W-2, R$^2$-1, X-1, Y-2, R$^8$-1, Z-47), (R$^1$-2, W-2, R$^2$-1,X-1,Y-2, R$^8$-1,Z-48), (R$^1$-2, W-2, R$^2$-1, X-1, Y-2, R$^8$-1, Z-49), (R$^1$-2, W-2, R$^2$-1, X-1, Y-2, R$^8$-1,Z-50), (R$^1$-2, W-2, R$^2$-1, X-1, Y-2, R$^8$-1, Z-51), (R$^1$-2, W-2, R$^2$-1,X-1, Y-2, R$^8$-1,Z-52), (R$^1$-2, W-2, R$^2$-1, X-1, Y-2, R$^8$-1, Z-53), (R$^1$-2, W-2, R$^2$-1, X-1, Y-2, R$^8$-1, Z-54), (R$^1$-2, W-2, R$^2$-1, X-1, Y-2, R$^8$-1,Z-55), (R$^1$-2, W-2, R$^2$-1, X-1, Y-2, R$^8$-1, Z-57), (R$^1$-2, W-2, R$^2$-1, X-1, Y-2, R$^8$-1, Z-58), (R$^1$-2, W-2, R$^2$-1, X-1, Y-2, R$^8$-1, Z-59), (R$^1$-2, W-2, R$^2$-1, X-1, Y-2, R$^8$-1, Z-60), (R$^1$-2, W-2, R$^2$-1, X-1, Y-2, R$^8$-1,Z-64), (R$^1$-2, W-2, R$^2$-1,X-1, Y-2, R$^8$-1,Z-67), (R$^1$-2, W-2, R$^2$-1,X-1, Y-2, R$^8$-1,Z-68), (R$^1$-2, W-2, R$^2$-1,X-1, Y-2, R$^8$-1,Z-69), (R$^1$-2, W-2, R$^2$-1,X-1, Y-2, R$^8$-1,Z-70), (R$^1$-2, W-2, R$^2$-1,X-1, Y-2, R$^8$-1,Z-74), (R$^1$-2, W-2, R$^2$-1,X-1, Y-2, R$^8$-1,Z-76), (R$^1$-2, W-2, R$^2$-1,X-1,Y-2, R$^8$-1,Z-77), (R$^1$-2, W-2, R$^2$-1,X-1, Y-2, R$^8$-1,Z-79), (R$^1$-2, W-2, R$^2$-1,X-1, Y-2, R$^8$-1,Z-80), (R$^1$-2, W-2, R$^2$-1,X-1, Y-2, R$^8$-1,Z-81), (R$^1$-2, W-2, R$^2$-1, X-1, Y-2, R$^8$-1,Z-82), (R$^1$-2, W-2, R$^2$-1, X-1, Y-2, R$^8$-1, Z-83), (R$^1$-2, W-2, R$^2$-1, X-1, Y-2, R$^8$-1, Z-84), (R$^1$-2, W-2, R$^2$-1,X-1, Y-2, R$^8$-1, Z-90), (R$^1$-2, W-2, R$^2$-1, X-1, Y-2, R$^8$-1, Z-91), (R$^1$-2, W-2, R$^2$-1, X-1, Y-2, R$^8$-1,Z-92), (R$^1$-2, W-2, R$^2$-1, X-1, Y-2, R$^8$-1, Z-94), (R$^1$-2, W-2, R$^2$-1, X-1, Y-2, R$^8$-1, Z-95), (R$^1$-2, W-2, R$^2$-1, X-1, Y-2, R$^8$-1, Z-96), (R$^1$-2, W-2, R$^2$-1, X-1, Y-2, R$^8$-1, Z-97), (R$^1$-2, W-2, R$^2$-1,X-1,Y-2, R$^8$-1, Z-98), (R$^1$-2, W-2, R$^2$-1, X-1, Y-2, R$^8$-1, Z-99), (R$^1$-2, W-2, R$^2$-1, X-1, Y-2, R$^8$-1,Z-100), (R$^1$-2, W-2, R$^2$-1, X-1, Y-2, R$^8$-1, Z-11), (R$^1$-2, W-2, R$^2$-1,X-1, Y-2, R$^8$-1,Z-109), (R$^1$-2, W-2, R$^2$-1,X-1,Y-2, R$^8$-1,Z-110), (R$^1$-2, W-3, R$^2$-1, X-1, Y-2, R$^8$-1, Z-1), (R$^1$-2, W-3, R$^2$-1, X-1, Y-2, R$^8$-1, Z-5), (R$^1$-2, W-3, R$^2$-1, X-1, Y-2, R$^8$-1, Z-6), (R$^1$-2, W-3, R$^2$-1, X-1, Y-2, R$^8$-1, Z-7), (R$^1$-2,

W-3, R²-1, X-1, Y-2, R⁸-1, Z-8), (R¹-2, W-3, R²-1, X-1, Y-2, R⁸-1, Z-9), (R¹-2, W-3, R²-1, X-1, Y-2, R⁸-1, Z-11), (R¹-2, W-3, R²-1,X-1,Y-2,R⁸-1, Z-12), (R¹-2, W-3, R²-1, X-1, Y-2, R⁸-1, Z-13), (R¹-2, W-3, R²-1, X-1, Y-2, R⁸-1, Z-14), (R¹-2, W-3, R²-1, X-1, Y-2, R⁸-1, Z-16), (R¹-2, W-3, R²-1, X-1, Y-2, R⁸-1, Z-17), (R¹-2, W-3, R²-1, X-1, Y-2, R⁸-1, Z-18), (R¹-2, W-3, R²-1,X-1, Y-2, R⁸-1, Z-20), (R¹-2, W-3, R²-1, X-1, Y-2, R⁸-1, Z-21), (R¹-2, W-3, R²-1, X-1, Y-2, R⁸-1,Z-22), (R¹-2, W-3, R²-1, X-1, Y-2, R⁸-1,Z-23), (R¹-2, W-3, R²-1,X-1, Y-2, R⁸-1, Z-24), (R¹-2, W-3, R²-1, X-1, Y-2, R⁸-1, Z-25), (R¹-2, W-3, R²-1, X-1, Y-2, R⁸-1, Z-26), (R¹-2, W-3, R²-1,X-1,Y-2, R⁸-1, Z-28), (R¹-2, W-3, R²-1, X-1, Y-2, R⁸-1, Z-29), (R¹-2, W-3, R²-1, X-1, Y-2, R⁸-1, Z-30), (R¹-2, W-3, R²-1, X-1, Y-2, R⁸-1, Z-31), (R¹-2, W-3, R²-1, X-1, Y-2, R⁸-1, Z-32), (R¹-2, W-3, R²-1, X-1, Y-2, R⁸-1, Z-33), (R¹-2, W-3, R²-1,X-1,Y-2, R⁸-1, Z-34), (R¹-2, W-3, R²-1,X-1,Y-2, R⁸-1, Z-35), (R¹-2, W-3, R²-1, X-1, Y-2, R⁸-1, Z-36), (R¹-2, W-3, R²-1, X-1, Y-2, R⁸-1, Z-38), (R¹-2, W-3, R²-1, X-1, Y-2, R⁸-1, Z-39), (R¹-2, W-3, R²-1, X-1, Y-2, R⁸-1, Z-41), (R¹-2, W-3, R²-1, X-1, Y-2, R⁸-1, Z-42), (R¹-2, W-3, R²-1, X-1, Y-2, R⁸-1, Z-43), (R¹-2, W-3, R²-1, X-1, Y-2, R⁸-1, Z-44), (R¹-2, W-3, R²-1, X-1, Y-2, R⁸-1, Z-45), (R¹-2, W-3, R²-1, X-1, Y-2, R⁸-1, Z-46), (R¹-2, W-3, R²-1, X-1, Y-2, R⁸-1, Z-47), (R¹-2, W-3, R²-1, X-1, Y-2, R⁸-1, Z-48), (R¹-2, W-3, R²-1, X-1, Y-2, R⁸-1, Z-49), (R¹-2, W-3, R²-1, X-1, Y-2, R⁸-1, Z-50), (R¹-2, W-3, R²-1X-1, Y-2, R⁸-1, Z-51), (R¹-2, W-3, R²-1, X-1, Y-2, R⁸-1, Z-52), (R¹-2, W-3, R²-1, X-1, Y-2, R⁸-1,Z-53), (R¹-2, W-3, R²-1, X-1, Y-2, R⁸-1, Z-54), (R¹-2, W-3, R²-1, X-1, Y-2, R⁸-1, Z-55), (R¹-2, W-3, R²-1, X-1, Y-2, R⁸-1, Z-57), (R¹-2, W-3, R²-1, X-1, Y-2, R⁸-1, Z-58), (R¹-2, W-3, R²-1, X-1, Y-2, R⁸-1, Z-59), (R¹-2, W-3, R²-1, X-1, Y-2, R⁸-1, Z-60), (R¹-2, W-3, R²-1, X-1, Y-2, R⁸-1, Z-64), (R¹-2, W-3, R²-1, X-1, Y-2, R⁸-1, Z-67), (R¹-2, W-3, R²-1, X-1, Y-2, R⁸-1, Z-68), (R¹-2, W-3, R²-1, X-1, Y-2, R⁸-1, Z-69), (R¹-2, W-3, R²-1, X-1, Y-2, R⁸-1, Z-70), (R¹-2, W-3, R²-1,X-1, Y-2, R⁸-1, Z-74), (R¹-2, W-3, R²-1, X-1, Y-2, R⁸-1, Z-76), (R¹-2, W-3, R²-1, X-1, Y-2, R⁸-1,Z-77), (R¹-2, W-3, R²-1, X-1, Y-2, R⁸-1, Z-79), (R¹-2, W-3, R²-1,X-1,Y-2, R⁸-1, Z-80), (R¹-2, W-3, R²-1, X-1, Y-2, R⁸-1, Z-81), (R¹-2, W-3, R²-1,X-1, Y-2, R⁸-1, Z-82), (R¹-2, W-3, R²-1, X-1, Y-2, R⁸-1, Z-83), (R¹-2, W-3, R²-1, X-1, Y-2, R⁸-1, Z-84), (R¹-2, W-3, R²-1, X-1, Y-2, R⁸-1, Z-90), (R¹-2, W-3, R²-1, X-1, Y-2, R⁸-1, Z-91), (R¹-2, W-3, R²-1, X-1, Y-2, R⁸-1, Z-92), (R¹-2, W-3, R²-1, X-1, Y-2, R⁸-1, Z-94), (R¹-2, W-3, R²-1,X-1,Y-2, R⁸-1, Z-95), (R¹-2, W-3, R²-1,X-1,Y-2, R⁸-1, Z-96), (R¹-2, W-3, R²-1, X-1, Y-2, R⁸-1, Z-97), (R¹-2, W-3, R²-1, X-1, Y-2, R⁸-1,Z-98), (R¹-2, W-3, R²-1, X-1, Y-2, R⁸-1, Z-99), (R¹-2, W-3, R²-1, X-1, Y-2, R⁸-1, Z-100), (R¹-2, W-3, R²-1, X-1, Y-2, R⁸-1,Z-101), (R¹-2, W-3, R²-1, X-1, Y-2, R⁸-1,Z-109), (R¹-2, W-3, R²-1,X-1,Y-2, R⁸-1,Z-110)

(R¹-5, W-2, R²-1, X-1, Y-1, R⁸-1, Z-1), (R¹-5, W-2, R²-1, X-1, Y-1, R⁸-1, Z-5), (R¹-5, W-2, R²-1, X-1, Y-1, R⁸-1, Z-6), (R¹-5, W-2, R²-1,X-1, Y-1, R⁸-1, Z-7), (R¹-5, W-2, R²-1, X-1, Y-1, R⁸-1, Z-8), (R¹-5, W-2, R²-1, X-1, Y-1, R⁸-1, Z-9), (R¹-5, W-2, R²-1, X-1, Y-1, R⁸-1, Z-11), (R¹-5, W-2, R²-1, X-1, Y-1, R⁸-1, Z-12), (R¹-5, W-2, R²-1, X-1, Y-1, R⁸-1, Z-13), (R¹-5, W-2, R²-1, X-1, Y-1, R⁸-1, Z-14), (R¹-5, W-2, R²-1, X-1, Y-1, R⁸-1, Z-16), (R¹-5, W-2, R²-1, X-1, Y-1, R⁸-1, Z-17), (R¹-5, W-2, R²-1, X-1, Y-1, R⁸-1,Z-18), (R¹-5, W-2, R²-1, X-1, Y-1, R⁸-1, Z-20), (R¹-5, W-2, R²-1, X-1, Y-1, R⁸-1, Z-21), (R¹-5, W-2, R²-1, X-1, Y-1, R⁸-1, Z-22), (R¹-5, W-2, R²-1, X-1, Y-1, R⁸-1, Z-23), (R¹-5, W-2, R²-1, X-1, Y-1, R⁸-1, Z-24), (R¹-5, W-2, R²-1,X-1, Y-1, R⁸-1, Z-25), (R¹-5, W-2, R²-1, X-1, Y-1, R⁸-1, Z-26), (R¹-5, W-2, R²-1, X-1, Y-1, R⁸-1, Z-28), (R¹-5, W-2, R²-1, X-1, Y-1, R⁸-1, Z-29), (R¹-5, W-2, R²-1, X-1, Y-1, R⁸-1, Z-30), (R¹-5, W-2, R²-1,X-1, Y-1, R⁸-1, Z-31), (R¹-5, W-2, R²-1, X-1, Y-1, R⁸-1, Z-32), (R¹-5, W-2, R²-1, X-1, Y-1, R⁸-1, Z-33), (R¹-5, W-2, R²-1, X-1, Y-1, R⁸-1, Z-34), (R¹-5, W-2, R²-1, X-1, Y-1, R⁸-1, Z-35), (R¹-5, W-2, R²-1,X-1,Y-1, R⁸-1, Z-36), (R¹-5, W-2, R²-1, X-1, Y-1, R⁸-1, Z-38), (R¹-5, W-2, R²-1, X-1, Y-1, R⁸-1, Z-39), (R¹-5, W-2, R²-1, X-1, Y-1, R⁸-1, Z-41), (R¹-5, W-2, R²-1, X-1, Y-1, R⁸-1, Z-42), (R¹-5, W-2, R²-1, X-1, Y-1, R⁸-1, Z-43), (R¹-5, W-2, R²-1, X-1, Y-1, R⁸-1, Z-44), (R¹-5, W-2, R²-1, X-1, Y-1, R⁸-1, Z-45), (R¹-5, W-2, R²-1, X-1, Y-1, R⁸-1, Z-46), (R¹-5, W-2, R²-1, X-1, Y-1, R⁸-1, Z-47), (R¹-5, W-2, R²-1, X-1, Y-1, R⁸-1, Z-48), (R¹-5, W-2, R²-1, X-1, Y-1, R⁸-1, Z-49), (R¹-5, W-2, R²-1, X-1, Y-1, R⁸-1, Z-50), (R¹-5, W-2, R²-1, X-1, Y-1, R⁸-1, Z-51), (R¹-5, W-2, R²-1,X-1,Y-1, R⁸-1, Z-52), (R¹-5, W-2, R²-1, X-1, Y-1, R⁸-1, Z-53), (R¹-5, W-2, R²-1, X-1, Y-1, R⁸-1, Z-54), (R¹-5, W-2, R²-1, X-1, Y-1, R⁸-1, Z-55), (R¹-5, W-2, R²-1, X-1, Y-1, R⁸-1, Z-57), (R¹-5, W-2, R²-1, X-1, Y-1, R⁸-1, Z-58), (R¹-5, W-2, R²-1,X-1, Y-1, R⁸-1, Z-59), (R¹-5, W-2, R²-1, X-1, Y-1, R⁸-1, Z-60), (R¹-5, W-2, R²-1, X-1, Y-1, R⁸-1, Z-64), (R¹-5, W-2, R²-1, X-1, Y-1, R⁸-1, Z-67), (R¹-5, W-2, R²-1, X-1, Y-1, R⁸-1, Z-68), (R¹-5, W-2, R²-1, X-1, Y-1, R⁸-1, Z-69), (R¹-5, W-2, R²-1, X-1, Y-1, R⁸-1, Z-70), (R¹-5, W-2, R²-1, X-1, Y-1, R⁸-1, Z-74), (R¹-5, W-2, R²-1,X-1,Y-1, R⁸-1, Z-76), (R¹-5, W-2, R²-1, X-1, Y-1, R⁸-1, Z-77), (R¹-5, W-2, R²-1, X-1, Y-1, R⁸-1, Z-79), (R¹-5, W-2, R²-1, X-1, Y-1, R⁸-1, Z-80), (R¹-5, W-2, R²-1, X-1, Y-1, R⁸-1, Z-81), (R¹-5, W-2, R²-1, X-1, Y-1, R⁸-1, Z-82), (R¹-5, W-2, R²-1, X-1, Y-1, R⁸-1, Z-83), (R¹-5, W-2, R²-1, X-1, Y-1, R⁸-1, Z-84), (R¹-5, W-2, R²-1, X-1, Y-1, R⁸-1, Z-90), (R¹-5, W-2, R²-1, X-1, Y-1, R⁸-1, Z-91), (R¹-5, W-2, R²-1, X-1, Y-1, R⁸-1, Z-92), (R¹-5, W-2, R²-1, X-1, Y-1, R⁸-1, Z-94), (R¹-5, W-2, R²-1, X-1, Y-1, R⁸-1, Z-95), (R¹-5, W-2, R²-1, X-1, Y-1, R⁸-1, Z-96), (R¹-5, W-2, R²-1, X-1, Y-1, R⁸-1, Z-97), (R¹-5, W-2, R²-1, X-1, Y-1, R⁸-1, Z-98), (R¹-5, W-2, R²-1, X-1, Y-1, R⁸-1, Z-99), (R¹-5, W-2, R²-1, X-1, Y-1, R⁸-1, Z-100), (R¹-5, W-2, R²-1, X-1, Y-1, R⁸-1, Z-101), (R¹-5, W-2, R²-1, X-1, Y-1, R⁸-1, Z-109), (R³-5, W-2, R²-1, X-1, Y-1, R⁸-1, Z-110), (R¹-5, W-3, R²-1,X-1,Y-1, R⁸-1, Z-1), (R¹-5, W-3, R²-1, X-1, Y-1, R⁸-1, Z-5), (R¹-5, W-3, R²-1, X-1, Y-1, R⁸-1, Z-6), (R¹-5, W-3, R²-1, X-1, Y-1, R⁸-1, Z-7), (R¹-5, W-3, R²-1, X-1, Y-1, R⁸-1, Z-8), (R¹-5, W-3, R²-1, X-1, Y-1, R⁸-1, Z-9), (R¹-5, W-3, R²-1, X-1, Y-1, R⁸-1, Z-11), (R¹-5, W-3, R²-1, X-1, Y-1, R⁸-1, Z-12), (R¹-5, W-3, R²-1, X-1, Y-1, R⁸-1, Z-13), (R¹-5, W-3, R²-1, X-1, Y-1, R⁸-1, Z-14), (R¹-5, W-3, R²-1, X-1, Y-1, R⁸-1, Z-16), (R¹-5, W-3, R²-1, X-1,Y-1,R⁸-1, Z-17), (R¹-5, W-3, R²-1, X-1, Y-1, R⁸-1, Z-18), (R¹-5, W-3, R²-1, X-1, Y-1, R⁸-1, Z-20), (R¹-5, W-3, R²-1, X-1, Y-1, R⁸-1, Z-21), (R¹-5, W-3, R²-1, X-1, Y-1, R⁸-1, Z-22), (R¹-5, W-3, R²-1, X-1, Y-1, R⁸-1, Z-23), (R¹-5, W-3, R²-1, X-1, Y-1, R⁸-1, Z-24), (R¹-5, W-3, R²-1, X-1, Y-1, R⁸-1, Z-25), (R¹-5, W-3, R²-1, X-1, Y-1, R⁸-1, Z-26), (R¹-5, W-3, R²-1, X-1, Y-1, R⁸-1, Z-28), (R¹-5, W-3, R²-1, X-1, Y-1, R⁸-1, Z-29), (R¹-5, W-3, R²-1, X-1, Y-1, R⁸-1, Z-30), (R¹-5, W-3, R²-1, X-1, Y-1, R⁸-1, Z-31), (R¹-5, W-3, R²-1, X-1, Y-1, R⁸-1, Z-32), (R¹-5, W-3, R²-1, X-1, Y-1, R⁸-1, Z-33), (R¹-5, W-3, R²-1, X-1, Y-1, R⁸-1, Z-34), (R¹-5, W-3, R²-1, X-1, Y-1, R⁸-1, Z-35), (R¹-5, W-3, R²-1, X-1, Y-1, R⁸-1, Z-36), (R¹-5, W-3, R²-1, X-1, Y-1, R⁸-1, Z-38), (R¹-5, W-3, R²-1, X-1, Y-1, R⁸-1, Z-39), (R¹-5, W-3, R²-1, X-1, Y-1, R⁸-1, Z-41), (R¹-5, W-3, R²-1, X-1, Y-1, R⁸-1, Z-42), (R¹-5, W-3, R²-1, X-1, Y-1, R⁸-1, Z-43), (R¹-5, W-3, R²-1, X-1, Y-1, R⁸-1, Z-44), (R¹-5, W-3, R²-1, X-1, Y-1, R⁸-1,Z-45), (R¹-5, W-3, R²-1,X-1,Y-1, R⁸-1, Z-46), (R¹-5, W-3, R²-1, X-1, Y-1, R⁸-1, Z-47), (R¹-5, W-3, R²-1, X-1, Y-1, R⁸-1, Z-48), (R¹-5, W-3, R²-1, X-1, Y-1, R⁸-1, Z-49), (R¹-5, W-3, R²-1, X-1, Y-1, R⁸-1, Z-50), (R¹-5, W-3, R²-1, X-1, Y-1, R⁸-1, Z-51), (R¹-5, W-3, R²-1, X-1, Y-1, R⁸-1, Z-52), (R¹-5, W-3, R²-1, X-1, Y-1, R⁸-1, Z-53), (R¹-5, W-3, R²-1, X-1, Y-1, R⁸-1, Z-54), (R¹-5, W-3, R²-1, X-1, Y-1, R⁸-1, Z-55), (R¹-5, W-3, R²-1, X-1, Y-1, R⁸-1, Z-57), (R¹-5, W-3, R²-1, X-1, Y-1, R⁸-1, Z-58), (R¹-5, W-3, R²-1, X-1, Y-1, R⁸-1, Z-59), (R¹-5, W-3, R²-1,X-1, Y-1, R⁸-1, Z-60), (R¹-5, W-3, R²-1,X-1, Y-1, $R^8$-1,Z-64), ($R^1$-5, W-3, $R^2$-1,X-1, Y-1, $R^8$-1,Z-67), ($R^1$-5, W-3, $R^2$-1,X-1,Y-1, $R^8$-1,Z-68), ($R^1$-5, W-3, $R^2$-1,X-1, Y-1, $R^8$-1,Z-69), ($R^1$-5, W-3, $R^2$-1,X-1, Y-1, $R^8$-1,Z-70), ($R^1$-5, W-3, $R^2$-1,X-1, Y-1, $R^8$-1,Z-74), ($R^1$-5, W-3, $R^2$-1,X-1, Y-1, $R^8$-1,Z-76), ($R^1$-5, W-3, $R^2$-1,X-1, Y-1, $R^8$-1,Z-77), ($R^1$-5, W-3, $R^2$-1,X-1,Y-1, $R^8$-1,Z-79), ($R^1$-5, W-3, $R^2$-1,X-1,Y-1, $R^8$-1,Z-80), ($R^1$-5, W-3, $R^2$-1,X-1, Y-1, $R^8$-1,Z-81), ($R^1$-5, W-3, $R^2$-1,X-1, Y-1, $R^8$-1,Z-82), ($R^1$-5, W-3, $R^2$-1,X-1, Y-1, $R^8$-1,Z-83), ($R^1$-5, W-3, $R^2$-1,X-1, Y-1, $R^8$-1,Z-84), ($R^1$-5, W-3, $R^2$-1,X-1, Y-1, $R^8$-1,Z-90), ($R^1$-5, W-3, $R^2$-1,X-1, Y-1, $R^8$-1,Z-91), ($R^1$-5, W-3, $R^2$-1,X-1,Y-1, $R^8$-1,Z-92), ($R^1$-5, W-3, $R^2$-1, X-1, Y-1, $R^8$-1,Z-94), ($R^1$-5, W-3, $R^2$-1,X-1, Y-1, $R^8$-1,Z-95), ($R^1$-5, W-3, $R^2$-1,X-1, Y-1, $R^8$-1,Z-96), ($R^1$-5, W-3, $R^2$-1,X-1, Y-1, $R^8$-1,Z-97), ($R^1$-5, W-3, $R^2$-1,X-1, Y-1, $R^8$-1,Z-98), ($R^1$-5, W-3, $R^2$-1,X-1, Y-1, $R^8$-1,Z-99), ($R^1$-5, W-3, $R^2$-1,X-1,Y-1, $R^8$-1,Z-100), ($R^1$-5, W-3, $R^2$-1,X-1, Y-1, $R^8$-1,Z-101), ($R^1$-5, W-3, $R^2$-1,X-1, Y-1, $R^8$-1,Z-109), ($R^1$-5, W-3, $R^2$-1,X-1, Y-1, $R^8$-1,Z-110), ($R^1$-5, W-2, $R^2$-1,X-1, Y-2, $R^8$-1,Z-1), ($R^1$-5, W-2, $R^2$-1,X-1, Y-2, $R^8$-1,Z-5), ($R^1$-5, W-2, $R^2$-1,X-1, Y-2, $R^8$-1,Z-6), ($R^1$-5, W-2, $R^2$-1,X-1,Y-2, $R^8$-1,Z-7), ($R^1$-5, W-2, $R^2$-1,X-1, Y-2, $R^8$-1,Z-8), ($R^1$-5, W-2, $R^2$-1, X-1, Y-2, $R^8$-1,Z-9), ($R^1$-5, W-2, $R^2$-1,X-1, Y-2, $R^8$-1,Z-11), ($R^1$-5, W-2, $R^2$-1,X-1, Y-2, $R^8$-1,Z-12), ($R^1$-5, W-2, $R^2$-1,X-1, Y-2, $R^8$-1, Z-13), ($R^1$-5, W-2, $R^2$-1, X-1, Y-2, $R^8$-1, Z-14), ($R^1$-5, W-2, $R^2$-1, X-1, Y-2, $R^8$-1, Z-16), ($R^1$-5, W-2, $R^2$-1, X-1, Y-2, $R^8$-1, Z-17), ($R^1$-5, W-2, $R^2$-1, X-1, Y-2, $R^8$-1, Z-18), ($R^1$-5, W-2, $R^2$-1, X-1, Y-2, $R^8$-1, Z-20), ($R^1$-5, W-2, $R^2$-1, X-1, Y-2, $R^8$-1, Z-21), ($R^1$-5, W-2, $R^2$-1,X-1,Y-2, $R^8$-1, Z-22), ($R^1$-5, W-2, $R^2$-1, X-1, Y-2, $R^8$-1, Z-23), ($R^1$-5, W-2, $R^2$-1, X-1, Y-2, $R^8$-1,Z-24), ($R^1$-5, W-2, $R^2$-1, X-1, Y-2, $R^8$-1, Z-25), ($R^1$-5, W-2, $R^2$-1, X-1, Y-2, $R^8$-1, Z-26), ($R^1$-5, W-2, $R^2$-1, X-1, Y-2, $R^8$-1, Z-28), ($R^1$-5, W-2, $R^2$-1,X-1,Y-2, $R^8$-1, Z-29), ($R^1$-5, W-2, $R^2$-1,X-1,Y-2, $R^8$-1, Z-30), ($R^1$-5, W-2, $R^2$-1, X-1, Y-2, $R^8$-1, Z-31), ($R^1$-5, W-2, $R^2$-1, X-1, Y-2, $R^8$-1, Z-32), ($R^1$-5, W-2, $R^2$-1, X-1, Y-2, $R^8$-1, Z-33), ($R^1$-5, W-2, $R^2$-1, X-1, Y-2, $R^8$-1,Z-34), ($R^1$-5, W-2, $R^2$-1, X-1, Y-2, $R^8$-1, Z-35), ($R^1$-5, W-2, $R^2$-1, X-1, Y-2, $R^8$-1, Z-36), ($R^1$-5, W-2, $R^2$-1,X-1,Y-2, $R^8$-1, Z-38), ($R^1$-5, W-2, $R^2$-1, X-1, Y-2, $R^8$-1, Z-39), ($R^1$-5, W-2, $R^2$-1, X-1, Y-2, $R^8$-1,Z-41), ($R^1$-5, W-2, $R^2$-1, X-1, Y-2, $R^8$-1, Z-42), ($R^1$-5, W-2, $R^2$-1, X-1, Y-2, $R^8$-1, Z-43), ($R^1$-5, W-2, $R^2$-1, X-1, Y-2, $R^8$-1, Z-44), ($R^1$-5, W-2, $R^2$-1, X-1, Y-2, $R^8$-1, Z-45), ($R^1$-5, W-2, $R^2$-1,X-1,Y-2, $R^8$-1, Z-46), ($R^1$-5, W-2, $R^2$-1, X-1, Y-2, $R^8$-1, Z-47), ($R^1$-5, W-2, $R^2$-1, X-1, Y-2, $R^8$-1, Z-48), ($R^1$-5, W-2, $R^2$-1, X-1, Y-2, $R^8$-1, Z-49), ($R^1$-5, W-2, $R^2$-1, X-1, Y-2, $R^8$-1, Z-50), ($R^1$-5, W-2, $R^2$-1, X-1, Y-2, $R^8$-1, Z-51), ($R^1$-5, W-2, $R^2$-1, X-1, Y-2, $R^8$-1, Z-52), ($R^1$-5, W-2, $R^2$-1,X-1,Y-2, $R^8$-1, Z-53), ($R^1$-5, W-2, $R^2$-1, X-1, Y-2, $R^8$-1,Z-54), ($R^1$-5, W-2, $R^2$-1, X-1, Y-2, $R^8$-1, Z-55), ($R^1$-5, W-2, $R^2$-1, X-1, Y-2, $R^8$-1, Z-57), ($R^1$-5, W-2, $R^2$-1, X-1, Y-2, $R^8$-1, Z-58), ($R^1$-5, W-2, $R^2$-1, X-1, Y-2, $R^8$-1, Z-59), ($R^1$-5, W-2, $R^2$-1,X-1, Y-2, $R^8$-1, Z-60), ($R^1$-5, W-2, $R^2$-1,X-1,Y-2, $R^8$-1, Z-64), ($R^1$-5, W-2, $R^2$-1, X-1, Y-2, $R^8$-1, Z-67), ($R^1$-5, W-2, $R^2$-1, X-1, Y-2, $R^8$-1,Z-68), ($R^1$-5, W-2, $R^2$-1, X-1, Y-2, $R^8$-1, Z-69), ($R^1$-5, W-2, $R^2$-1, X-1, Y-2, $R^8$-1, Z-70), ($R^1$-5, W-2, $R^2$-1, X-1, Y-2, $R^8$-1, Z-74), ($R^1$-5, W-2, $R^2$-1,X-1, Y-2, $R^8$-1, Z-76), ($R^1$-5, W-2, $R^2$-1,X-1,Y-2, $R^8$-1, Z-77), ($R^1$-5, W-2, $R^2$-1, X-1, Y-2, $R^8$-1,Z-79), ($R^1$-5, W-2, $R^2$-1, X-1, Y-2, $R^8$-1,Z-80), ($R^1$-5, W-2, $R^2$-1, X-1, Y-2, $R^8$-1, Z-81), ($R^1$-5, W-2, $R^2$-1, X-1, Y-2, $R^8$-1, Z-82), ($R^1$-5, W-2, $R^2$-1, X-1, Y-2, $R^8$-1, Z-83), ($R^1$-5, W-2, $R^2$-1,X-1,Y-2, $R^8$-1, Z-84), ($R^1$-5, W-2, $R^2$-1,X-1,Y-2, $R^8$-1, Z-90), ($R^1$-5, W-2, $R^2$-1, X-1, Y-2, $R^8$-1, Z-91), ($R^1$-5, W-2, $R^2$-1, X-1, Y-2, $R^8$-1,Z-92), ($R^1$-5, W-2, $R^2$-1, X-1, Y-2, $R^8$-1, Z-94), ($R^1$-5, W-2, $R^2$-1, X-1, Y-2, $R^8$-1, Z-95), ($R^1$-5, W-2, $R^2$-1, X-1, Y-2, $R^8$-1, Z-96), ($R^1$-5, W-2, $R^2$-1, X-1, Y-2, $R^8$-1, Z-97), ($R^1$-5, W-2, $R^2$-1,X-1,Y-2, $R^8$-1, Z-98), ($R^1$-5, W-2, $R^2$-1, X-1, Y-2, $R^8$-1, Z-99), ($R^1$-5, W-2, $R^2$-1, X-1, Y-2, $R^8$-1, Z-100), ($R^1$-5, W-2, $R^2$-1, X-1, Y-2, $R^8$-1, Z-101), ($R^1$-5, W-2, $R^2$-1, X-1, Y-2, $R^8$-1, Z-109), ($R^1$-5, W-2, $R^2$-1, X-1, Y-2, $R^8$-1, Z-110), ($R^1$-5, W-3, $R^2$-1, X-1, Y-2, $R^8$-1, Z-1), ($R^1$-5, W-3, $R^2$-1,X-1, Y-2, $R^8$-1, Z-5), ($R^1$-5, W-3, $R^2$-1, X-1, Y-2, $R^8$-1,Z-6), ($R^1$-5, W-3, $R^2$-1, X-1, Y-2, $R^8$-1, Z-7), ($R^1$-5, W-3, $R^2$-1, X-1, Y-2, $R^8$-1, Z-8), ($R^1$-5, W-3, $R^2$-1, X-1, Y-2, $R^8$-1, Z-9), ($R^1$-5, W-3, $R^2$-1, X-1, Y-2, $R^8$-1, Z-11), ($R^1$-5, W-3, $R^2$-1,X-1,Y-2, $R^8$-1, Z-12), ($R^1$-5, W-3, $R^2$-1, X-1, Y-2, $R^8$-1, Z-13), ($R^1$-5, W-3, $R^2$-1, X-1, Y-2, $R^8$-1, Z-14), ($R^1$-5, W-3, $R^2$-1, X-1, Y-2, $R^8$-1, Z-16), ($R^1$-5, W-3, $R^2$-1, X-1, Y-2, $R^8$-1, Z-17), ($R^1$-5, W-3, $R^2$-1, X-1, Y-2, $R^8$-1, Z-18), ($R^1$-5, W-3, $R^2$-1, X-1, Y-2, $R^8$-1, Z-20), ($R^1$-5, W-3, $R^2$-1, X-1, Y-2, $R^8$-1,Z-21), ($R^1$-5, W-3, $R^2$-1,X-1, Y-2, $R^8$-1,Z-22), ($R^1$-5, W-3, $R^2$-1, X-1, Y-2, $R^8$-1, Z-23), ($R^1$-5, W-3, $R^2$-1, X-1, Y-2, $R^8$-1, Z-24), ($R^1$-5, W-3, $R^2$-1, X-1, Y-2, $R^8$-1, Z-25), ($R^1$-5, W-3, $R^2$-1, X-1, Y-2, $R^8$-1, Z-26), ($R^1$-5, W-3, $R^2$-1, X-1, Y-2, $R^8$-1, Z-28), ($R^1$-5, W-3, $R^2$-1, X-1, Y-2, $R^8$-1, Z-29), ($R^1$-5, W-3, $R^2$-1, X-1, Y-2, $R^8$-1, Z-30), ($R^1$-5, W-3, $R^2$-1, X-1, Y-2, $R^8$-1, Z-31), ($R^1$-5, W-3, $R^2$-1, X-1, Y-2, $R^8$-1, Z-32), ($R^1$-5, W-3, $R^2$-1, X-1, Y-2, $R^8$-1, Z-33), ($R^1$-5, W-3, $R^2$-1, X-1, Y-2, $R^8$-1, Z-34), ($R^1$-5, W-3, $R^2$-1,X-1,Y-2, $R^8$-1, Z-35), ($R^1$-5, W-3, $R^2$-1, X-1, Y-2, $R^8$-1, Z-36), ($R^1$-5, W-3, $R^2$-1, X-1, Y-2, $R^8$-1, Z-38), ($R^1$-5, W-3, $R^2$-1, X-1, Y-2, $R^8$-1, Z-39), ($R^1$-5, W-3, $R^2$-1, X-1, Y-2, $R^8$-1, Z-41), ($R^1$-5, W-3, $R^2$-1, X-1, Y-2, $R^8$-1, Z-42), ($R^1$-5, W-3, $R^2$-1, X-1, Y-2, $R^8$-1, Z-43), ($R^1$-5, W-3, $R^2$-1, X-1, Y-2, $R^8$-1, Z-44), ($R^1$-5, W-3, $R^2$-1,X-1, Y-2, $R^8$-1, Z-45), ($R^1$-5, W-3, $R^2$-1, X-1, Y-2, $R^8$-1, Z-46), ($R^1$-5, W-3, $R^2$-1, X-1, Y-2, $R^8$-1, Z-47), ($R^1$-5, W-3, $R^2$-1, X-1, Y-2, $R^8$-1, Z-48), ($R^1$-5, W-3, $R^2$-1, X-1, Y-2, $R^8$-1, Z-49), ($R^1$-5, W-3, $R^2$-1, X-1, Y-2, $R^8$-1, Z-50), ($R^1$-5, W-3, $R^2$-1, X-1, Y-2, $R^8$-1, Z-51), ($R^1$-5, W-3, $R^2$-1, X-1, Y-2, $R^8$-1, Z-52), ($R^1$-5, W-3, $R^2$-1, X-1, Y-2, $R^8$-1, Z-53), ($R^1$-5, W-3, $R^2$-1, X-1, Y-2, $R^8$-1, Z-54), ($R^1$-5, W-3, $R^2$-1, X-1, Y-2, $R^8$-1, Z-55), ($R^1$-5, W-3, $R^2$-1, X-1,Y-2, $R^8$-1, Z-57), ($R^1$-5, W-3, $R^2$-1, X-1, Y-2, $R^8$-1, Z-58), ($R^1$-5, W-3, $R^2$-1, X-1, Y-2, $R^8$-1, Z-59), ($R^1$-5, W-3, $R^2$-1, X-1, Y-2, $R^8$-1, Z-60), ($R^1$-5, W-3, $R^2$-1, X-1, Y-2, $R^8$-1, Z-64), ($R^1$-5, W-3, $R^2$-1, X-1, Y-2, $R^8$-1, Z-67), ($R^1$-5, W-3, $R^2$-1, X-1, Y-2, $R^8$-1, Z-68), ($R^1$-5, W-3, $R^2$-1, X-1, Y-2, $R^8$-1, Z-69), ($R^1$-5, W-3, $R^2$-1, X-1, Y-2, $R^8$-1, Z-70), ($R^1$-5, W-3, $R^2$-1, X-1, Y-2, $R^8$-1, Z-74), ($R^1$-5, W-3, $R^2$-1, X-1, Y-2, $R^8$-1, Z-76), ($R^1$-5, W-3, $R^2$-1, X-1, Y-2, $R^8$-1, Z-77), ($R^1$-5, W-3, $R^2$-1, X-1, Y-2, $R^8$-1, Z-79), ($R^1$-5, W-3, $R^2$-1, X-1, Y-2, $R^8$-1, Z-80), ($R^1$-5, W-3, $R^2$-1, X-1, Y-2, $R^8$-1, Z-81), ($R^1$-5, W-3, $R^2$-1, X-1, Y-2, $R^8$-1, Z-82), ($R^1$-5, W-3, $R^2$-1, X-1, Y-2, $R^8$-1, Z-83), ($R^1$-5, W-3, $R^2$-1, X-1, Y-2, $R^8$-1, Z-84), ($R^1$-5, W-3, $R^2$-1, X-1, Y-2, $R^8$-1, Z-90), ($R^1$-5, W-3, $R^2$-1, X-1, Y-2, $R^8$-1, Z-91), ($R^1$-5, W-3, $R^2$-1, X-1, Y-2, $R^8$-1, Z-92), ($R^1$-5, W-3, $R^2$-1, X-1, Y-2, $R^8$-1, Z-94), ($R^1$-5, W-3, $R^2$-1, X-1, Y-2, $R^8$-1, Z-95), ($R^1$-5, W-3, $R^2$-1, X-1, Y-2, $R^8$-1, Z-96), ($R^1$-5, W-3, $R^2$-1, X-1, Y-2, $R^8$-1, Z-97), ($R^1$-5, W-3, $R^2$-1, X-1, Y-2, $R^8$-1, Z-98), ($R^1$-5, W-3, $R^2$-1, X-1, Y-2, $R^8$-1, Z-99), ($R^1$-5, W-3, $R^2$-1, X-1, Y-2, $R^8$-1, Z-100), ($R^1$-5, W-3, $R^2$-1, X-1, Y-2, $R^8$-1, Z-101), ($R^1$-5, W-3, $R^2$-1, X-1, Y-2, $R^8$-1, Z-109), ($R^1$-5, W-3, $R^2$-1, X-1, Y-2, $R^8$-1,Z-110)

A compound represented by the formula (II) wherein Z and $R^8$ are taken together with the adjacent nitrogen atom to form an optionally substituted ring in the formula (I).
Formula (II):

[Formula 56]

$$R^1-W-\underset{R^2}{\underset{|}{N}}-X-Y-B \qquad (II)$$

The abbreviations used for B are as follows:

[Formula 57]

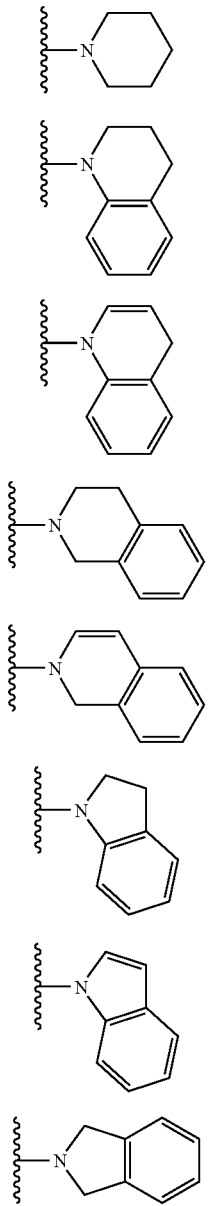

B-1
B-2
B-3
B-4
B-5
B-6
B-7
B-8

Concretely described below is a compound defined by using the formula (II).

$(R^1, W, R^2, X, Y, B) = (R^1\text{-}1, W\text{-}2, R^2\text{-}1, X\text{-}1, Y\text{-}1, B\text{-}1)$, $(R^1\text{-}1, W\text{-}2, R^2\text{-}1, X\text{-}1, Y\text{-}1, B\text{-}2)$, $(R^1\text{-}1, W\text{-}2, R^2\text{-}1, X\text{-}1, Y\text{-}1, B\text{-}3)$, $(R^1\text{-}1, W\text{-}2, R^2\text{-}1, X\text{-}1, Y\text{-}1, B\text{-}4)$, $(R^1\text{-}1, W\text{-}2, R^2\text{-}1, X\text{-}1, Y\text{-}1, B\text{-}5)$, $(R^1\text{-}1, W\text{-}2, R^2\text{-}1, X\text{-}1, Y\text{-}1, B\text{-}7)$, $(R^1\text{-}1, W\text{-}2, R^2\text{-}1, X\text{-}1, Y\text{-}1, B\text{-}8)$, $(R^1\text{-}1, W\text{-}3, R^2\text{-}1, X\text{-}1, Y\text{-}1, B\text{-}1)$, $(R^1\text{-}1, W\text{-}3, R^2\text{-}1, X\text{-}1, Y\text{-}1, B\text{-}2)$, $(R^1\text{-}1, W\text{-}3, R^2\text{-}1, X\text{-}1, Y\text{-}1, B\text{-}3)$, $(R^1\text{-}1, W\text{-}3, R^2\text{-}1, X\text{-}1, Y\text{-}1, B\text{-}4)$, $(R^1\text{-}1, W\text{-}3, R^2\text{-}1, X\text{-}1, Y\text{-}1, B\text{-}5)$, $(R^1\text{-}1, W\text{-}3, R^2\text{-}1, X\text{-}1, Y\text{-}1, B\text{-}6)$, $(R^1\text{-}1, W\text{-}3, R^2\text{-}1, X\text{-}1, Y\text{-}1, B\text{-}7)$, $(R^1\text{-}1, W\text{-}3, R^2\text{-}1, X\text{-}1, Y\text{-}1, B\text{-}8)$, $(R^1\text{-}1, W\text{-}3, R^2\text{-}1, X\text{-}1, Y\text{-}1, B\text{-}1)$, $(R^1\text{-}1, W\text{-}3, R^2\text{-}1, X\text{-}1, Y\text{-}1, B\text{-}2)$, $(R^1\text{-}1, W\text{-}3, R^2\text{-}1, X\text{-}1, Y\text{-}1, B\text{-}3)$, $(R^1\text{-}1, W\text{-}3, R^2\text{-}1, X\text{-}1, Y\text{-}1, B\text{-}4)$, $(R^1\text{-}1, W\text{-}3, R^2\text{-}1, X\text{-}1, Y\text{-}1, B\text{-}5)$, $(R^1\text{-}1, W\text{-}3, R^2\text{-}1, X\text{-}1, Y\text{-}1, B\text{-}6)$, $(R^1\text{-}1, W\text{-}3, R^2\text{-}1, X\text{-}1, Y\text{-}1, B\text{-}7)$, $(R^1\text{-}1, W\text{-}3, R^2\text{-}1, X\text{-}1, Y\text{-}1, B\text{-}8)$, $(R^1\text{-}1, W\text{-}2, R^2\text{-}1, X\text{-}1, Y\text{-}2, B\text{-}1)$, $(R^1\text{-}1, W\text{-}2, R^2\text{-}1, X\text{-}1, Y\text{-}2, B\text{-}2)$, $(R^1\text{-}1, W\text{-}2, R^2\text{-}1, X\text{-}1, Y\text{-}2, B\text{-}3)$, $(R^1\text{-}1, W\text{-}2, R^2\text{-}1, X\text{-}1, Y\text{-}2, B\text{-}4)$, $(R^1\text{-}1, W\text{-}2, R^2\text{-}1, X\text{-}1, Y\text{-}2, B\text{-}5)$, $(R^1\text{-}1, W\text{-}2, R^2\text{-}1, X\text{-}1, Y\text{-}2, B\text{-}6)$, $(R^1\text{-}1, W\text{-}2, R^2\text{-}1, X\text{-}1, Y\text{-}2, B\text{-}7)$, $(R^1\text{-}1, W\text{-}2, R^2\text{-}1, X\text{-}1, Y\text{-}2, B\text{-}8)$, $(R^1\text{-}1, W\text{-}3, R^2\text{-}1, X\text{-}1, Y\text{-}2, B\text{-}1)$, $(R^1\text{-}1, W\text{-}3, R^2\text{-}1, X\text{-}1, Y\text{-}2, B\text{-}2)$, $(R^1\text{-}1, W\text{-}3, R^2\text{-}1, X\text{-}1, Y\text{-}2, B\text{-}3)$, $(R^1\text{-}1, W\text{-}3, R^2\text{-}1, X\text{-}1, Y\text{-}2, B\text{-}4)$, $(R^1\text{-}1, W\text{-}3, R^2\text{-}1, X\text{-}1, Y\text{-}2, B\text{-}5)$, $(R^1\text{-}1, W\text{-}3, R^2\text{-}1, X\text{-}1, Y\text{-}2, B\text{-}6)$, $(R^1\text{-}1, W\text{-}3, R^2\text{-}1, X\text{-}1, Y\text{-}2, B\text{-}7)$, $(R^1\text{-}1, W\text{-}3, R^2\text{-}1, X\text{-}1, Y\text{-}2, B\text{-}8)$, $(R^1\text{-}1, W\text{-}2, R^2\text{-}1, X\text{-}1, Y\text{-}2, B\text{-}1)$, $(R^1\text{-}1, W\text{-}2, R^2\text{-}1, X\text{-}1, Y\text{-}2, B\text{-}2)$, $(R^1\text{-}1, W\text{-}2, R^2\text{-}1, X\text{-}1, Y\text{-}2, B\text{-}3)$, $(R^1\text{-}1, W\text{-}2, R^2\text{-}1, X\text{-}1, Y\text{-}2, B\text{-}4)$, $(R^1\text{-}1, W\text{-}2, R^2\text{-}1, X\text{-}1, Y\text{-}2, B\text{-}5)$, $(R^1\text{-}1, W\text{-}2, R^2\text{-}1, X\text{-}1, Y\text{-}2, B\text{-}6)$, $(R^1\text{-}1, W\text{-}2, R^2\text{-}1, X\text{-}1, Y\text{-}2, B\text{-}7)$, $(R^1\text{-}1, W\text{-}2, R^2\text{-}1, X\text{-}1, Y\text{-}2, B\text{-}8)$, $(R^1\text{-}1, W\text{-}3, R^2\text{-}1, X\text{-}1, Y\text{-}2, B\text{-}1)$, $(R^1\text{-}1, W\text{-}3, R^2\text{-}1, X\text{-}1, Y\text{-}2, B\text{-}2)$, $(R^1\text{-}1, W\text{-}3, R^2\text{-}1, X\text{-}1, Y\text{-}2, B\text{-}3)$, $(R^1\text{-}1, W\text{-}3, R^2\text{-}1, X\text{-}1, Y\text{-}2, B\text{-}4)$, $(R^1\text{-}1, W\text{-}3, R^2\text{-}1, X\text{-}1, Y\text{-}2, B\text{-}5)$, $(R^1\text{-}1, W\text{-}3, R^2\text{-}1, X\text{-}1, Y\text{-}2, B\text{-}6)$, $(R^1\text{-}1, W\text{-}3, R^2\text{-}1, X\text{-}1, Y\text{-}2, B\text{-}7)$, $(R^1\text{-}1, W\text{-}3, R^2\text{-}1, X\text{-}1, Y\text{-}2, B\text{-}8)$ $(R^1\text{-}2, W\text{-}2, R^2\text{-}1, X\text{-}1, Y\text{-}1, B\text{-}1)$, $(R^1\text{-}2, W\text{-}2, R^2\text{-}1, X\text{-}1, Y\text{-}1, B\text{-}2)$, $(R^1\text{-}2, W\text{-}2, R^2\text{-}1, X\text{-}1, Y\text{-}1, B\text{-}3)$, $(R^1\text{-}2, W\text{-}2, R^2\text{-}1, X\text{-}1, Y\text{-}1, B\text{-}4)$, $(R^1\text{-}2, W\text{-}2, R^2\text{-}1, X\text{-}1, Y\text{-}1, B\text{-}5)$, $(R^1\text{-}2, W\text{-}2, R^2\text{-}1, X\text{-}1, Y\text{-}1, B\text{-}7)$, $(R^1\text{-}2, W\text{-}2, R^2\text{-}1, X\text{-}1, Y\text{-}1, B\text{-}8)$, $(R^1\text{-}2, W\text{-}3, R^2\text{-}1, X\text{-}1, Y\text{-}1, B\text{-}1)$, $(R^1\text{-}2, W\text{-}3, R^2\text{-}1, X\text{-}1, Y\text{-}1, B\text{-}2)$, $(R^1\text{-}2, W\text{-}3, R^2\text{-}1, X\text{-}1, Y\text{-}1, B\text{-}3)$, $(R^1\text{-}2, W\text{-}3, R^2\text{-}1, X\text{-}1, Y\text{-}1, B\text{-}4)$, $(R^1\text{-}2, W\text{-}3, R^2\text{-}1, X\text{-}1, Y\text{-}1, B\text{-}5)$, $(R^1\text{-}2, W\text{-}3, R^2\text{-}1, X\text{-}1, Y\text{-}1, B\text{-}6)$, $(R^1\text{-}2, W\text{-}3, R^2\text{-}1, X\text{-}1, Y\text{-}1, B\text{-}7)$, $(R^1\text{-}2, W\text{-}3, R^2\text{-}1, X\text{-}1, Y\text{-}1, B\text{-}8)$, $(R^1\text{-}2, W\text{-}3, R^2\text{-}1, X\text{-}1, Y\text{-}1, B\text{-}1)$, $(R^1\text{-}2, W\text{-}3, R^2\text{-}1, X\text{-}1, Y\text{-}1, B\text{-}2)$, $(R^1\text{-}2, W\text{-}3, R^2\text{-}1, X\text{-}1, Y\text{-}1, B\text{-}3)$, $(R^1\text{-}2, W\text{-}3, R^2\text{-}1, X\text{-}1, Y\text{-}1, B\text{-}4)$, $(R^1\text{-}2, W\text{-}3, R^2\text{-}1, X\text{-}1, Y\text{-}1, B\text{-}5)$, $(R^1\text{-}2, W\text{-}3, R^2\text{-}1, X\text{-}1, Y\text{-}1, B\text{-}6)$, $(R^1\text{-}2, W\text{-}3, R^2\text{-}1, X\text{-}1, Y\text{-}1, B\text{-}7)$, $(R^1\text{-}2, W\text{-}3, R^2\text{-}1, X\text{-}1, Y\text{-}1, B\text{-}8)$, $(R^1\text{-}2, W\text{-}2, R^2\text{-}1, X\text{-}1, Y\text{-}2, B\text{-}1)$, $(R^1\text{-}2, W\text{-}2, R^2\text{-}1, X\text{-}1, Y\text{-}2, B\text{-}2)$, $(R^1\text{-}2, W\text{-}2, R^2\text{-}1, X\text{-}1, Y\text{-}2, B\text{-}3)$, $(R^1\text{-}2, W\text{-}2, R^2\text{-}1, X\text{-}1, Y\text{-}2, B\text{-}4)$, $(R^1\text{-}2, W\text{-}2, R^2\text{-}1, X\text{-}1, Y\text{-}2, B\text{-}5)$, $(R^1\text{-}2, W\text{-}2, R^2\text{-}1, X\text{-}1, Y\text{-}2, B\text{-}6)$, $(R^1\text{-}2, W\text{-}2, R^2\text{-}1, X\text{-}1, Y\text{-}2, B\text{-}7)$, $(R^1\text{-}2, W\text{-}2, R^2\text{-}1, X\text{-}1, Y\text{-}2, B\text{-}8)$, $(R^1\text{-}2, W\text{-}3, R^2\text{-}1, X\text{-}1, Y\text{-}2, B\text{-}1)$, $(R^1\text{-}2, W\text{-}3, R^2\text{-}1, X\text{-}1, Y\text{-}2, B\text{-}2)$, $(R^1\text{-}2, W\text{-}3, R^2\text{-}1, X\text{-}1, Y\text{-}2, B\text{-}3)$, $(R^1\text{-}2, W\text{-}3, R^2\text{-}1, X\text{-}1, Y\text{-}2, B\text{-}4)$, $(R^1\text{-}2, W\text{-}3, R^2\text{-}1, X\text{-}1, Y\text{-}2, B\text{-}5)$, $(R^1\text{-}2, W\text{-}3, R^2\text{-}1, X\text{-}1, Y\text{-}2, B\text{-}6)$, $(R^1\text{-}2, W\text{-}3, R^2\text{-}1, X\text{-}1, Y\text{-}2, B\text{-}7)$, $(R^1\text{-}2, W\text{-}3, R^2\text{-}1, X\text{-}1, Y\text{-}2, B\text{-}8)$, $(R^1\text{-}2, W\text{-}2, R^2\text{-}1, X\text{-}1, Y\text{-}2, B\text{-}1)$, $(R^1\text{-}2, W\text{-}2, R^2\text{-}1, X\text{-}1, Y\text{-}2, B\text{-}2)$, $(R^1\text{-}2, W\text{-}2, R^2\text{-}1, X\text{-}1, Y\text{-}2, B\text{-}3)$, $(R^1\text{-}2, W\text{-}2, R^2\text{-}1, X\text{-}1, Y\text{-}2, B\text{-}4)$, $(R^1\text{-}2, W\text{-}2, R^2\text{-}1, X\text{-}1, Y\text{-}2, B\text{-}5)$, $(R^1\text{-}2, W\text{-}2, R^2\text{-}1, X\text{-}1, Y\text{-}2, B\text{-}6)$, $(R^1\text{-}2, W\text{-}2, R^2\text{-}1, X\text{-}1, Y\text{-}2, B\text{-}7)$, $(R^1\text{-}2, W\text{-}2, R^2\text{-}1, X\text{-}1, Y\text{-}2, B\text{-}8)$, $(R^1\text{-}2, W\text{-}3, R^2\text{-}1, X\text{-}1, Y\text{-}2, B\text{-}1)$, $(R^1\text{-}2, W\text{-}3, R^2\text{-}1, X\text{-}1, Y\text{-}2, B\text{-}2)$, $(R^1\text{-}2, W\text{-}3, R^2\text{-}1, X\text{-}1, Y\text{-}2, B\text{-}3)$, $(R^1\text{-}2, W\text{-}3, R^2\text{-}1, X\text{-}1, Y\text{-}2, B\text{-}4)$, $(R^1\text{-}2, W\text{-}3, R^2\text{-}1, X\text{-}1, Y\text{-}2, B\text{-}5)$, $(R^1\text{-}2, W\text{-}3, R^2\text{-}1, X\text{-}1, Y\text{-}2, B\text{-}6)$, $(R^1\text{-}2, W\text{-}3, R^2\text{-}1, X\text{-}1, Y\text{-}2, B\text{-}7)$, $(R^1\text{-}2, W\text{-}3, R^2\text{-}1, X\text{-}1, Y\text{-}2, B\text{-}8)$ $(R^1\text{-}5, W\text{-}2, R^2\text{-}1, X\text{-}1, Y\text{-}1, B\text{-}1)$, $(R^1\text{-}5, W\text{-}2, R^2\text{-}1, X\text{-}1, Y\text{-}1, B\text{-}2)$, $(R^1\text{-}5, W\text{-}2, R^2\text{-}1, X\text{-}1, Y\text{-}1, B\text{-}3)$, $(R^1\text{-}5, W\text{-}2, R^2\text{-}1, X\text{-}1, Y\text{-}1, B\text{-}4)$, $(R^1\text{-}5, W\text{-}2, R^2\text{-}1, X\text{-}1, Y\text{-}1, B\text{-}5)$, $(R^1\text{-}5, W\text{-}2, R^2\text{-}1, X\text{-}1, Y\text{-}1, B\text{-}7)$, $(R^1\text{-}5, W\text{-}2, R^2\text{-}1, X\text{-}1, Y\text{-}1, B\text{-}8)$, $(R^1\text{-}5, W\text{-}3, R^2\text{-}1, X\text{-}1, Y\text{-}1, B\text{-}1)$, $(R^1\text{-}5, W\text{-}3, R^2\text{-}1, X\text{-}1, Y\text{-}1, B\text{-}2)$, $(R^1\text{-}5, W\text{-}3, R^2\text{-}1, X\text{-}1, Y\text{-}1, B\text{-}3)$, $(R^1\text{-}5, W\text{-}3, R^2\text{-}1, X\text{-}1, Y\text{-}1, B\text{-}4)$, $(R^1\text{-}5, W\text{-}3, R^2\text{-}1, X\text{-}1, Y\text{-}1, B\text{-}5)$, $(R^1\text{-}5, W\text{-}3, R^2\text{-}1, X\text{-}1, Y\text{-}1, B\text{-}6)$, $(R^1\text{-}5, W\text{-}3, R^2\text{-}1, X\text{-}1, Y\text{-}1, B\text{-}7)$, $(R^1\text{-}5, W\text{-}3, R^2\text{-}1, X\text{-}1, Y\text{-}1, B\text{-}8)$, $(R^1\text{-}5, W\text{-}3, R^2\text{-}1, X\text{-}1, Y\text{-}1, B\text{-}1)$, $(R^1\text{-}5, W\text{-}3, R^2\text{-}1, X\text{-}1, Y\text{-}1, B\text{-}2)$, $(R^1\text{-}5, W\text{-}3, R^2\text{-}1, X\text{-}1, Y\text{-}1, B\text{-}3)$, $(R^1\text{-}5, W\text{-}3, R^2\text{-}1, X\text{-}1, Y\text{-}1, B\text{-}4)$, $(R^1\text{-}5, W\text{-}3, R^2\text{-}1, X\text{-}1, Y\text{-}1, B\text{-}5)$, $(R^1\text{-}5, W\text{-}3, R^2\text{-}1, X\text{-}1, Y\text{-}1, B\text{-}6)$, $(R^1\text{-}5, W\text{-}3, R^2\text{-}1, X\text{-}1, Y\text{-}1, B\text{-}7)$, $(R^1\text{-}5, W\text{-}3, R^2\text{-}1, X\text{-}1, Y\text{-}1, B\text{-}8)$, $(R^1\text{-}5, W\text{-}2, R^2\text{-}1, X\text{-}1, Y\text{-}2, B\text{-}1)$, $(R^1\text{-}5, W\text{-}2, R^2\text{-}1, X\text{-}1, Y\text{-}2, B\text{-}2)$, $(R^1\text{-}5, W\text{-}2, R^2\text{-}1, X\text{-}1, Y\text{-}2, B\text{-}3)$, $(R^1\text{-}5, W\text{-}2, R^2\text{-}1, X\text{-}1, Y\text{-}2, B\text{-}4)$, $(R^1\text{-}5, W\text{-}2, R^2\text{-}1, X\text{-}1, Y\text{-}2, B\text{-}5)$, $(R^1\text{-}5, W\text{-}2, R^2\text{-}1, X\text{-}1, Y\text{-}2, B\text{-}6)$, $(R^1\text{-}5, W\text{-}2, R^2\text{-}1, X\text{-}1, Y\text{-}2, B\text{-}7)$, $(R^1\text{-}5, W\text{-}2, R^2\text{-}1, X\text{-}1, Y\text{-}2, B\text{-}8)$, $(R^1\text{-}5, W\text{-}3, R^2\text{-}1, X\text{-}1, Y\text{-}2, B\text{-}1)$, $(R^1\text{-}5, W\text{-}3, R^2\text{-}1, X\text{-}1, Y\text{-}2, B-2), (R¹-5, W-3, R²-1, X-1, Y-2, B-3), (R¹-5, W-3, R²-1, X-1, Y-2, B-4), (R¹-5, W-3, R²-1, X-1, Y-2, B-5), (R¹-5, W-3, R²-1, X-1, Y-2, B-6), (R¹-5, W-3, R²-1, X-1, Y-2, B-7), (R¹-5, W-3, R²-1, X-1, Y-2, B-8), (R¹-5, W-2, R²-1, X-1, Y-2, B-1), (R¹-5, W-2, R²-1, X-1, Y-2, B-2), (R¹-5, W-2, R²-1, X-1, Y-2, B-3), (R¹-5, W-2, R²-1, X-1, Y-2, B-4), (R¹-5, W-2, R²-1, X-1, Y-2, B-5), (R¹-5, W-2, R²-1, X-1, Y-2, B-6), (R¹-5, W-2, R²-1, X-1, Y-2, B-7), (R¹-5, W-2, R²-1, X-1, Y-2, B-8), (R¹-5, W-3, R²-1, X-1, Y-2, B-1), (R¹-5, W-3, R²-1, X-1, Y-2, B-2), (R¹-5, W-3, R²-1, X-1, Y-2, B-3), (R¹-5, W-3, R²-1, X-1, Y-2, B-4), (R¹-5, W-3, R²-1, X-1, Y-2, B-5), (R¹-5, W-3, R²-1, X-1, Y-2, B-6), (R¹-5, W-3, R²-1, X-1, Y-2, B-7), (R¹-5, W-3, R²-1, X-1, Y-2, B-8)

Experiment 1: Affinity for NPY Y5 Receptor cDNA sequence encoding a human NPY Y5 receptor (WO96/16542) was cloned in a vector pME18S (Takebe et al. Mol. Cell. Biol. 8, 8957). The obtained expression vector was transfected into CHO cells as a host by using Lipofect AMINE reagent (Trademark, Gibco BRL Co., Ltd.) according to the instruction manual. The cells that stably express NPY Y5 receptor were obtained.

The membranes prepared from the CHO cells expressing NPY Y5 receptor, the compound of the present invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the membrane was filtered from the mixture through a glassfilter (GF/C) presoaked with 1% polyethyleneimine. After washing with 50 mM Tris-HCl buffer (pH 7.4), radioactivity retained on the filters was quantified with a gamma counter. Nonspecific binding was defined as the amount of radioactivity bound to the membranes after incubation in the presence of 200 nM of peptide YY. The 50% inhibitory concentration of the test-compound against the specific peptide YY binding (IC$_{50}$ value) was calculated (Inui, A. et al. Endocrinology 131, 2090-2096 (1992)). The results are shown below.

| Example I-4 | 2.3 nM |
|---|---|
| Example I-8 | 1.1 nM |
| Example I-17 | 0.88 nM |
| Example I-23 | 1.12 nM |

The compounds of the present invention inhibited the binding of peptide YY (NPY homologue) to NPY Y5 receptor, indicating that the compounds of the present invention have an affinity for the NPY Y5 receptor.

Experiment 2

Under ether anesthesia the skull of male C57BL/6J mice (12-14 week old, 25-30 g) was exposed by making an incision from external occipital crest to nasal dorsum, and drilled in the 1-mm lateral position to the left following 1-mm posterior from bregma. After recovery from anesthesia mice were dosed with either 0.5% hydroxypropylmethyl cellulose solution (Shin-Etsu Chemical Co., Ltd.) or the compounds of the present invention suspended in the 0.5% hydroxypropylmethyl cellulose solution. At one hour after the treatment, each animal received an NPY Y5 receptor specific agonist, [cPP$^{1-7}$, NPY$^{19-23}$, Ala$^{31}$, Aib$^{32}$, Gln$^{34}$]-hPancreatic Polypeptide (0.1 nmol/1.5 μL/mouse) through the skull opening using a canula. Residual food was measured at 2 and 4 hours after the treatment, and the difference in food intake between the compounds-treated mice and 0.5% hydroxymethyl cellulose solution-treated mice was calculated. The compound at 6 mg/kg caused 43% to 90% reduction in food intake of mice compared to the treatment with 0.5% hydroxypropylmethyl cellulose solution, which was statistically significant.

Formulation Example 1

Tablets

| Compound (I) | 15 mg |
|---|---|
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

All of the above ingredients except for calcium stearate are uniformly mixed. Then the mixture is crushed, granulated and dried to obtain a suitable size of granules. Next, calcium stearate is added to the granules. Finally, tableting is performed under a compression force.

Formulation Example 2

Capsules

| Compound (I) | 10 mg |
|---|---|
| Magnesium stearate | 10 mg |
| Lactose | 80 mg |

The above ingredients are mixed uniformly to obtain powders or fine granules, and then the obtained mixture is filled into capsules.

Formulation Example 3

Granules

| Compound (I) | 30 g |
|---|---|
| Lactose | 265 g |
| Magnesium stearate | 5 g |

After the above ingredients are mixed uniformly, the mixture is compressed, crushed, granulated and sieved to obtain a suitable size of granules.

Industrial Applicability

As shown in the above Experiments, the compounds of the present invention have an NPY Y5 receptor antagonistic activity. Therefore, the compounds of the present invention are very useful as an anti-obesity drug and anorectic agent.

The invention claimed is:

1. A compound of the formula (I):

[Formula 1]

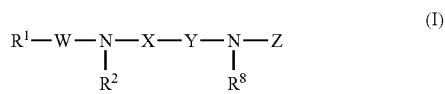

or a pharmaceutically acceptable salt thereof,
wherein
$R^1$ is optionally substituted lower alkyl,
$R^2$ and $R^8$ are each independently hydrogen or lower alkyl,
X is optionally substituted cycloalkylene,
or —$NR^2$—X— may be a group of the formula:

[Formula 4]

wherein a group of the formula:

[Formula 5]

is piperidinediyl, piperazinediyl, pyridindiyl, pyrazinediyl, pyrrolidinediyl or pyrrolediyl,
U is a bond, lower alkylene or lower alkenylene,
Y is —$OCONR^7$—, —$CONR^7$— or —$CSNR^7$—,
$R^7$ is hydrogen or lower alkyl,
Z is optionally substituted carbocyclyl, or optionally substituted heterocyclyl,
W is —S(=O)n-,
n is 2,
provided that Z is not carbocyclyl substituted with non-halogeno lower alkoxy, and
provided that 5-Methyl-4,5,6,7-tetrahydro-thiazolo[5,4-c]pyridine-2-carboxylic acid [2-[(5-chloro-1H-indole-2-carbonyl)-amino]-5-(N',N'-dimethyl-hydrazinocarbonyl)-cyclohexyl]-amide and 5-Methyl-4,5,6,7-tetrahydro-thiazolo[5,4-c]pyridine-2-carboxylic acid [2-[(5-chloro-4-fluoro-1H-indole-2-carbonyl)-amino]-5-(N',N'-dimethyl-hydrazinocarbonyl)-cyclohexyl]-amide are excluded.

2. The compound, or pharmaceutically acceptable salt thereof of claim 1, wherein $R^2$ and $R^8$ are each independently hydrogen.

3. The compound, or pharmaceutically acceptable salt thereof of claim 1, wherein Y is —$CONR^7$- and $R^7$ is hydrogen or lower alkyl.

4. The compound, or pharmaceutically acceptable salt thereof of claim 3, wherein $R^7$ is hydrogen.

5. The compound, or pharmaceutically acceptable salt thereof of claim 1, wherein Z is meta-substituted phenyl, para-substituted phenyl, meta- and para-disubstituted phenyl or meta-disubstituted phenyl.

6. The compound, or pharmaceutically acceptable salt thereof of claim 1, wherein Z is a group of the formula:

[Formula 8]

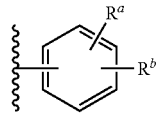

wherein
Ra is hydrogen or an electron-withdrawing group, and
Rb is an electron-withdrawing group.

7. The compound, or pharmaceutically acceptable salt thereof of claim 6, wherein
Ra is hydrogen, halogen, halogeno lower alkyl, halogeno lower alkoxy, nitro or phenyl, and
Rb is halogen, halogeno lower alkyl, halogeno lower alkoxy, nitro or phenyl.

* * * * *